(12) United States Patent
Sabesan

(10) Patent No.: US 7,485,718 B2
(45) Date of Patent: Feb. 3, 2009

(54) CHEMICAL SYNTHESIS OF LOW MOLECULAR WEIGHT POLYGLUCOSAMINES AND POLYGALACTOSAMINES

(75) Inventor: Subramaniam Sabesan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 410 days.

(21) Appl. No.: 11/154,457

(22) Filed: Jun. 16, 2005

(65) Prior Publication Data

US 2006/0287515 A1     Dec. 21, 2006

(51) Int. Cl.
*C08B 37/00* (2006.01)
*C07H 5/04* (2006.01)
*C07H 3/00* (2006.01)

(52) U.S. Cl. .................... 536/55.3; 536/55.1; 536/55.2; 536/53; 536/124; 536/123.1; 536/123.13; 514/61; 514/62; 514/54

(58) Field of Classification Search .................. 514/61, 514/54, 62; 526/55.1; 536/55.2, 55.3, 124, 536/123.1, 55.1, 53, 123.13
See application file for complete search history.

(56) References Cited

U.S. PATENT DOCUMENTS

| 4,927,826 | A | 5/1990 | Guthrie et al. |
| 6,541,467 | B1 | 4/2003 | Ho et al. |
| 2004/0019198 | A1 | 1/2004 | Crich et al. |

FOREIGN PATENT DOCUMENTS

WO    WO 03/026677 A1    4/2003

OTHER PUBLICATIONS

Ohlsson et al. (Carbohydrate Research vol. 329, No. 1, (2000) pp. 49-55).*
Yang et al. (Tetrahedron Letters vol. 43, No. 42 (2002), 7561-7563).*
(Kichin Kichin Kenkyu (2004), 10 (2), 51-56) (Abstract Sent).*
Ismail et al. (Al-Azhar Bulletin of Science (1999), 10 (1), 41-50)(Abstract Sent).*
Roland (Journal de Microscopie (Paris) (1974), 21 (3), 233-44)(Abstract Sent).*
Kanie et. al., Orthogonal Glycosylation Strategy in Oligosaccharide Synthesism J. Am. Chem. Soc., 1994, vol. 116:12073-12074.
Fugedi et. al., Thioglycosides as Glycosylating Agents in Oligosaccharide Synthesis, Glycoconjugate Journal, 1987, vol. 4:97-108.
Akira Hasegawa et. al., Synthetic Studies on Sialoglycoconjugates 25: Reactivity of Glycosyl Promoters in X-Glycosylation of N-Acetyl-Neuraminic Acid With the Primary and Secondary Hydroxyl Groups in the Suitably Protected Galactose and Lactose Derivatives, J. Carbohydrate Chemistry, 1991, vol. 10:493-498.
G.H. Veeneman et. al., Iodonium Ion Promoted Reactions at the Anomeric Centre. II. An Efficient Thioglycoside Mediated Approach Toward the Formation of 1,2 Trans Linked Glycosides and Glycosidic Esters, Tetrahedron Letters, 1990, vol. 31:1331-1334.
Osamu Kanie et. al., Orthogonal Glycosylation Strategy in Oligosaccharide Synthesis, J. Am. Chem. Soc., 1994, vol. 116:12073-12074.
Peter Fugedi et. al., A Novel Promoter for the Efficient Construction of 1,2 Trans Linkages in Glycoside Synthesis, Using Thioglycosides as Glycosyl Donors, Carbohydrate Research, 1986, vol. 149:9-12.
Xuefei Huang et. al., Iterative One-Pot Synthesis of Oligosaccharides, Angew. Chem. Int., 2004, vol. 43:5221-5224.
International Search Report Dated May 11, 2007, International Application No. PCT/US2005/022116, International Filing Date: Jun. 21, 2005.
N. K. Kochetkov, et al., Synthesis of the Capsular Polysaccharide of Streptococcus Pneumoniae Type 14, Tetrahedron, 1987, vol. 43, No. 13, pp. 3109-3121.
Aurelio Maranduba et al., Glycosylation of Lactose: Synthesis of Branched Oligosaccharides Involved in the Biosynthesis of Glycolipids Having Blood-Group 1 Activity, Carbohydrate Research, 1986.
Christian Bernlind et al., Synthesis of a D,D- and L,D-heptose-containing Hexasaccharide Corresponding to a Structure from Haemophilus ducreyi Lipopolysaccharides, Tetrahedron: Asymmetry 11, 2000, pp. 481-492.

* cited by examiner

*Primary Examiner*—Shaojia Anna Jiang
*Assistant Examiner*—Michael C Henry

(57) ABSTRACT

A process for the synthesis of beta linked low molecular weight polymers of galactosamine and glucosamine has been developed. Through the use of high amounts of activating agents, efficient coupling of stable monomers is achieved. Using this process, chain extension is through the addition of single monomers, providing populations of single chain length polyhexosamines.

18 Claims, 2 Drawing Sheets

CHEMICAL SYNTHESIS OF LOW MOLECULAR WEIGHT POLYGLUCOSAMINES AND POLYGALACTOSAMINES

FIELD OF THE INVENTION

The present invention is directed processes for chemical synthesis of low molecular weight polymers of galactosamine and glucosamine. Also provided are a novel derivatized monomer building block that is useful for the processes, and a process for joining the monomer building block in beta linkage. The processes disclosed herein allow stepwise addition of a monomer to lengthen the polymer chain by one unit at a time.

BACKGROUND

Chitosan, which is a β1,4-linked glucosamine polymer, is known to provide antimicrobial activity useful in a wide range of applications including in food preparation and packaging, in personal hygiene such as in garments and personal care articles, and in locations with high potential for microbial contamination such as bathrooms and hospitals. In addition, oligosaccharides of chitosan derivatives were found to have anti-inflamatory properties providing potential use as a pharmaceutical, dietary supplement, or cosmetic component for treatment of inflammation (WO 03026677). Polygalactosamines with alpha linkages are found in nature and β-galactosamines in an acylated form are found as structural components of chondrointin sulfate and dermatan sulfate, compounds that are a part of the proteoglycan structure found in cartilage. Low molecular weight polygalactosamines may have chondroprotective effects and/or other important biological properties, and thus may be useful pharmaceutically.

Chitosan is the commonly used name for poly-[1-4]-β-D-glucosamine. Chitosan is chemically derived from chitin, which is a poly-[1-4]-β-N-acetyl-D-glucosamine, and which, in turn, is derived from the cell walls of fungi, the shells of insects and, especially, crustaceans. Chitin is treated with strong alkalis to remove acetyl groups producing chitosan. Depending on the specific treatment of chitin, chitosan can vary in the degree of deacetylation. Subsequent treatment with mineral acids or enzymes is used to break down the natural chitosan polymers (up to around 1.2 megaDaltons in size) into shorter β1,4-linked 2-amino-2-deoxy-glucopyranosyl polymers. Chitosan preparations that are obtained in this manner, and are commercially available at low cost (from, for example, Primex Corporation (Norway), Biopolymer Engineering, Inc. (St. Paul, Minn.), Biopolymer Technologies, Inc. (Westborough, Mass.), and CarboMer, Inc. (Westborough, Mass.)), generally contain polymers that include a range of sizes, including polymers that are larger than 10,000 Daltons in size and are insoluble in aqueous media, but can be dissolved by converting the glucosamine residue to its acid salt. This limits their application, especially in the food industry, since the salts tend to produce an undesired taste.

Commercial scale preparations of predominantly single chain length low molecular weight polyglucosamines derived from chitosan are generally not available due to the difficulty of purification. An alternative source of these polymers would be through chemical synthesis, yet there has been little success. Forming linkages of glucosamine and galactosamine at the 3-, 4-, and 6-hydroxyls can be problematic due to low reactivity, with the 4-hydroxyl groups of glucosamine or galactosamine units having particularly low reactivity. Kanie et al. (J. Am. Chem. Soc., 1994, 116, 12073-12074) had limited success in the synthesis of a precursor of a gluocsamine heptamer using block synthesis of fragments containing orthogonal protecting groups. US 2004/0019198 discloses a process in which a glycosidic bond is formed using a thioglycoside that is activated by an N,N-dialkylsulfinamide and trifluoromethanesulfonic anhydride. Using the disclosed method, polymer-supported synthesis of β-mannopyranoside-type glycosidic bonds is achieved, producing various β-mannosides.

Thioglycosides are known to be shelf stable monomers for use in the synthesis of oligosaccharides (Fugedi et al., Glycoconjugate Journal, 1987, 4:97-108). However, thioglycosides generally have to be activated with strong electrophiles prior to coupling to sugar hydroxyl groups. Thioglycoside activation procedures are known and are described in US 20040019198, but application of the activated thioglycosides for the efficient synthesis of multi-gram quantities of β-linked low molecular weight polymers of galactosamine and glucosamine is lacking.

Thus there is a need for processes for economical large-scale synthesis of single-species enriched free β-linked low molecular weight polymers of galactosamine and glucosamine. Such polymers are useful in antimicrobial, anti-inflammatory, and/or other applications.

SUMMARY OF THE INVENTION

One aspect of the present invention is a process for forming a glycosidic linkage between two hexoses, comprising:
a. providing a suitably protected thioglycoside donor and a suitably protected glycosyl acceptor, both of which are hexoses;
b. activating the thioglycoside donor using as activating agents an N-haloimide and at least about a 0.5 molar equivalent amount, to the glycosyl acceptor, of a perfluoroalkyl sulfonic acid in the presence of said acceptor; and
c. reacting the thioglycoside donor and glycosyl acceptor at a temperature from about −20° C. to about −70° C.;
wherein the thioglycoside and the glycosyl acceptor form a beta glycosidic linkage.

Another aspect of the present invention is a process of extending a chain of a polyhexose having a protecting group at a linkage position comprising:
a removing the protecting group from the polyhexose linkage position to form a polyhexose acceptor;
b providing a suitably protected thioglycoside donor;
c activating the polyhexose and the thioglycoside using as activating agents an N-haloimide and at least a 0.5 molar amount of a perfluoroalkyl sulfonic acid; and
d reacting the thioglycoside donor and polyhexose acceptor at a temperature from about −20° C. to about −70° C.;

wherein the thioglycoside and the polyhexose form a beta linked polyhexose that has a length of x+1 monomer units, wherein x is the length of the starting polyhexose.

In preferred embodiments of processes of the present invention, the thioglycoside donor has the formula:

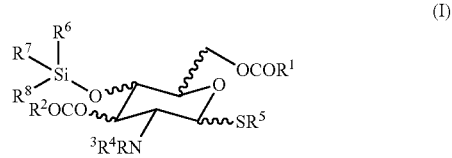

(I)

wherein $R^1$ and $R^2$ are each independently selected from H and $C_1$ to $C_{20}$ alkyl, aryl, and aralkyl groups; $R^3$ and $R^4$ are each independently selected from monofunctional acyl, bifunctional acyl, phthaloyl, trichloroacetyl, and tetrachlorophthaloyl groups; and $R^5$, $R^6$, $R^7$ and $R^8$ are each independently selected from $C_1$ to $C_{20}$ alkyl, aryl, and aralkyl groups.

A further aspect of the present invention is a process of deprotecting a synthetic polyhexose product comprising treating the product at refluxing temperature with hydrazine and n-butanol such that substantially all protecting groups are removed in one step.

Another aspect of the present invention is a process of isolating a synthetic polyhexose product comprising purifying the product by selective extraction.

DETAILED DESCRIPTION

Figure 1:
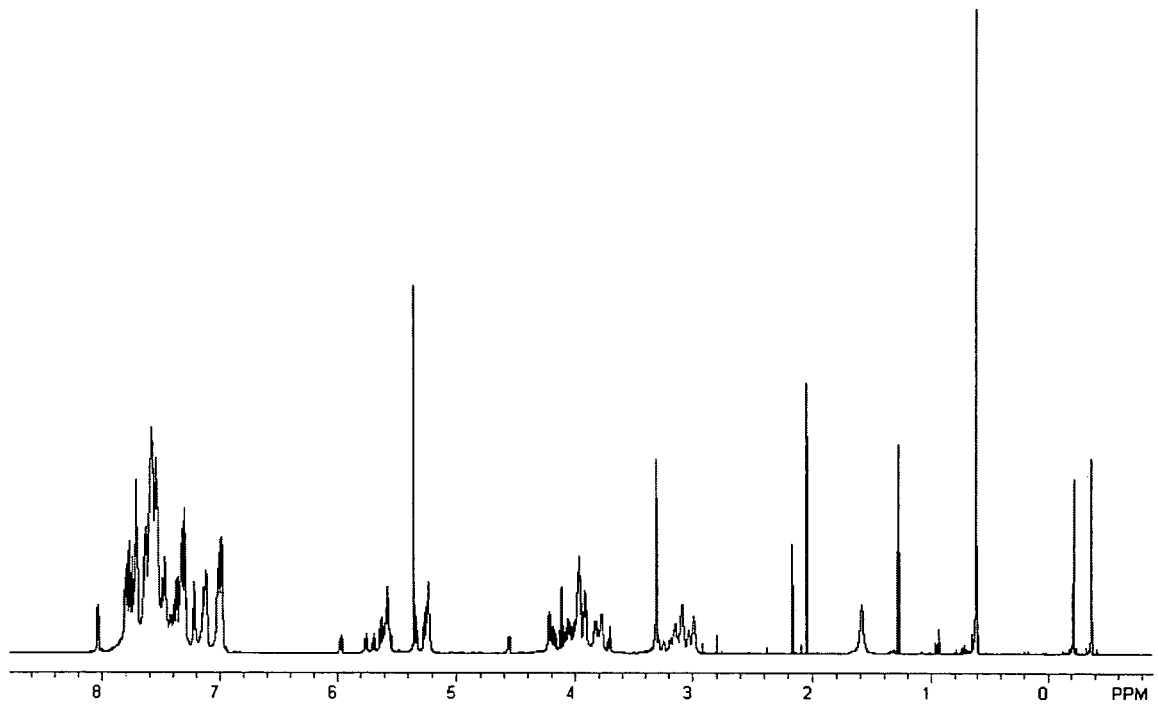
FIG. 1 is the 750 MHz Proton NMR spectrum in $CD_2Cl_2$ of an undecasaccharide derivative (product 27 in Example 22).
Figure 2:
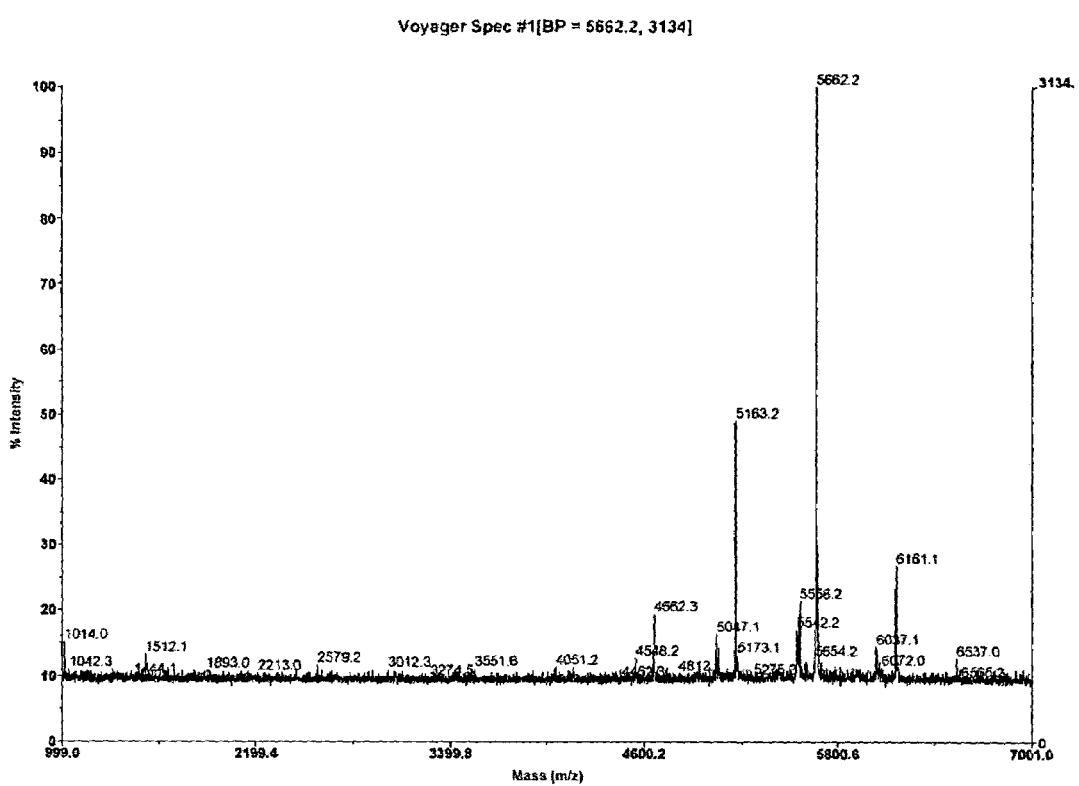
FIG. 2 is the MALDI Spectrum of the synthetic undecasaccharide derivative product 27.

The present invention provides processes for synthesizing multi-gram quantities of low molecular weight polymers of galactosamine and glucosamine, that are scalable for commercial use. The processes allow the use of simple purification procedures and do not require cost prohibitive chromatographic separation procedures. The low molecular weight polymers, called oligoglucosamines, are made by efficient coupling of monomers that are stable to storage. Stepwise addition of a specific type of monomer, described hereinbelow and in copending patent application number CL 2695, to a growing polymer chain results in the synthesis of a defined chain length polymer, providing the ability to produce different preparations of molecules that are each enriched for a specific size polymer.

The processes also permit large-scale preparations of low molecular weight polymers of galactosamine and glucosamine that are enriched in a single size species.

When an amount, concentration, or other value or parameter is recited herein as either a range, preferred range or a list of upper preferable values and lower preferable values, the recited amount, concentration, or other value or parameter is intended to include all ranges formed from any pair of any upper range limit or preferred value and any lower range limit or preferred value, regardless of whether such ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Unless otherwise stated, the following terms, as used herein, have the following meanings.

The term "antibacterial," as used herein, means bactericidal as is commonly known in the art. The number of bacteria present after contact with an antibacterial material is substantially reduced from the number initially present. The number of bacteria present is normally measured as colony forming units.

The term "antimicrobial", as used herein, means antibacterial as well as having fungicidal and antiviral activities as is commonly known in the art.

The term "enriched population" means a population of polymers containing at least 80% of a single chain length polymer. An enriched population may result from a process of low molecular weight hexose polymer synthesis according to the instant invention, or through other processes. An enriched population may have more than 80% of a single chain length polymer, such as 85%, or in particularly efficient reactions, an enriched population may include 90% or greater of a single chain length polymer.

It has been discovered that a particular type of thioglycoside monomer can be very efficiently coupled to a glycosyl acceptor with least reactive groups of type represented by formula (II) by using activating agents generated from N-haloimides and an approximately equimolar amount of a strong protic acid. The thioglycoside monomer is a novel compound represented by formula (I):

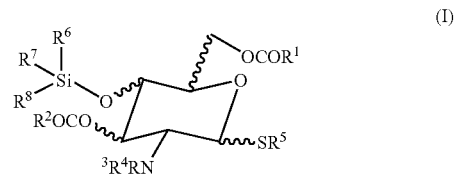

(I)

where $R^1$ and $R^2$ are each independently selected from H and $C_1$ to $C_{20}$ alkyl, aryl, and aralkyl groups;

$R^3$ and $R^4$ are each independently selected from monofunctional acyl, bifunctional acyl, phthaloyl, trichloroacetyl, and tetrachlorophthaloyl groups;

and $R^5$, $R^6$, $R^7$ and $R^8$ are each independently selected from $C_1$ to $C_{20}$ alkyl, aryl, and aralkyl groups.

Preferably $R^1$ and $R^2$ are phenyl groups.

Preferably $R^3$ and $R^4$ are acyl groups derived from a phthaloyl unit.

Preferably $R^5$ is a p-toluyl group.

Preferably $R^6$ and $R^7$ are methyl groups.

The term "shelf stable," as used herein, means that the compound remains intact with storage at room temperature and when exposed to moisture and air of laboratory storage conditions.

The term "large scale" refers to tens of grams to kilogram quantities of material.

The term "low molecular weight polymer" refers to a chain of monomer units that is greater than one unit and up to about 50 units in length. Oligomers are polymers with two to about 10 units. Therefore an oligoglucosamine, for example, is a type of low molecular weight polymer.

The term "β-linkages" includes 1,3-, 1,4-, and 1,6-linkages.

The term "linkage position" means the position of the carbon that is a part of the glycosyl bond. In 1,3-, 1,4-, and 1,6-linkages, the linkage position is 3, 4, or 6, respectively, on one glycoside and 1 on the linked glycoside.

The term "non-linkage position" means the position of a carbon which is not a part of the glycosyl bond. For example, in a 1,4 linkage, the 2, 3 and 6 positions are non-linkage positions.

The term "thioglycoside donor" means the glycosyl molecule which participates at the C-1 position in the glycosyl bond.

The term "glycosyl acceptor" means the glycosyl molecule which has a hydroxyl group at the position (either 3, 4, or 6) that will participate in the glycosyl bond and which connects through its oxygen to the C-1 glycosyl residue from the donor. The glycosyl acceptor may be a single unit or a multiple unit chain that is a low molecular weight polymer.

The term "suitably protected thioglycoside donor" means a thioglycoside that has protecting groups at the positions that become non-linkage positions following formation of the glycosidic linkage. Protecting groups are used to prevent reaction at those sites.

The term "suitably protected glycoside acceptor" means a glycoside that has protecting groups at the positions that become non-linkage positions following formation of the glycosidic linkage. Protecting groups are used to prevent reaction at those sites.

Preferably $R^8$ is a tertiary butyl group.

The glycosyl acceptor is represented by the formula:

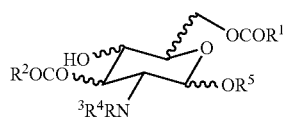

(II)

where $R^1$ and $R^2$ are each selected from H and $C_1$ to $C_{20}$ alkyl, aryl, and aralkyl groups;

$R^3$ and $R^4$ are each independently selected from monofunctional acyl, bifunctional acyl, phthaloyl, trichloroacetyl, and tetrachlorophthaloyl groups; and $R^5$ is selected from $C_1$ to $C_{20}$ alkyl, aryl, and aralkyl groups.

Preferably $R^1$ and $R^2$ are phenyl groups.

Preferably $R^3$ and $R^4$ are acyl groups derived from a phthaloyl unit.

Preferably $R^5$ is a methyl group.

A polymerization process according to the present invention can be illustrated as follows. A unit, e.g, molecule, of monomer (II), the glycosyl acceptor, provides an initial unit onto which units of a monomer (I), the thioglycoside donor, are added to extend the polymer chain. Monomers (I) and (II) can be made from D-glucosamine hydrochloride or D-galactosamine hydrochloride, which are commercially available. To synthesize monomer (I), using synthesis of 1,4-linked glucosamine as an example, the D-glucosamine hydrochloride is derivatized with a phthaloyl group using phthalic anhydride to protect the amine (product 2 in Example 1). The hydroxyl groups are then protected by acetylation (product 3 in Example 2), and the product is purified by crystallization. Next, a benzenethiol group is added to the 1 position (product 4 in Example 2) and the product is purified by washing with protic solvents. The resulting product is deacetylated (product 5 in Example 2), benzoyl protecting groups are added at the 3 and 6 hydroxyl positions (product 6 in Example 2) and the product is purified by crystallization. Finally a silicon protecting group, referred to as a t-butyldimethylsilyl (tB-DMS) group, is added as a temporary protecting group at the 4-hydroxyl group of product 6, creating the compound shown as monomer (I) in Reaction 1 below (S-(p-toluyl) 4-O-(dimethyl-t-butyl silyl)-2-deoxy-3,6-di-O-benzoyl-2-phthalimido-1-thio-β-D-glucopyraoside). This compound represents one example of a monomer (I), which is a suitably protected thioglycoside donor. Each of the individual reactions used in the preparation of monomer (I) is known to one skilled in the art. The combination of reactions and purifications is amenable to large scale preparation of the novel monomer (I), which is an embodiment of the instant invention. The resulting monomer (I) provides a building block for the synthesis of low molecular weight polymers of glucosamine.

A galactosamine glycosyl donor can be used in the place of a glucosamine molecule as a starting point for synthesis of a galactosamine-monomer (I) in the same manner as described above for the glucosamine-monomer (I). The resulting monomer provides a building block for the synthesis of low molecular weight polymers of galactosamine.

One skilled in the art will know that other protecting groups can be used in the preparation of intermediates to glucosamine-monomer (I) or galactosamine-monomer (I). For example, the amine can be protected with monofunctional acyl, bifunctional acyl, trichloroacetyl or tetrachlorophthaloyl groups and the hydroxyl groups can be protected with $C_1$ to $C_{20}$ alkyl, aryl, or aralkyl groups as a part of an ester group. Similarly, the silyl group can be any tri-substituted silicon, substituted with, for example, $C_1$ to $C_{20}$ alkyl, aryl, and aralkyl groups. In addition, one skilled in the art will know that for preparation of a 1, 3 or 1,6 linked polymer the placement of the silicon group is at the 3- or 6-position, respectively, and the hydroxyl group positions shift accordingly.

To synthesize monomer (II), using synthesis of 1,4-linked glucosamine as an example, a similar sequence of reactions as used for monomer (I) is used. The phthaloyl derivative of D-glucosamine hydrochloride (product 3 above) is acetylated and methylated at the 1 position hydroxyl (product 7 in example 3), then deacetylated at the other hydroxyls (product 8 in example 3). Benzoyl groups are added to product 8 at the 3 and 6 positions creating monomer (II) (FIG. 1). Each of these individual steps is carried out using reaction conditions well known to one skilled in the art. The resulting monomer (II) provides the initial unit onto which molecules prepared as for monomer (I) are added for the synthesis of a low molecular weight glucosamine. The compound shown in Reaction 1 below (methyl 2-deoxy-3,6-di-O-benzoyl-2-phthalimido-β-D-glucopyraoside) represents one example of a monomer (II) type compound, which is a suitably protected glycosyl acceptor.

Galactosamine can be used in the place of the starting glucosamine molecule for synthesis of a galactose-monomer (II) in the same manner as described above for monomer (II). The resulting galactose-monomer (II) provides the initial unit onto which molecules prepared as galactose-monomer (I) are added for the synthesis of a low molecular weight galactosamine. In addition, glucosamine and galactosamine may be interchangingly used in the synthesis of monomer (I) and monomer (II) for the synthesis of a mixed composition oligosaccharide. Further, different monomers prepared from different hexosamines can be added alternately, or in any order, to prepare a mixed composition polysaccharide.

One skilled in the art will know that other protecting groups can be used in the preparation of intermediates to monomer (II) or galactose-monomer (II). For example, the amine may be protected with monofunctional acyl, bifunctional acyl, trichloroacetyl or tetrachlorophthaloyl groups and the hydroxyl groups may be protected with with $C_1$ to $C_{20}$ alkyl, aryl, or aralkyl groups as a part of an ester group. In addition, one skilled in the art will know that for preparation of a 1, 3 or 1,6 linked polymer the 4 and 6, or 3 and 4 positions are protected, respectively.

The intermediate products 2-8 leading to the synthesis of monomers (I) and (II) can be obtained by using the steps described above, which result in highly selective reactions. The simplicity of the protecting groups used in the processes for synthesis of monomers (I) and (II) facilitate purification and chain extension, enabling the practical chemical synthesis of polyglucosamines. Though benzoate groups are conventionally considered to be the least preferred protecting groups in oligosaccharide synthesis, due to their causing decreased reactivity of the glycosyl donor and acceptor (as disclosed, for example, in Zhang et al., supra), benzoate groups have been found to be ideally suited for the present synthesis methods. Benzoate groups are used in the instant processes to permit ready crystallization of the product, thus facilitating simplified isolation of the product from impurities and allowing large-scale preparation of the products. It has been found that the use of increased levels of activating agents relative to the monomers improves coupling efficiency of the glycoside formation, thus making the synthesis commercially attractive.

In addition, the silicon protecting group in the monomer (I) serves as a convenient temporary protecting group that can be removed easily for chain extension. By iterative glycosylation and silicon protecting group removal from the product polysaccharide, glycosyl units can be conveniently added to the desired length, as described below. More importantly, the monomer based approach disclosed herein allows the use of low cost thioglycoside agents in excess amounts for near quantitative coupling efficiency in the glycosylation reaction and the ready removal of undesired by-products by simple solvent extraction, and makes it possible to prepare individual members of a family of low molecular weight polymers of glucosamine or galactosamine for biological testing and commercial use. Each member of a family has a unique monomer unit length, with 1 unit being the smallest difference between two members.

Coupling of monomers (I) and (II), as well as coupling of an oligoglucosamine chain+monomer (I), is carried out using thioglycoside activating agents under saturating substrate concentration in the reaction. The thioglycoside activating agents are generated from N-haloimides and strong protic acids. For example, N-halosuccinimides such as N-iodosuccinimide and N-bromosuccinimide can be used as activating agents in combination with strong protic acids such as triflic acid (trifluoromethanesulfonic acid) and other perfluroalkylsulfonic acids. Though triflic acid alone is sufficient to activate the thioglycoside, the combined use of triflic acid and methyltriflate (methyltrifluoromethanesulfonate) was found to facilitate the removal of by-products that may be detrimental to the glycosylation reaction. Thus, while methyltriflate alone was found not to be sufficient to activate the monomer (I), the combination of triflic acid/methyltriflate was found to provide optimal efficiency for reaction and purification conditions.

The activation of thioglycosides is traditionally carried out with catalytic quantities of triflic acid or its salt in conjunction with a molar equivalent or excess of N-halosuccinimide. These conditions were found to be insufficient for efficient glycosylation of monomer (II), especially with a growing glucosamine chain, resulting in either incomplete reaction or no reaction occurring. On the other hand, use of N-halosuccinimide at 1 to 1.5 molar equivalent to monomer (I) and approximately a molar equivalent (to monomer (II)) amount of any perfluoroalkyl sulfonic acid, of which triflic acid is an example, together with a molar equivalent (to monomer (II)) of methyltriflate provides efficient glycosylation. Use of triflic acid in amounts of between about 0.5 and about 1.0 molar equivalent amount can be employed with a lesser efficiency. The coupling efficiency is directly related to the ease of purification of the desired product from starting material. Thus of particular use is approximately a molar equivalent amount each of triflic acid and methyltriflate, for forming a readily purifiable product. Surprisingly, it was found that such high concentrations of triflic acid do not cleave the sugar molecule, especially when the reaction is carried out at low temperatures.

Using the above described activating agents, the coupling reaction can be driven to quantitation, forming the glycosidic linkage, as shown in Reaction 1, which is known to those skilled in the art to be difficult to construct. Shown is an example reaction of glucosamine-monomer (I) and glucosamine-monomer (II) forming a dimer low molecular weight polyglucosamine. The coupling of monomer (I) to the glycosyl acceptor (in this case monomer (II)) is step A.

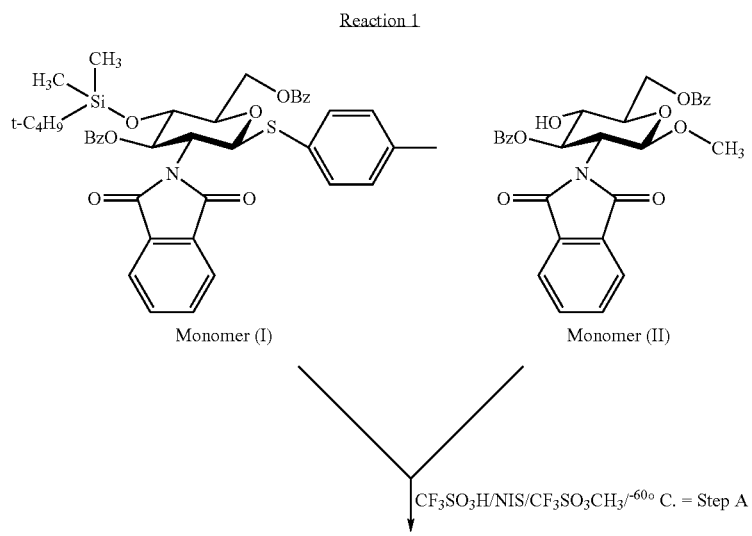

Reaction 1

$CF_3SO_3H/NIS/CF_3SO_3CH_3/^{-60°}$ C. = Step A

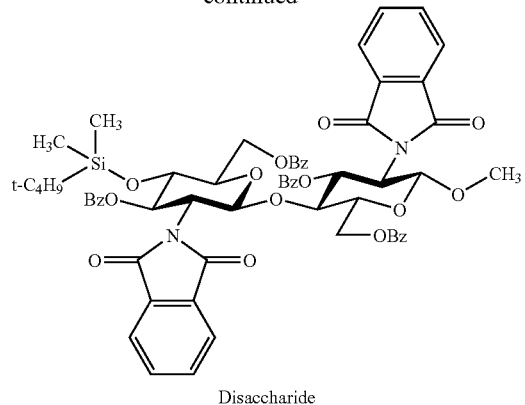

Disaccharide

NIS = N-Iodosuccinimide
Bz = Benzoyl (C₆H₅CO)

In addition, using a minimum amount of reaction solvent keeps the reactants at saturation levels and at high effective concentration, and results in more efficient glycosylation. The activating agents are added to the glycosides and the coupling reaction is carried out at a low temperature. Temperatures from about −20° C. to about −70° C. are desired for the reaction. It is preferred that the temperature for the reaction be less than about −50° C., with −60° C. being a most preferred temperature. The reaction time is from about 15 minutes to about 8 hours. The reaction is desirably allowed to run for a time sufficient for all potential glycosidic linkages to be formed. Preferred is a reaction time between about 4 and about 6 hours.

A general description of a process for coupling of monomer (I), a suitably protected thioglycoside donor, and monomer (II), a glycosyl acceptor, is as follows. Monomer (II) (about 1.0 eq.) and monomer (I) (at least 1 and up to about 3 eq., with about 1-2 eq. being preferred) are dissolved in a minimum of an aprotic solvent, such as methylenechloride, diethylether, acetonitrile, and benzotrichloride. The most preferred solvent is methylenechloride. The solution is cooled to about −55° C. to −60° C. under nitrogen atmosphere with vigorous stirring. Powdered N-Iodosuccinimide (NIS) is added to the cold solution. After about 15 min, a solution of a perfluoroalkyl sulfonic acid, such as triflic acid (about 1.0 eq.) and methyltrifluromethanesulfonate (about 1.0 eq.), dissolved in minimum of aprotic solvent, e.g., methylenechloride, is added in drops, while maintaining the reaction temperature under about −60° C. After the addition, the reaction mixture is maintained at the same temperature with stirring, for about 6 hours and then poured directly over a 1:1 mixture of saturated sodium thiosulfate and saturated sodium bicarbonate solution. Additional solvent such as methylenechloride is employed to dilute the reaction mixture and provide washing of the reaction flask. The solution is thoroughly mixed and the organic layer separated. The organic layer is then washed sequentially with 0.6% bleach solution, water, and saturated sodium bicarbonate solution. The product is recovered by concentration of the solution at reduced pressure. The impurities are removed by dissolving the material in diethylether or ethylacetate, followed by precipitation with n-hexane. It is to be understood that variations known to one skilled in the art can be introduced into the process, without departing from the scope of the invention.

The efficiency of the described coupling reaction reduces the level of undesired by-products and starting materials in reaction mixture following coupling, thereby facilitating the removal of the existing minor impurities through selective solvent extraction methods. There is no need for the commonly used and expensive purification methods of silica gel chromatography, although these methods may be used. Selective washing with organic solvents provides a simplified purification method that is useful for large-scale production. Solvents useful for the washing during purification include diethylether and hexane-ethylacetate mixture. Any combination of solvents in which the product is insoluble, but the impurities and the by-products are soluble, may be used. This selective extraction of impurities derived from excess monomer (I), using solvents in which the desired product is insoluble, is a highly preferred method for isolation of the product.

Following coupling and optional purification, chain extension is carried out. Prior to extension of the disaccharide product, the silicon blocking group is removed from the polyhexose linkage position as shown in Reaction 2 below, step B. The silicon group can be removed, for example, by dissolving in minimum anhydrous tetrahydrofuran (THF), then reacting with acetic acid (2-3 eq.) and n-tetrabutylammonim fluoride solution in THF (1 M, 2-3 eq.). The reaction progress may be monitored either by TLC or NMR of the reaction mixture. Additional methods for removing silicon protecting groups are well known to one skilled in the art.

Upon completion, the reaction mixture is concentrated to dryness, the residue dissolved in solvent such as methylenechloride and washed with water, 1 M aqueous HCl solution, 0.6% bleach solution (to remove the dark brown color), and aqueous saturated sodium bicarbonate solution. The remaining organic layer is dried over anhydrous magnesium sulfate and concentrated to dryness. Purification of the product is typically accomplished by precipitation with, for example, diethylether or an n-hexane-ethyl acetate mixture, which ensures the removal of residual monomer from the previous step as well as the silicon impurity. Any combination of solvents in which the product is insoluble, but the impurities and the by-products are soluble may be used for precipitation.

Additional monomer (I), a suitably protected thioglycoside donor, is then added through a glycosyl bond to the unblocked disaccharide using activating agents as described above. The disaccharide is used in place of monomer (II), as shown in Reaction 2, according to the general coupling procedure described above. Shown is an example reaction of a glucosamine dimer with removal of the silicon blocking group in step B and addition of a glucosamine-monomer (I) forming a trimer low molecular weight polyglucosamine. The coupling of monomer (I) to the glycosyl acceptor (in the example reaction, the glucosamine dimer) is step A.

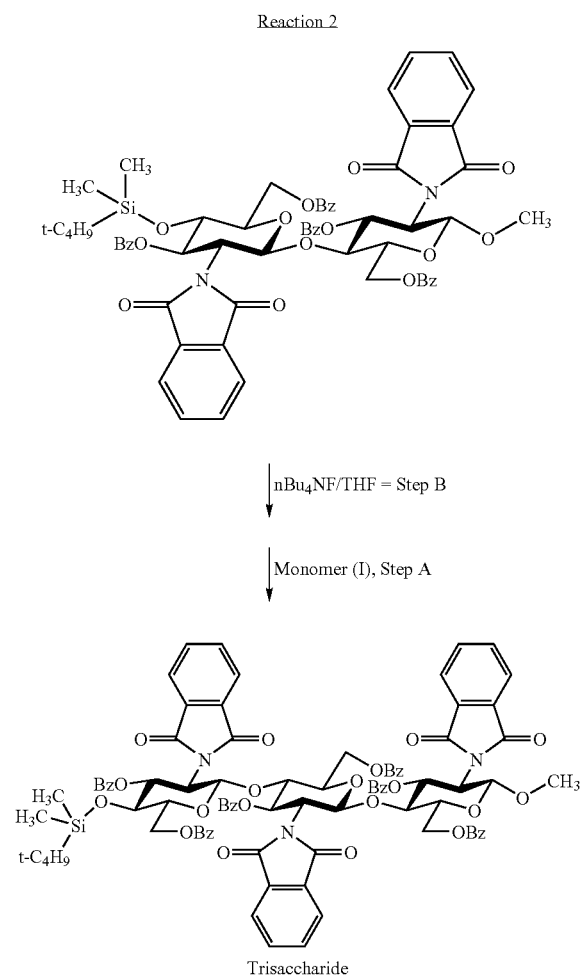

Reaction 2

Purification by organic solvent washing is also as described above. Further rounds of chain extension are accomplished by silicon blocking group removal and addition of monomer (I). The process is repeated in a stepwise manner such that the thioglycoside and the polyhexose form a beta linked polyhexose that has a length of x+1, wherein x is the length of the starting polyhexose and 1 is one monomer unit. Since the reaction at each step is nearly quantitative, the completion of each step results in a product that contains more than about 80% of molecules having a single chain length. Thus the product is enriched in a single anomer of beta linkage oligohexosamine molecules. The steps can be repeated until a polysaccharide chain of desired length up to about 50 units is synthesized.

Preparation of a low molecular weight polymer of galactosamine or glucosamine can be completed by the removal of the remaining protective groups. For a polymer containing 2-5 residues, this is carried out in a two step procedure. First, de-O-benzoylation can be accomplished by Zemplens' method, which is well known to those skilled in the art, using sodium methoxide in methanol. The phthaloyl group can be removed by using an ethylenediamine-derivatized Merrifield resin (P. Stangier, O. Hindsgaul, Synlett. 1996, 2: 179-181), as well known to one skilled in the art. Alternatively, removal of the benzoyl and the phthalimido groups can be accomplished in a single step by treating the protected product at refluxing temperature with hydrazine in n-butanol, followed by selective extraction of the product polyhexosamine with water. The single step method is preferred for polymers of length greater than 4, due to their incomplete de-benzoylation under Zemplens' condition and their lack of solubility in methanol and n-butanol.

The monomer based glycosylation process disclosed herein for polyhexosamine may be suitable for the preparation of polyhexoses as well. For example, glucose and galactose can be used in the place of the starting glucosamine molecule. To construct such a derivative, a suitably protected thioglycoside of hexose with a silicon protecting group at the chain extension site and ester protecting groups at non-linkage positions replaces monomer (I). The glycosylation using a molar equivalent of triflic acid/methyltriflate in combination with N-haloimides under saturating substrate concentration provides high yields of the desired glycoside. Once a high yield of glycosylation is achieved, purification by selective precipitation is effective.

The processes disclosed herein allow the preparation of novel oligohexosamine products, in the form of gram or larger quantities of enriched populations of a single anomer of beta linkage oligohexosamine molecules. An enriched population of a single anomer of beta linkage oligohexosamine molecules, prepared according to the methods disclosed herein, preferably contains at least 80% of chains of oligosaccharide having a single length of from 3 to about 50 units, more preferably from 3 to about 25 units, and even more preferably from 3 to about 11 units.

Such enriched populations of single anomers of beta linked low molecular weight galactosamine or glucosamine polymer can be used as precursors for synthesizing other compounds, which may be biologically active, for use in, e.g., antimicrobial compositions, anti-inflammatory compositions, and other pharmacological applications. For example, an enriched population of single anomer can be used in preparing certain plant growth regulators related to chitin oligomers, such as the nod factors, which are involved in inducing nodulation in legumes, and contain a tetra-1,4-α-aminoglucoside unit that is acylated with the same or different fatty acids at the amino groups. The monomer based approach disclosed herein not only allows the synthesis of such tetra-aminoglucoside derivatives, but also enables the selective introduction of a desired fatty acid molecule. Another naturally occurring β 1-6 linked glucosamine is the endotoxic Lipid A component of the outer membrane of most gram-negative bacteria, which triggers mediators of inflamation in mammalian cells. Lipid A molecules, which are aminoacylated derivatives of β1'-6 linked glucosamine units, can be synthesized through the amine derivatives and can be made using the processes disclosed herein.

An enriched population of a single anomer of beta linked low molecular weight hexose or hexosamine polymer can be a component, along with a carrier, of a composition that is designed to deliver properties provided by the polyhexose or polyhexosamine. The carrier in the composition can include, for example, dissolving agents and inactive ingredients, In addition, the composition can include other active ingredients. The composition is prepared such that it may be applied to a surface by methods such as spraying, dipping, soaking, and wiping or rubbing.

The low molecular weight polyglucosamines can be used as antimicrobial additives, including as anti-dandruff agents in shampoos as disclosed in EP 1384404, and in inhibiting the growth or propagation of spoilage or pathogen microorganisms in foods as disclosed in WO 2003070008. Food products can be treated with an enriched population of a single anomer of beta linkage low molecular weight polyglucosamines such as by adding dry powder or a solution comprising the enriched population to the food. Food that can be treated includes, for example, fresh or processed fruits and vegetables. The food can be coated with a composition containing an enriched population of a single anomer of beta linked low molecular weight hexosamine polymer. The coating need not completely cover the food, but the food is coated to an extent adequate to provide antimicrobial activity for preservation of the food. Polygalactosamines can also provide antimicrobial activity due to their negative charge.

The low molecular weight polyglucosamines of the present invention may be used in pharmaceutical compositions for treatments against inflammatory activity, including treatment of joint disorders such as of rheumatoid arthritis and osteoarthritis as disclosed in WO 2003026677. An enriched population of a single anomer of beta linkage low molecular weight polyglucosamine may be included in the manufacture of a medicament for treatment of these conditions.

The low molecular weight polygalactosamines are potentially useful as chondroprotective pharmaceuticals. Initially, preparations of synthetic low molecular weight polygalactosamines are useful in biological testing applications to identify specific applications.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

The meaning of abbreviations is as follows: "Hz" means hertz, "MHz" means megahertz, "ppm" means parts per million, "HOD" means hydrogen deuteriumoxide, "μ" means micron, "g" means gram(s), "mg" means milligrams, "Kg" means "kilogram(s), "ml" means milliliter(s), "L" means liter(s), "min" means minutes, "h" means hour, "eq." means equivalents, "mmol" means millimole(s), "mol" means mole(s), "M" means molar, "M. wt." means molecular weight, "t-BDMS" refers to a t-butyldimethylsilyl group, "M/e calc" means calculated mass to charge ratio.

General Methods and Materials

Unless specified, all the reagents were purchased from Aldrich Chemical Co (St. Louis, Mo.). Thin layer chromatography was performed on pre-coated plates of Silica Gel 60 $F_{254}$ (EM Science) and the spots were visualized with a spray containing 5% sulfuric acid in ethanol, followed by heating. Column chromatography was done on silica gel 60 (230-400 mesh, EM Science). $^1$H NMR spectra were recorded at 500 MHz. The hydrogen chemical shifts in organic solvents are expressed relative to deuterated methylenechloride, with a reference chemical shift of 5.36 ppm. For solutions of compounds in deuterium oxide or deuterated methanol, the hydrogen chemical shift values are expressed relative to the HOD signal (4.75 ppm at 296° K).

Example 1

Synthesis of 2-deoxy-1,3,4,6-tetra-O-acetyl-2-phthalimido-D-glucopyranose

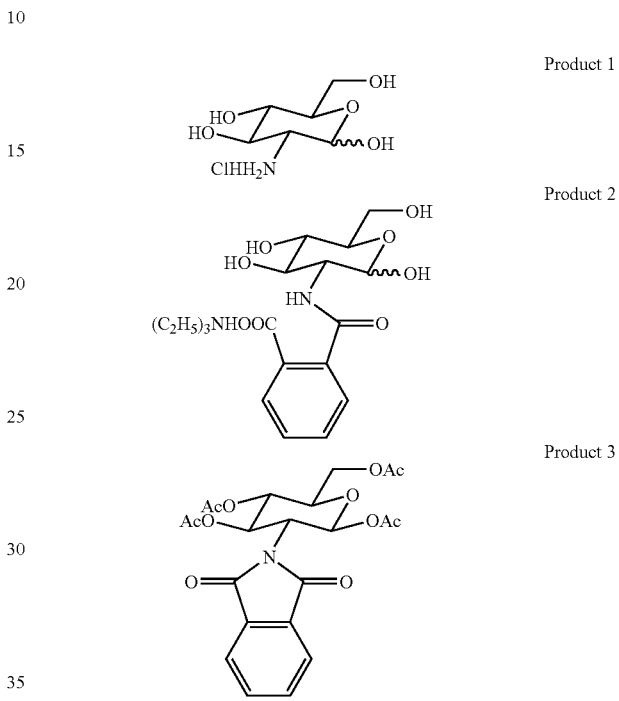

D-Glucosamine hydrochloride (compound 1, 1.0 Kg) was suspended in methanol (5.0 L) and vigorously stirred. NaOH (184.8 g) was dissolved in minimum deionized water and added to the D-Glucosamine/Methanol suspension. The suspension was stirred for 15 min and the insoluble material (sodium chloride) was filtered off by vacuum filtration. The theoretical amount of NaCl formed should be about 270 g.

To the filtrate, phthalic anhydride (342 g) was added and the solution was stirred until most of the solid dissolved (about 30 min). This was then followed by the addition of triethylamine (468 g) and stirred for 10 to 15 min. To the resulting clear solution, another portion of phthalic anhydride (342 g) was added and the mixture was allowed to stir overnight at room temperature. Product usually began to precipitate out after two hours.

The precipitated product was filtered and the residue was washed with minimum ice-cold methanol so as to remove the yellow color from the product. The residue was then washed three times with acetonitrile, with enough solvent added to the filter to completely immerse the solid, and dried at room temperature under high vacuum. The weight of the white solid, product 2, was 954 g. $^1$H-NMR (D$_2$O): 7.74-7.56 (phthalimido hydrogens), 5.42 (H-1α), 4.94 (H-1β), 4.17 and 4.01 (H-6), 3.27 (CH$_2$ of N-ethyl group), 1.35 (CH$_3$ of N-ethyl group).

The product 2 from above (1.01 Kg, made from two batches) was placed in a 10 liter 3 neck round bottom flask set up with an overhead electric stirrer, an N$_2$ inlet and an addition funnel. Acetic anhydride (3 L) and N,N-dimethylaminopyridine (1.0 g) were added to the flask and stirred vigorously. Pyridine (2.8 L) was added slowly and the reaction mixture was stirred for 2 days at room temperature. The reaction mixture was quenched with ice-water (4 L) and the product was extracted with methylenechloride. The organic layer was repeatedly washed with aqueous hydrochloric acid solution, and then with saturated sodium bicarbonate solution. The organic layer was dried over anhydrous magnesium sulfate, filtered, and concentrated to dryness. The product was recrystallized from hot ethanol. Weight of the recrystallized product 3 was 701 g. $^1$H-NMR (CD$_2$Cl$_2$) δ: 7.91-7.80 (phthalimido hydrogens), 6.62 (H-1), 5.59 (H-3), 5.21 (H-4), 4.47 (H-2), 4.36 and 4.16 (H-6), 4.06 (H-5), 2, 12, 2.06, 2.02, 1.88 (acetyl methyl groups). Thus the above NMR chemical shift data verified the structure of product 3, 2-deoxy-1,3,4,6-tetra-O-acetyl-2-phthalimido-D-glucopyranose, which is shown below in Example 2.

Example 2

Synthesis of Monomer (I)

Preparation of intermediate product 4:

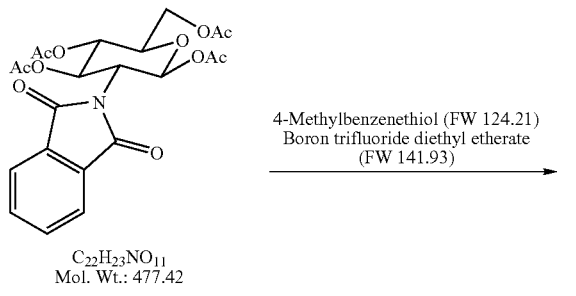

C$_{22}$H$_{23}$NO$_{11}$
Mol. Wt.: 477.42
Product 3

4-Methylbenzenethiol (FW 124.21)
Boron trifluoride diethyl etherate (FW 141.93)

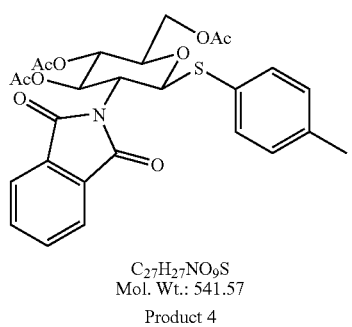

C$_{27}$H$_{27}$NO$_9$S
Mol. Wt.: 541.57
Product 4

Product 3 (464 g) was dissolved in toluene and the solvent was evaporated. This was repeated and the remaining solid was placed on a high vacuum line overnight.

The dried solid was dissolved in minimum methylenechloride (ca. 600 ml), and stirred well. To this, 4-methylbenzenethiol (181 g, 1.45 mol, 1.5 eq.) was added followed by the dropwise addition of boron trifluoride diethyl etherate (BF3-etherate; 165 g, 1, 16 mol, 1.2 equivalent, over 180 min). The reaction mixture was stirred overnight. White crystals formed in the morning when stirring was stopped. The crystals were filtered, giving product 4A. The filtrate was diluted with methylenechloride, washed sequentially with saturated NaHCO3 solution, water, then bicarbonate solution, and dried giving product 4B. Both 4A and 4B products were extensively washed with anhydrous methanol and dried under vacuum. Since the NMR spectrums of 4A and 4B products were identical, these two were combined (Product 4, 426.3 g).

$^1$H-NMR (CD$_2$Cl$_2$) δ: 7.96-7.80 (phthalimido hydrogens), 7.36 & 7.13 (S-aromatic hydrogens), 5.78 (H-3), 5.69 (H-1), 5.13 (H-4), 4.33 (H-2), 4.30 & 4.12 (H-6), 3.93 (H-5), 2.36 (S-Ph-Me group), 2.13, 2.04, 1.85 (methyls of acetyl groups). Thus the NMR spectrum verified the structure of product 4, as shown above.

Preparation of intermediate Product 5

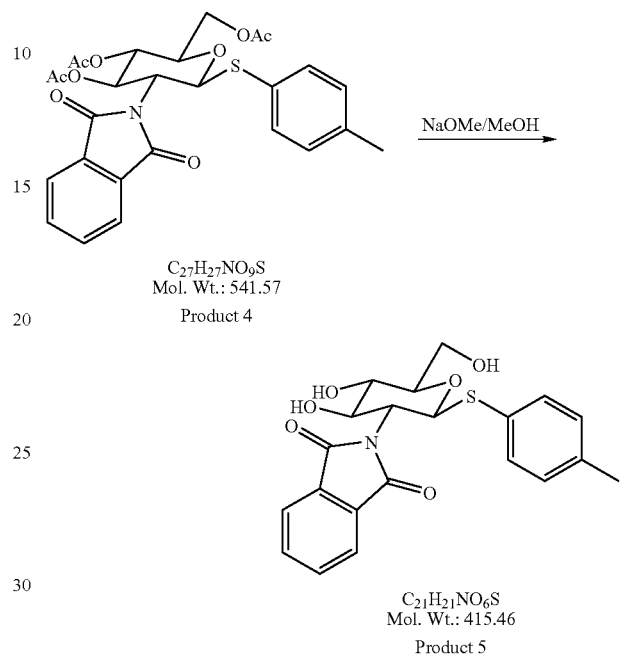

C$_{27}$H$_{27}$NO$_9$S
Mol. Wt.: 541.57
Product 4

NaOMe/MeOH

C$_{21}$H$_{21}$NO$_6$S
Mol. Wt.: 415.46
Product 5

Product 4 (350 g) was suspended in nearly 4 L of dry methanol. To this, 35 ml of 0.5 M sodium methoxide solution was added and the solution immediately turned basic. The suspension was left stirring at room temperature overnight. The solid deposited was filtered and washed with dichloromethane, giving pure Product 5 (232 g). The filtrate was neutralized with sulfonic acid resin and concentrated to dryness. The dry solid was washed with methylenechloride and dried, giving impure compound 5 (43.8 g). $^1$H-NMR (CD$_3$OD) of pure 5 δ: 7.87-7.76 (phthalimido hydrogens), 7.22 & 6.99 (S-aromatic hydrogens), 5.46 (H-1), 4.18 (H-2), 4.03 (H-3), 3.89 & 3.70 (H-6), 3.39 (H-5), 3.37 (H-4), 2.22 (S-Ph-Me group). Thus the NMR spectrum verified the structure of product 5, as shown above.

Preparation of intermediate Product 6

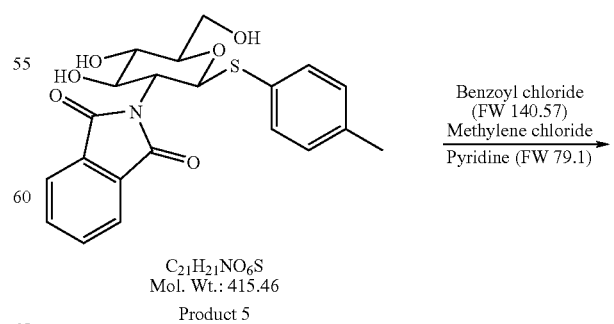

C$_{21}$H$_{21}$NO$_6$S
Mol. Wt.: 415.46
Product 5

Benzoyl chloride (FW 140.57)
Methylene chloride
Pyridine (FW 79.1)

-continued

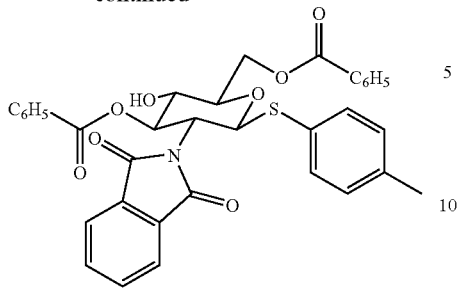

C₃₅H₂₉NO₈S
Mol. Wt.: 623.67
Product 6

Product 5 (295 g; 638; mmol) was suspended in dry toluene (1 L) and evaporated under vacuum. This procedure was repeated once more to ensure the removal of methanol contaminant that is detrimental to the reaction. 265 grams total was recovered. The residue after toluene evaporation was suspended in methylenechloride (3 L) in a 3-neck flask fitted with an overhead stirrer and the suspension was stirred under dry nitrogen atmosphere. The flask was cooled in an ice bath and the following reagents were added: Pyridine=126 g, N,N-Dimethylaminopyridine=500 mg; and Benzoyl Chloride: 171 g (added by means of an addition funnel slowly in drops over 60 min). The reaction mixture was milky white, but began to clear when all benzoyl chloride was added. The reaction was allowed to stir for 18 h at room temperature. The reaction was diluted with methylenechloride and was washed with water (2×), 1 M aqueous HCl (2×), then saturated NaHCO₃ and dried with MgSO₄.

The crude product was recrystallized in 8 liters of hot EtOH, crystals were filtered, and washed in EtOH giving Crop 6A (225 g). The filtrate was concentrated to dryness giving Crop 6B (131 g). A second recrystallization of Crop 6A was done to give pure product 6 (172 g). The residue (40 g) from the filtrate of the second recrystallization had product 6 of purity greater than 95%, as determined by NMR. Crop 6B was not further processed as NMR analysis showed that it had a significant amount of undesired products and was therefore recycled back to compound 5.

¹H-NMR (CD₂Cl₂) δ: 8.14, 7.88, 7.69, 7.57, 7.41 (benzoate hydrogens), 7.80-7.72 (phthalimido hydrogens), 7.34 & 7.00 (S-aromatic hydrogens), 5.93 (H-3), 5.79 (H-1), 4.77 & 3.99 (H-6), 4.47 (H-2), 4.03-3.99 (H-5), 3.91 (H-4), 3.25 (OH), 2.31 (S-Ph-Me group). Thus the NMR spectrum verified the structure of product 6, as shown above.

-continued

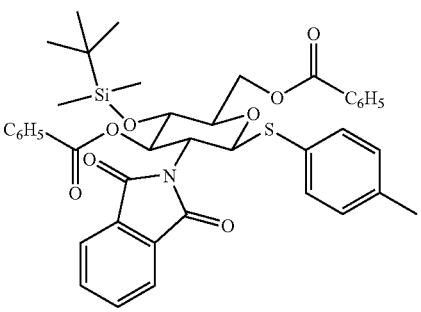

C₄₁H₄₃NO₈SSi
Mol. Wt.: 737.93
Monomer (I)

Product 6 (171.9 g; 275.6 mmol) was dissolved in minimum methylenechloride (350 mL) containing collidine (41.7 g; 344.5 mmol; 1.25 eq.). t-BDMS-Triflate (80.0 g; 303.1 mmol; 1.1 eq.) was added drop-wise by addition funnel (over 50 minutes). The reaction mixture was allowed to stir overnight. The reaction mixture was diluted with methylenechloride and washed sequentially with ice-cold water, 0.5 M aqueous HCL (ice cold), then aqueous saturated NaHCO₃. It was then dried with MgSO₄, filtered and concentrated to give monomer (I) as a white solid (207 g). The product was dissolved in dry toluene and concentrated to dryness before use in a glycosylation reaction. The 207 g of monomer (I) product recovered was essentially equal to the theoretical yield, calculated to be 203.4 g.

¹H-NMR (CD₂Cl₂) δ: 8.16-7.41 (benzoate hydrogens, phthalimido hydrogens), 7.30 & 6.95 (S-aromatic hydrogens), 5.97 (H-3), 5.82 (H-1), 4.89 & 4.49 (H-6), 4.40 (H-2), 4.14 (H-4), 4.01 (H-5), 2.30 (S-Ph-Me group), 0.80 (t-butyl group on silicon), 0.09& −0.16 (methyl groups of silicon). Thus the NMR spectrum verified the structure of Monomer (I), as shown above.

Example 3

Synthesis of Monomer (II)

Preparation of Monomer (I)

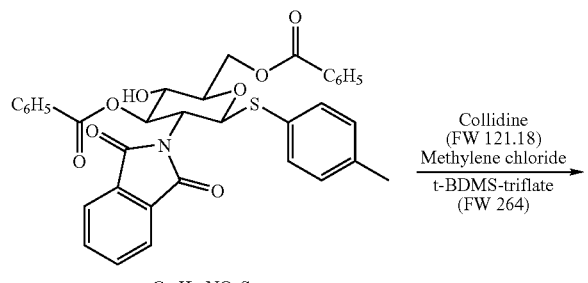

C₃₅H₂₉NO₈S
Mol. Wt.: 623.67
Product 6,

Preparation of intermediate compound 7

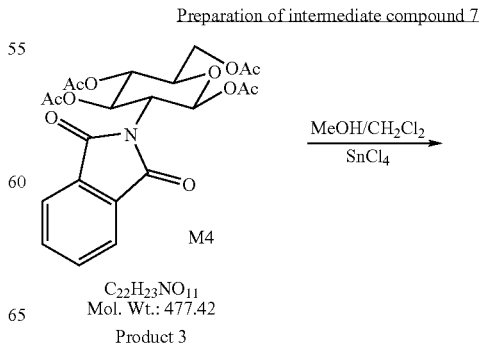

C₂₂H₂₃NO₁₁
Mol. Wt.: 477.42
Product 3

-continued

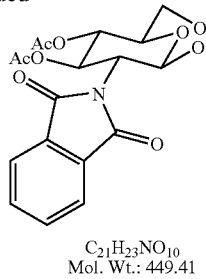

C$_{21}$H$_{23}$NO$_{10}$
Mol. Wt.: 449.41
Product 7

To ensure that the starting glycoside was free of EtOH traces, compound 3 (60.0 g; 126 mmol) was dissolved in toluene and evaporated. It was then dissolved in anhydrous CH$_2$Cl$_2$ (500 ml) containing MeOH (6.5 g; 202 mmol; 1.6 eq.). Tin tetrachloride (SnCl$_4$; 18.4 g; 70.5 mmol; 0.56 eq.) was diluted with CH$_2$Cl$_2$ (25 ml) and added drop-wise. The reaction mixture was poured over ice water and shaken well. This was repeated once more and then the organic layer was washed twice with aqueous saturated NaHCO$_3$, dried with MgSO$_4$, filtered, and concentrated. The crude product was recrystallized from hot EtOH, giving crystals of product 7(43.1 g). The crude yield of 49.8 g of product 7 was 88% of the theoretical yield, calculated to be 56.6 g, while the recrystallized product 7 yield of 43.1 g was 76%.

$^1$H-NMR (CD$_2$Cl$_2$) δ: 7.86-7.74 (phthalimido hydrogens), 5.78 (H-3), 5.31 (H-1), 5.18 (H-4), 4.31 (H-2), 4.34 & 4.20 (H-6), 3.88 (H-5), 2.20, 2.03, 1.86 (methyls of acetyl groups). Thus the NMR spectrum verified the structure of product 7, as shown above.

Preparation of intermediate product 8

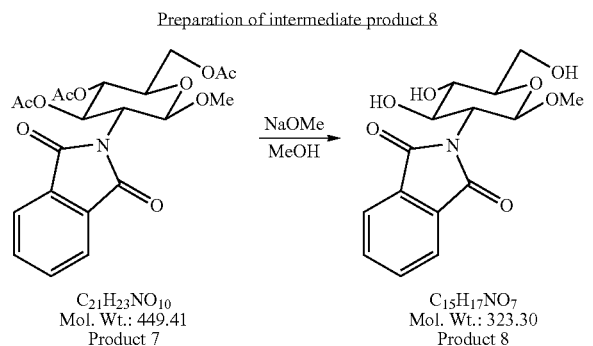

C$_{21}$H$_{23}$NO$_{10}$
Mol. Wt.: 449.41
Product 7

C$_{15}$H$_{17}$NO$_7$
Mol. Wt.: 323.30
Product 8

Product 7 (141.0 g; 314 mmol) was suspended in MeOH (1000 ml), and NaOMe (0.5 M, 10 ml) was added. The methyl glycoside product 7 did not readily dissolve in MeOH. The solution was tested to ensure basicity. The reaction was stirred overnight. The solution became clear. Examination of the reaction mixture by TLC (EtOAc—Hexane-EtOH=10:20:1) indicated the disappearance of the starting material and the formation of a polar product (near the origin). The solution was neutralized with sulfonic acid resin, filtered, and concentrated to dryness. Weight of the residue, called product 8, was 105.3 g, which probably includes some methanol.

The crude yield of 105.3 g of product 8 was essentially equal to the theoretical yield, calculated to be 101.3 g. $^1$H-NMR (CD$_3$OD) δ: 7.85-7.80 (phthalimido hydrogens), 5.07 (H-1), 4.21 (H-2), 3.94 (H-3), 3.92 & 3.74 (H-6), 3.40 (H-5), 3.40 (OCH$_3$), 3.38 (H-4). Thus the NMR spectrum verified the structure of product 8, as shown above.

Preparation of Monomer (II)

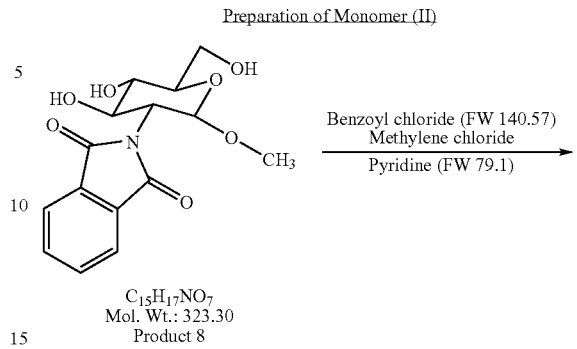

C$_{15}$H$_{17}$NO$_7$
Mol. Wt.: 323.30
Product 8

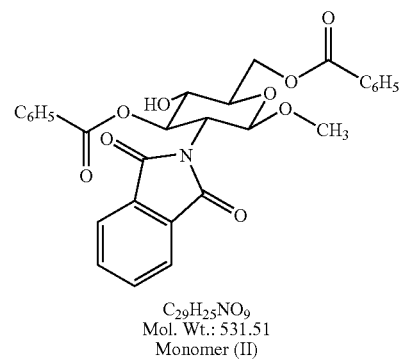

C$_{29}$H$_{25}$NO$_9$
Mol. Wt.: 531.51
Monomer (II)

Product 8 (crude; 105.3), after being evaporated with toluene-DMF, was suspended in CH$_2$Cl$_2$ (500 ml). Pyridine (61.8 g; 782 mmol; 2.5 eq.) was added first, followed by the drop-wise addition of benzoyl chloride (88 g; 626 mmol; 2.0 eq.) to the mixture. The reaction mixture was allowed to stir at room temperature for 24 h. It was then diluted with CH$_2$Cl$_2$ and washed sequentially with H$_2$O, 1 M HCl (2×), then aqueous saturated sodium bicarbonate solution, dried with MgSO$_4$, filtered, and concentrated. The product was purified by chromatography on silica gel, using EtOAc—Hexane=3:8 as eluant. The weight of the purified product was 116.1 g. The product was about 90% pure as determined by NMR. A portion (21.1 g) of this product was crystallized from dietylether-hexane to obtain pure crystalline material (13.8 g) of monomer (II).

$^1$H-NMR (CD$_2$Cl$_2$) δ: 8.15, 7.92, 7.67, 7.56, 7.42 (benzoate hydrogens), 7.83-7.74 (phthalimido hydrogens), 5.93 (H-3), 5.40 (H-1), 4.82 & 4.72 (H-6), 4.43 (H-2), 4.03-3.92 (H-5, H-4), 3.50 (OCH$_3$), 3.33 (OH). Thus the NMR spectrum verified the structure of monomer (II), as shown above.

Example 4

Synthesis of Derivatized Glucosamine Disaccharide

Structural Characterization of Oligoglucosamine Derivatives:

The structures of the coupled products described below were confirmed by proton NMR and mass spectrometry as follows. The chemical shifts of hydrogens H-3 and H-1 of the phthalimido glucosamine unit appeared in proton NMR spectrum at chemical shifts between 5 and 6.5 ppm. The hydrogen H-3 appeared as a doublet of a doublet with a coupling constant of about 8-10 Hz. By counting the number of these hydrogen signals, the length of the oligoglucosamine can easily be determined, for the disaccharide to the pentasaccharide. For oligoglucosamine derivatives of 6 and above, the signals for these hydrogens started to overlap. However, a sufficient number of these signals could be identified to confirm the structure. A similar observation was seen for the anomeric hydrogens, which appeared as a doublet with a coupling constant of about 8-8.5 Hz, thereby confirming the β-glycosidic configuration. Furthermore, the chemical shift of H-4 in the terminal glucosamine unit appeared around 3.5 ppm, when the corresponding carbon carried a hydroxyl group. This was shifted to 3.7 ppm upon glycosylation at this site. Thus, H-4 could be used as a reporter group for establishing the success of the glycosylation reaction. Further proof of structure was obtained by MALDI and electrospray mass spectral data of the product, which are indicated for each compound.

additional 100 ml of the triflic acid/lmethyltriflate solution was added to the reaction mixture dropwise to reduce of the viscosity. The reaction mixture was filtered cold over a celite pad into a filter flask containing 1:1 saturated sodium thiosulfate-sodium bicarbonate solution that was stirred thoroughly during the filtration. The flask and the residue on the filter were rinsed with methylenechloride and the combined filtrate was worked up as follows. The filtrate was poured into a separatory funnel. The contents were thoroughly mixed, the aqueous solution separated, and the organic layer washed one more time with saturated aqueous sodium thiosulfate solution, followed by water, and aqueous saturated sodium bicarbonate solution. The solution was then dried with magnesium

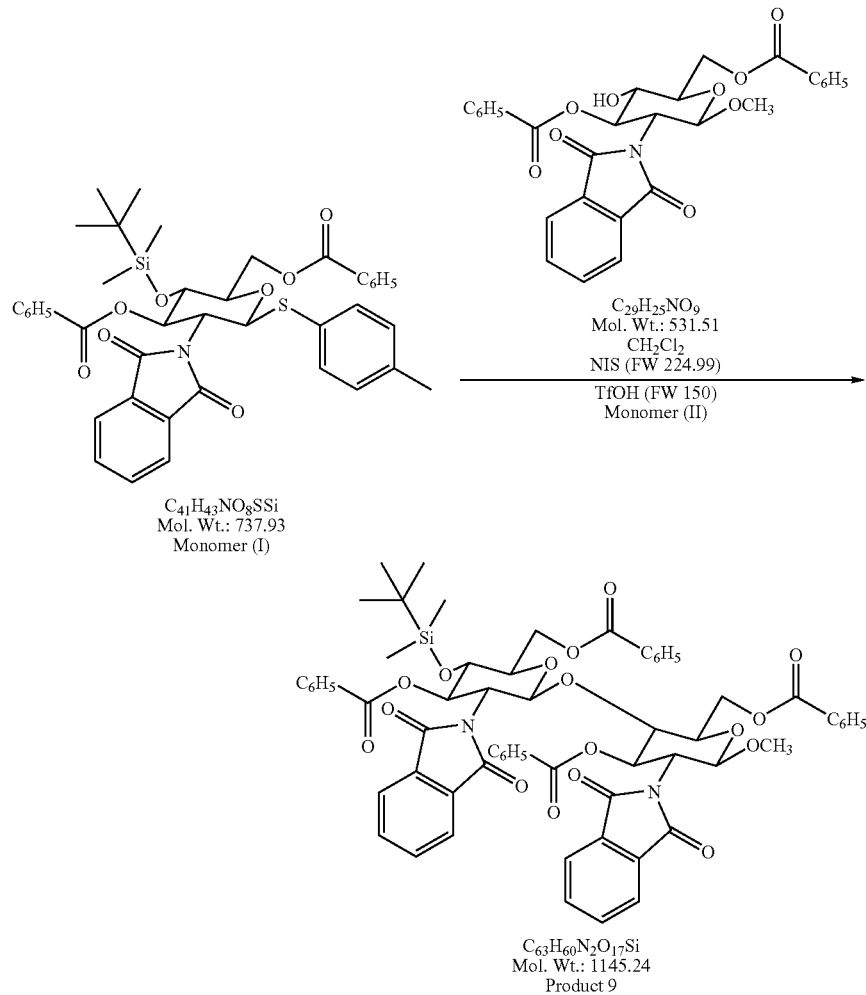

Synthesis of Dimer Product 9

Monomer (II) (80.6 g, 109.3 mmol, 1.2 eq.) and monomer (II) (48.4 g, 91.1 mmol), both previously evaporated with toluene once, were dissolved in $CH_2Cl_2$ (150 mL) in a 3-necked, 500 ml flask. 4A Molecular sieve was added (5 g). The mixture was cooled to −60° C. under nitrogen atmosphere with vigorous stirring. After 10 min, N-Iodosuccinimide (NIS; 44.3 g; 196.7 mmol; 2.2 eq.) was added as a dry powder, followed by the drop-wise addition of a solution of triflic acid (TfOH; 13.7 g, 91.1 mmol, 1.0 eq.) and methyltriflate (14.9 g, 54.8 mmol, 1.0 eq.) in methylenechloride. The reaction mixture was left at −55° C. for an additional 4 hr. An sulfate, filtered and concentrated. Weight of the crude product was 111.1 g. Analytically pure sample was prepared by subjecting the crude product to separation by silica gel chromatography, using ethyl acetate-hexane as eluant. 1H-NMR ($CD_2Cl_2$) δ: 8.17-7.19 (phthalimido and benzoate hydrogens), 6.11 and 5.76 (2×H-3), 5.74 and 5.31 (2×H-1), 4.36 and 4.32 (2×H-2), 4.32 and 3.93 (2×H-4), 3.90 and 3.53 (2×H-5), 4.65, 4.38, 4.12, and 3.63 (4×H-6), 3.38 ($OCH_3$), 0.68 (t-butyl), −0.12, −0.40 (2×$CH_3$). Mass spec.: M. wt. Calc. 1144.37; Obs. M+Na=1167.5. Thus the NMR spectrum verified the structure of product 9, as shown above. The crude product as such was used in the next step, where complete removal of the tBDMS was accomplished.

Example 5

Removal of the Silicon Group from Disaccharide Product 9 for Chain Extension Preparation of intermediate product 10

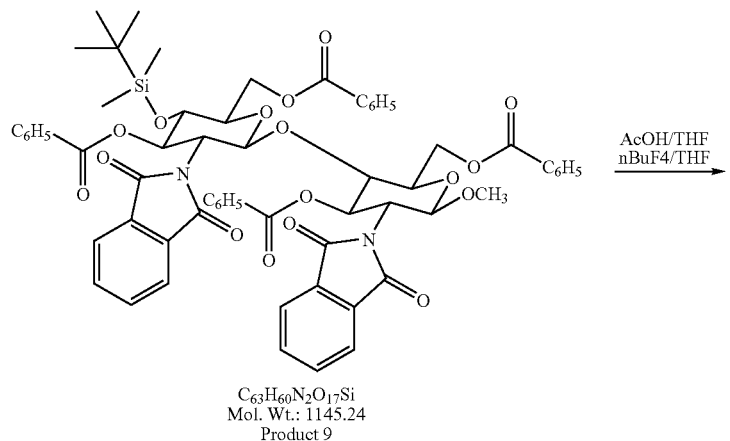

$C_{63}H_{60}N_2O_{17}Si$
Mol. Wt.: 1145.24
Product 9

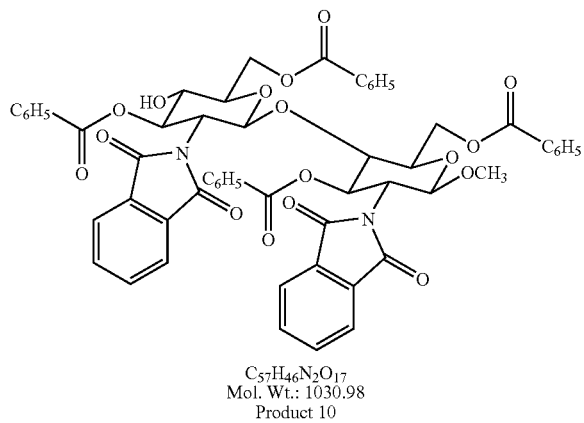

$C_{57}H_{46}N_2O_{17}$
Mol. Wt.: 1030.98
Product 10

Product 9 (111.1 g) was dissolved in THF (350 ml). To this solution, a 1 M solution of acetic acid (110 ml) and a 1 M solution of n-tetrabutylammonium fluoride in THF (110 ml) were added and the reaction mixture was stirred at room temperature for 3 days. Completion of the reaction was ascertained by TLC using EtOAC:Hex:EtOH=4:8:1 as a solvent, which indicated that the reaction was complete. The solvent of the reaction was evaporated on high vacuum (without heat) and the residue was dissolved in $CH_2Cl_2$, washed sequentially with water, 1 M aqueous HCl, 10% sodium thiosulfate aqueous solution, and finally, with saturated aqueous $NaHCO_3$. The solution was then dried with $MgSO_4$, filtered and concentrated. The resulting soild was treated with diethylether, which resulted in a gluey material. The supernatent was filtered and the gluey material was repeatedly washed with diethylether. To the filtrate, hexane was added to precipitate any ether soluble product and this was filtered (Fraction B, 5.9 g). The final filtrate from ether-hexane was concentrated to dryness (Fraction C).

The NMR spectrum indicated that Fraction B product had about 5% silicon impurity (peak around 0 ppm) along with the major desired disaccharide. Fraction A was contaminated about 10% with tBDMS impurities and a tetrabutylammonium derivative. Therefore, Fraction A was resuspended in 600 ml of ether, mixed for about 10 minutes, filtered and the process was repeated once more (weight of the solid recovered was 77.3 g). This solid was purified once more by dissolving the product in ethyl acetate and precipitating the product with the aid of hexane (weight of the product recovered was 71.7 g). The filtrates were combined, hexane was added to precipitate the remaining product and additional 10.8 g of the product was recovered. $^1$H-NMR ($CD_2Cl_2$) δ: 8.12-7.14 (phthalimido and benzoate hydrogens), 6.14 and 5.73 (2×H-3), 5.72 and 5.34 (2×H-1), 4.37 and 4.34 (2×H-2), 4.10 and 3.69 (2×H-4), 3.97 and 3.44 (2×H-5), 4.66, 4.18, 4.12-4.06 (4×H-6), 3.38 ($OCH_3$), 3.35 (OH). Mass spec.: M. wt. Calc. 1030.98; Obs. M+Na=1053.1. Thus the NMR spectrum verified the structure of product 10, as shown above.

Example 6

Synthesis of Derivatized Glucosamine Trisaccharide

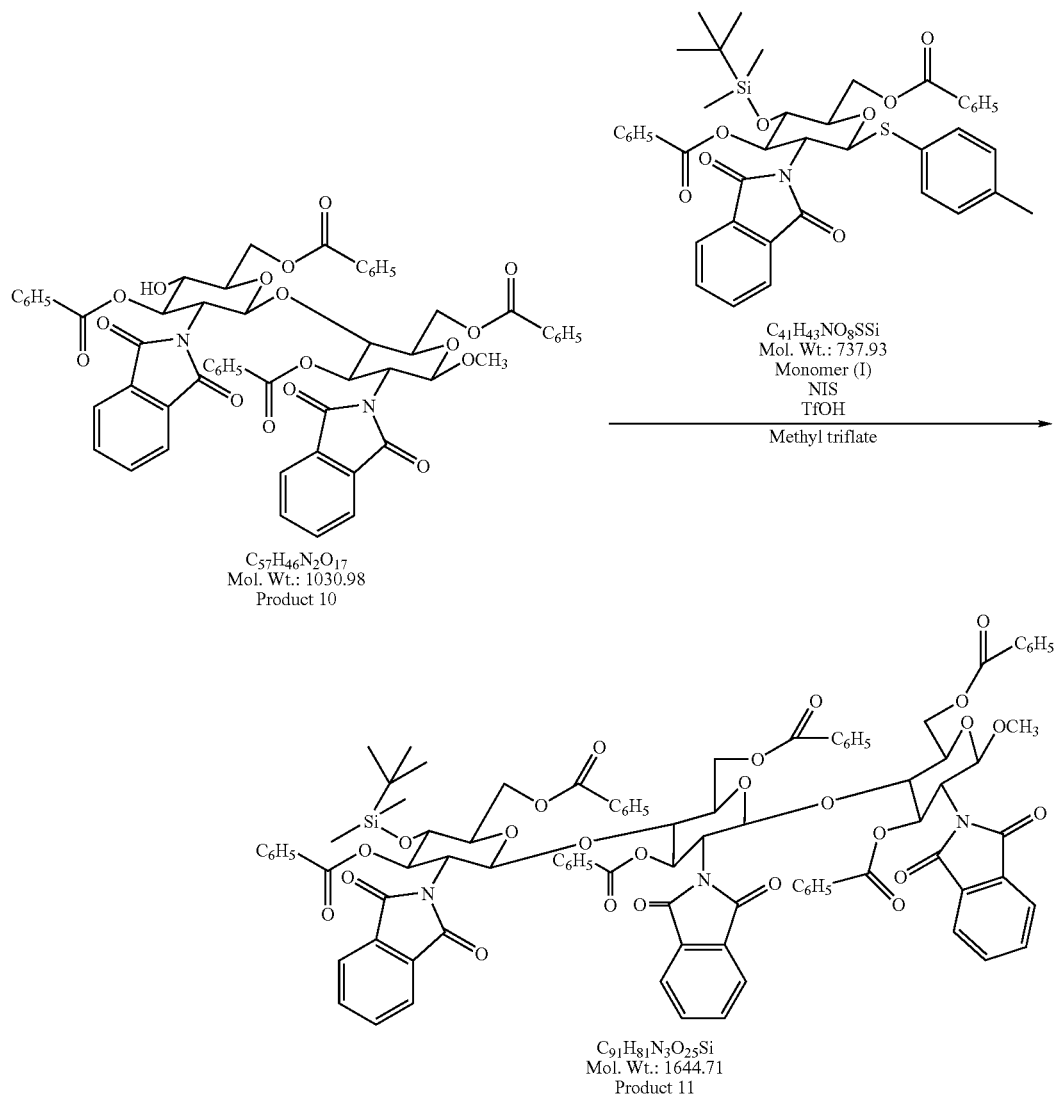

Synthesis of Trimer product 11

Monomer (I) (88.6 g; 120 mmol; 1.5 eq.) and product 10 (82.5 G; 80.0 mmol) were dissolved in $CH_2Cl_2$ (100 ml) in a flask. Molecular sieve (4A, 5.0 g) was added. The flask was placed in a −55° C. water bath and stirred for 15 min. NIS (48.6 g; 216 mmol) was added as a powder to the cold solution, while maintaining vigorous stirring. A solution of methyl triflate (13.1 g; 80 mmol; 1.0 eq.) and TfOH (12 g; 80 mmol; 1.9 eq.), both dissolved together in $CH_2Cl_2$ (5 ml), was added to the cold solution in drops by means of an addition funnel (over 60 min). After 6 h at −60° C. to −50° C., the reaction mixture was poured over saturated sodium bicarbonate and saturated sodium thiosulfate aqueous solution (1:1, 400 ml) contained in an Erlenmeyer flask and thoroughly stirred. Additional methylenechloride (200 ml) was added and the contents were thoroughly mixed for 10 min, the aqueous solution separated, and the organic layer washed with 0.6% aqueous bleach solution, de-ionized water, and aqueous saturated sodium bicarbonate solution. The solution was then dried with $MgSO_4$, filtered and concentrated.

To remove the excess monomer impurity from the trisaccharide, the crude product was suspended in diethylether (600 ml), the solid thoroughly mixed and the supernatent filtered. This process was repeated three times and the residue finally dissolved in methylenechloride, then concentrated to dryness giving 93.5 g of product 11. To the filtrate, about 40% volume of hexane was added and the precipitated material filtered, redissolved in methylenechloride and concentrated to dryness under vacuum to obtain an additional amount of compound 11 (26.0 g). $^1$H-NMR ($CD_2Cl_2$) δ(only select hydrogen chemical shifts are reported): 8.13-7.12 (phthalimido and benzoate hydrogens), 6.03, 5.88, and 5.62 (3×H-3), 5.64, 5.48, and 5.29 (3×H-1), 3.77 (H-4 of the terminal glucosamine unit), 3.90 (H-5 of the terminal glucosamine unit), 4.63 (H-6 of the terminal glucosamine unit), 3.35 ($OCH_3$), 0.64 (t-butyl), −0.18, −0.33 (2×$CH_3$ of the silicon unit). Mass spec.: Exact m. wt. Calc. 1643.49; Obs. M+Na=1666.3. Thus the NMR spectrum verified the structure of product 11, as shown above.

Example 7

Removal of the Silicon Group from Trisaccharide Product 11 for Further Chain Extension

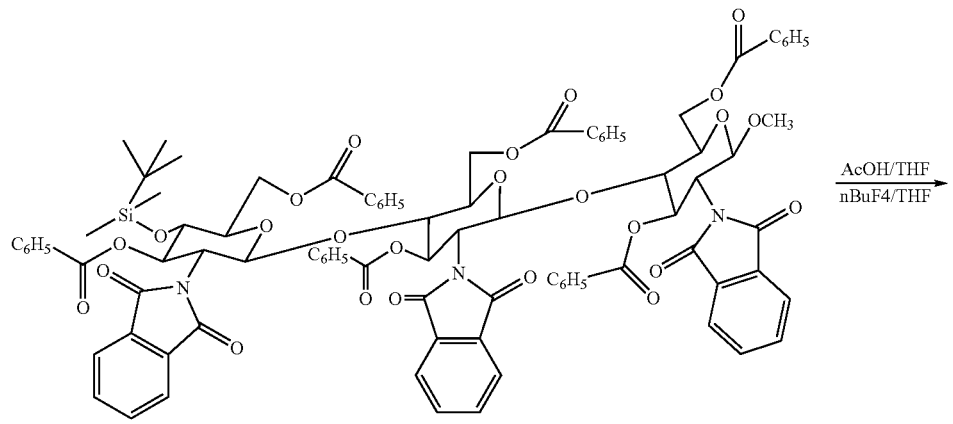

Preparation of intermediate 12

$C_{91}H_{81}N_3O_{25}Si$
Mol. Wt.: 1644.71
Product 11

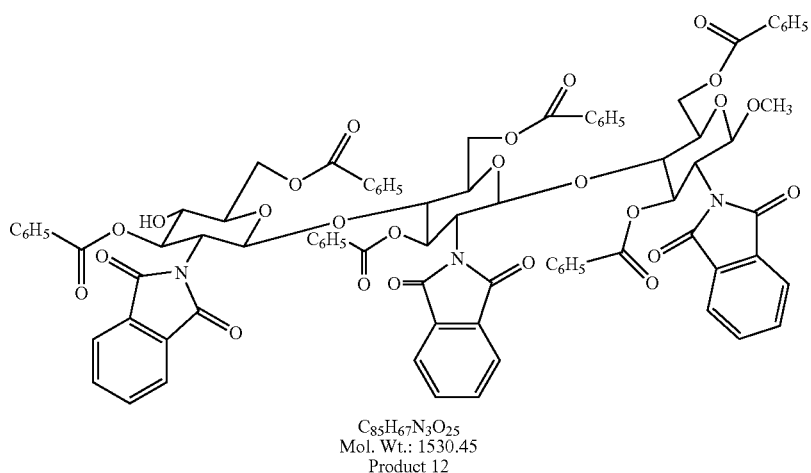

$C_{85}H_{67}N_3O_{25}$
Mol. Wt.: 1530.45
Product 12

Product 11 was dissolved in minimum THF (500 ml). To this solution, 1 M solution of acetic acid (150 ml) and a 1 M solution of n-tetrabutylammonium fluoride in THF (150 ml) were added and the reaction mixture was stirred at room temperature for 3 days. The reaction mixture was evaporated to dryness, the residue redissolved in methylenechloride, washed sequentially with deionized water, 1 M HCl, 1% aqueous bleach solution (to remove the dark brown color), and saturated sodium bicarbonate solution, then concentrated to dryness.

In order to remove the nonpolar silicon and other impurities, the solid was dissolved in minimum ethyl acetate. Hexane was added in drops (the final solvent ratio EtOAc—Hexane was 17:14). This resulted in a gluey material. The liquid was filtered and the gluey material redissolved in EtOAc (200 ml) and precipitated with hexane (100 ml) as described above. Finally, diethylether was added to solidify the gluey material and the solid was filtered. The solid was redissolved in methylenechloride and concentrated to dryness giving 81.4 g of product 12.

The filtrate EtOAc—Hexane-ether was concentrated to dryness. The residue was suspended in diethylether, shaken well and filtered. This process was repeated twice. Finally, the precipitate was dissolved in methylenechloride and concentrated to dryness to obtain additional product 12 (16.5 g).).
$^1$H-NMR ($CD_2Cl_2$) δ (only select hydrogen chemical shifts are reported): 8.08-7.16 (phthalimido and benzoate hydrogens), 6.03, 5.92, and 5.59 (3×H-3), 5.67, 5.48, and 5.29 (3×H-1), 3.56 (H-4 of the terminal glucosamine unit), 3.91 (H-5 of the terminal glucosamine unit), 4.63 (H-6 of the terminal glucosamine unit), 3.35 ($OCH_3$), 3.01 (OH), 0.64. Mass spec: Exact m. wt. Calc. 1529.41; Obs. M+Na=1553.4. Thus the NMR spectrum verified the structure of product 12, as shown above.

Example 8

Synthesis of Derivatized Glucosamine Tetrasaccharide

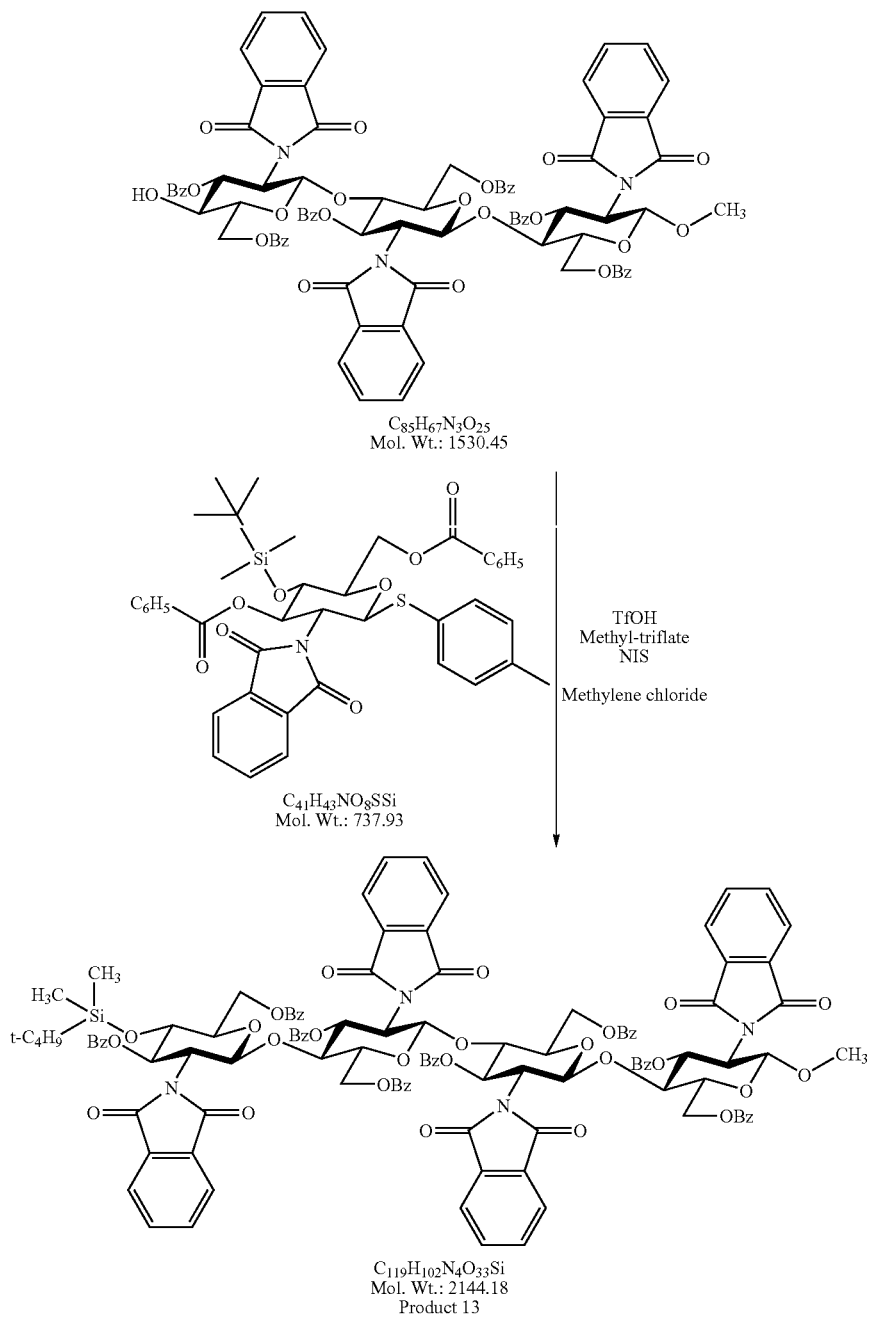

Thioglycoside monomer (I) (37.4 g; 50.7 mmol) and trisaccharide product 12 (45.6 g; 29.8 mmol) were dissolved in $CH_2Cl_2$ (150 ml) in a flask. Molecular sieve (4A, 10.0 g) was added. The flask was placed in a −55° C. bath and stirred for 15 min. NIS (20.5 g; 91.25 mmol) was added as a powder to the cold solution, while maintaining vigorous stirring. A solution of methyl triflate (4.9 g; 29.8 mmol) and TfOH (4.5 g; 29.8 mmol), both dissolved together in $CH_2Cl_2$ (20 ml), was added to the cold solution in drops by means of an addition funnel (over 60 min). After 6 h, at −60° C., the reaction mixture was poured over saturated sodium bicarbonate and saturated sodium thiosulfate aqueous solution (1:1, 400 mL) contained in an Erlenmeyer flask and thoroughly stirred. Additional methylenechloride (200 ml) was added and the contents were thoroughly mixed for 10 min, the aqueous solution separated, and the organic layer washed sequentially with 10% aqueous sodium thiosulfate solution, 1% aqueous bleach solution, and aqueous saturated sodium bicarbonate solution. The solution was then dried with MgSO$_4$, filtered and concentrated (75.1 g).

To remove the excess monomer impurity from the tetrasaccharide, the crude product was suspended in diethylether (600 ml), the solid thoroughly mixed and the supernatent filtered. This process was repeated three times, and the residue finally dissolved in mehtylenechloride and concentrated to dryness (13 A, 54.2 g).

To the filtrate, about 40% volume of hexane was added and the precipitated material filtered, redissolved in methylenechloride and concentrated to dryness giving 5.8 g of product 13 B. NMR analysis of 13 A and 13 B indicated that these were nearly the same and they were combined. $^1$H-NMR (CD$_2$Cl$_2$) δ (only select hydrogen chemical shifts are reported): 8.09-7.03 (phthalimido and benzoate hydrogens), 6.00, 5.83, 5.76, and 5.62 (4×H-3), 5.62, 5.42, 5.41, and 5.27 (4×H-1), 3.74 (H-4 of the terminal glucosamine unit), 3.88 (H-5 of the terminal glucosamine unit), 4.60 (H-6 of the terminal glucosamine unit), 3.33 (OCH$_3$), 0.63 (t-butyl), −0.19, −0.34 (2×CH$_3$ of the silicon unit). Mass spec.: Exact m. wt. Calc. 2142.62; Obs. M+Na=2166.4. Thus the NMR spectrum verified the structure of product 13, as shown above.

Example 9

Removal of the Silicon Group from Tetrasaccharide Product 13 for Further Chain Extension

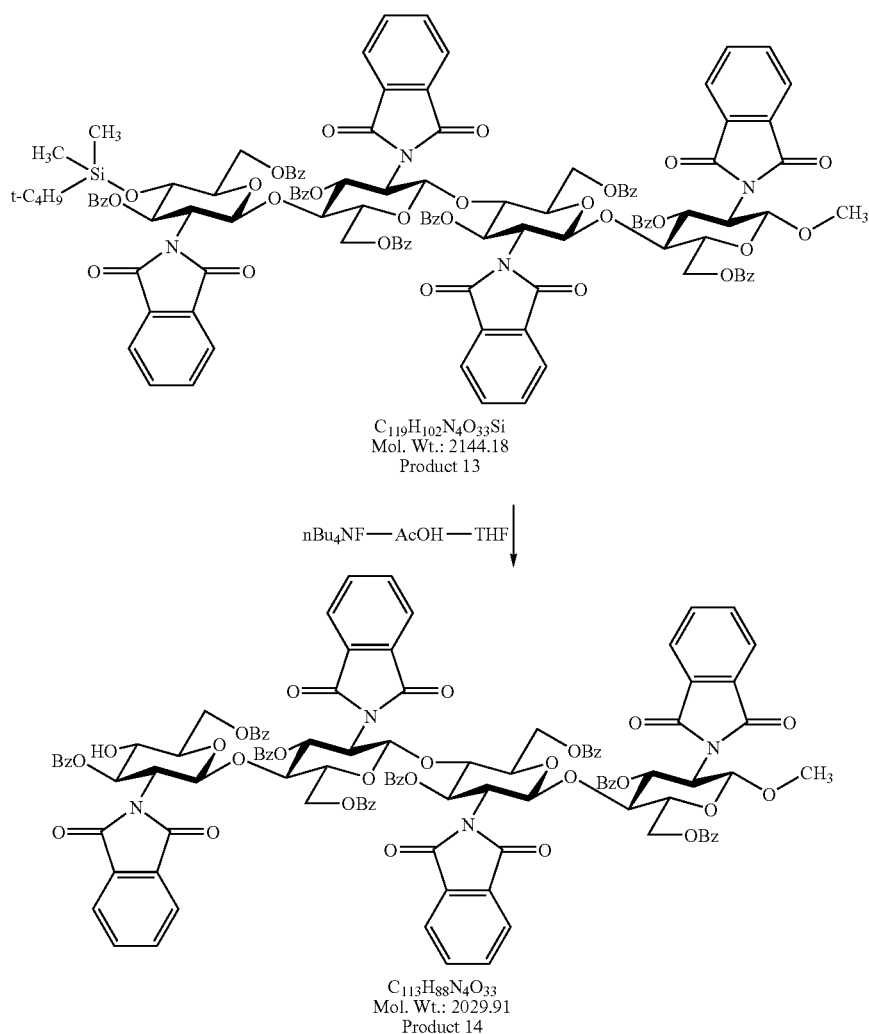

Tetrasaccharide product 13 (60 g) was dissolved in minimum THF. This was followed with the addition of a solution of 1 M acetic acid in THF (60 ml) and a 1 M solution of tetrabutylammonium fluoride in THF (60 ml) and stirred at room temperature for 48 h. The reaction mixture was evaporated to dryness, redissolved in methylenechloride, washed sequentially with deionized water, 1 M HCl, 1% aqueous bleach solution (to remove the dark brown color), saturated sodium thiosulfate solution, and saturated sodium bicarbonate solution, then concentrated to dryness giving 56.5 g of material.

To remove nonpolar silicon impurities, the solid was dissolved in ethylacetate (170 ml) and hexane was added slowly in drops (the solvent ratio EtOAc—Hexane was 1:1). This resulted in a gluey material. The liquid was filtered and the gluey material was re-dissolved in EtOAc (150 ml), then precipitated with hexane (150 ml) as described above. The supernatent was filtered. Finally, diethylether was added to solidify the gluey material and the solid filtered. The solid was redissolved in methylenechloride and concentrated to dryness giving 50.8 g of product 14. $^1$H-NMR (CD$_2$Cl$_2$) δ (only select hydrogen chemical shifts are reported): 8.04-7.06 (phthalimido and benzoate hydrogens), 6.00, 5.82, 5.79, and 5.55 (4×H-3), 5.62, 5.44, 5.39, and 5.26 (4×H-1), 3.52 (H-4 of the terminal glucosamine unit), 3.87 (H-5 of the terminal glucosamine unit), 4.59 (H-6 of the terminal glucosamine unit), 3.33 (OCH$_3$). Mass spec.: Exact m. wt. Calc. 2028.53; Obs. M+Na=2052.3. Thus the NMR spectrum verified the structure of product 14, as shown above.

Example 10

Synthesis of Derivatized Glucosamine Pentasaccharide

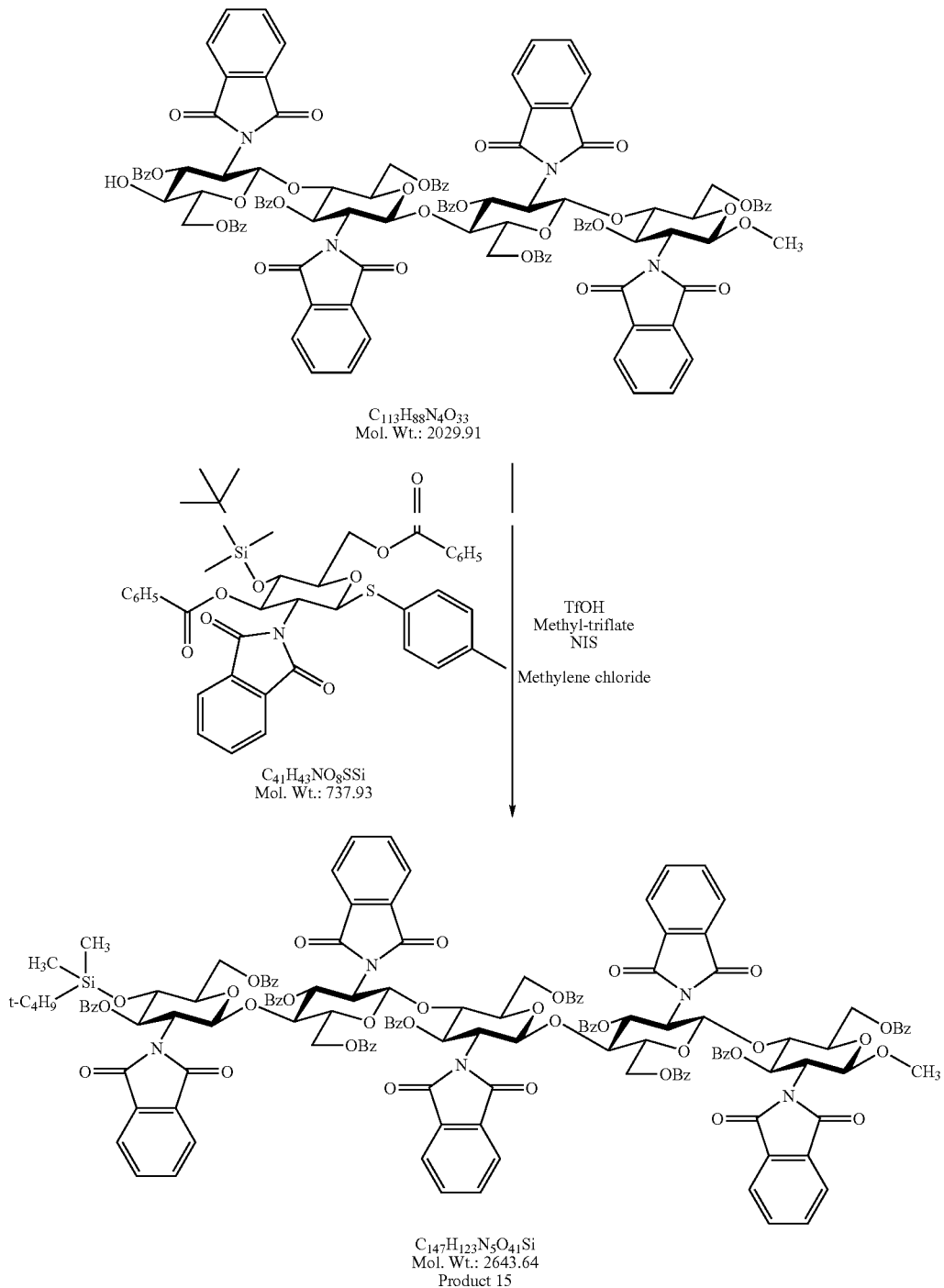

Synthesis of Pentamer Product 15

Product 15

Thioglycoside monomer (I) (82.4 g; 111.6 mmol) and tetrasaccharide product 14 (113.3 g, 55.8 mmol) were dissolved in minimum $CH_2Cl_2$ (200 ml) in a flask. 4A Molecular sieves (15 g) were added. The flask was placed in a −60° C. bath and stirred for 10 min. NIS (45.2 g; 200.9 mmol) was added as a powder. A solution of methyl triflate (9.2 g; 55.8 mmol) and TfOH (8.4 g; 55.8 mmol, dissolved together in $CH_2Cl_2$ (20 ml), was added slowly via an addition funnel. After 6 h at −60° C., the reaction mixture was diluted with another 50 ml of $CH_2Cl_2$ and then worked up as follows.

The reaction mixture was poured over saturated sodium bicarbonate and saturated sodium thiosulfate aqueous solution (1:1, 500 ml) contained in an Erlenmeyer flask and thoroughly stirred. Additional methylenechloride (400 ml) was added and the contents were thoroughly mixed for 10 min, the aqueous solution separated, and the organic layer washed sequentially with 1% aqueous bleach solution, 10% aqueous sodium thiosulfate solution, and aqueous saturated sodium bicarbonate solution. The solution was then dried with $MgSO_4$, filtered and concentrated giving 171.5 g of material.

In order to remove the by-products, the crude product was dissolved in EtOAc (300 ml) and hexane (300 ml) was slowly added. This resulted in a gluey material. The supernatent was decanted and the procedure was repeated once more with EtOAc and hexane. Upon addition of diethylether (600 ml), the gluey material became a solid. The suspension was stirred at room temperature for 30 min. The solution was filtered and the process was repeated once more and the resulting solid was filtered and dried giving 131.7 g of product 15. $^1$H-NMR ($CD_2Cl_2$) 6 (only select hydrogen chemical shifts are reported): 8.08-7.02 (phthalimido and benzoate hydrogens), 5.99, 5.79, 5.72, 5.69, and 5.58 (5 ×H-3), 5.60, 5.39, 5.37, 5.32, and 5.26 (5×H-1), 3.73 (H-4 of the terminal glucosamine unit), 3.86 (H-5 of the terminal glucosamine unit), 4.58 (H-6 of the terminal glucosamine unit), 3.32 ($OCH_3$), 0.63 (t-butyl), −0.20, −0.36 (2×$CH_3$ of the silicon unit). MALDI data.: m/e calc. 2642.75 (100%); Obs. M+Na=2666.0. Thus the NMR and MALDI spectra verified the structure of product 15, as shown above.

Example 11

Removal of the Silicon Group from Tetrasaccharide Product 15 for Further Chain Extension

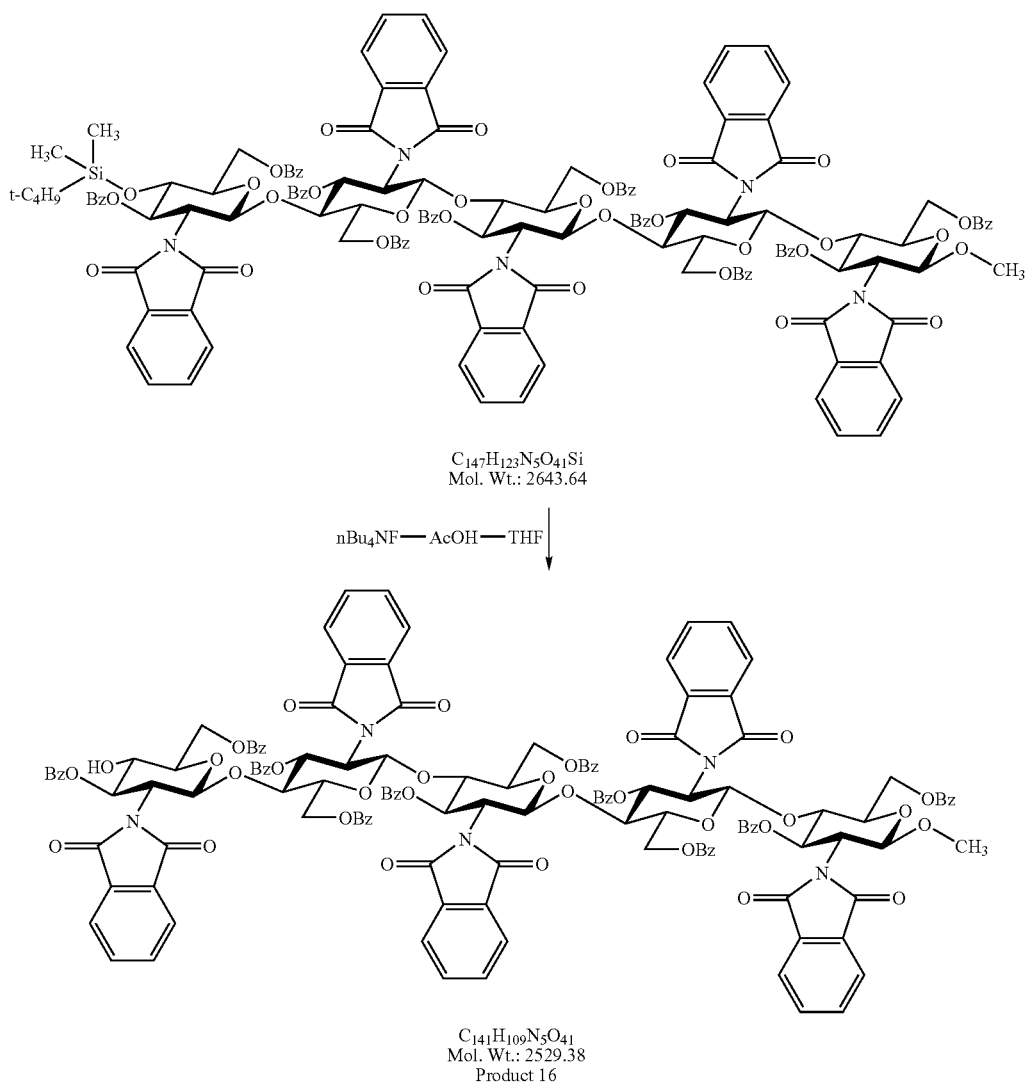

Purified pentasaccharide (111.7 g, 42.3 mmol) was dissolved in minimum THF followed by the addition (85 ml each) of 1 M solution of acetic acid in THF and 1 M solution of tetrabutylammoniumfluoride in THF and stirred at room temperature. Reaction progress was checked after 18 h by NMR, which indicated that the reaction was complete. The reaction mixture was evaporated to dryness, redissolved in methylenechloride, washed sequentially with saturated sodium thiosulfate solution, 1 M HCl, and saturated sodium bicarbonate solution, and then concentrated to dryness.

To remove nonpolar silicon impurities, the solid was dissolved in ethyl acetate (400 ml). Hexane (400 ml) was added in drops with stirring of the precipitated material. The precipitated solid became a gluey material during the course of the addition and became a solid at the end of the addition. The precipitate was filtered and the process was repeated once more, followed by a final washing of the solid with 1:1 EtOAc—Hexane and then dried giving 100.7 g of product 16. $^1$H-NMR (CD$_2$Cl$_2$) δ (only select hydrogen chemical shifts are reported): 8.04-7.03 (phthalimido and benzoate hydrogens), 5.98, 5.79, 5.75, 5.69, and 5.54 (5×H-3), 5.60, 5.39, 5.37, 5.35, and 5.25 (5×H-1), 3.51 (H-4 of the terminal glucosamine unit), 4.56 (H-6 of the terminal glucosamine unit), 3.32 (OCH$_3$). MALDI data.: m/e calc. 2528.66 (100%); Obs. M+Na=2550.8. Thus the NMR and MALDI spectra verified the structure of product 16, as shown above.

Example 12

Synthesis of Derivatized Glucosamine Hexasaccharide

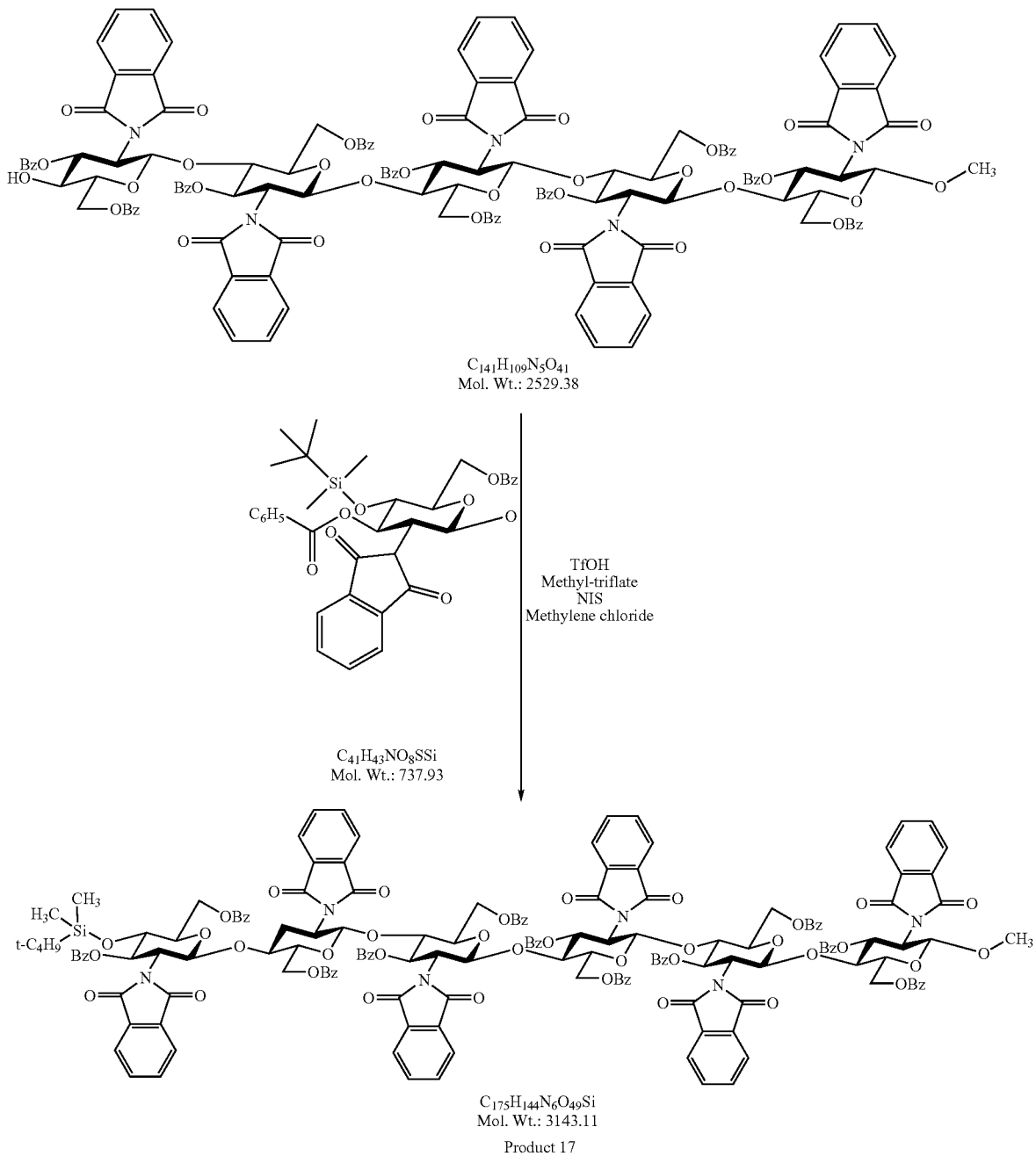

Product 17

Thioglycoside monomer (I) (52.5 g; 71.2 mmol) and pentasaccharide product 16 (90.0 g; 35.6 mmol) were dissolved in CH$_2$Cl$_2$ (150 ml) in a 3-necked, 500 ml RB. 4A Molecular sieves (5 g) were added. The solution was cooled to −60° C. and stirred well. After ten minutes at −60° C., NIS (28.8 g; 128.1 mmol) was added quickly. After five minutes, a solution of triflic acid (5.3 g; 35.6 mmol) and methyl triflate (5.8 g; 35.6 mmol), dissolved together in CH$_2$Cl$_2$ (20 ml), was added in drops (over 40 minutes). The reaction mixture was left at −60° C. for an additional 5 hr. An additional 100 ml of the triflic acid/methyl triflate solution was added to the reaction mixture dropwise to reduce of the viscosity and then worked up as follows.

The reaction mixture was poured over saturated sodium bicarbonate and saturated sodium thiosulfate aqueous solution (1:1, 500 ml) contained in an Erlenmeyer flask and thoroughly stirred. Additional methylenechloride (400 ml) was added and the contents were thoroughly mixed for 10 min, the aqueous solution separated, and the organic layer washed sequentially with 1% aqueous bleach solution, 10% aqueous sodium thiosulfate solution, and aqueous saturated sodium bicarbonate solution. The solution was then dried with MgSO$_4$, filtered and concentrated. The residual solid was dissolved in EtOAc (400 ml), followed by the slow addition of hexane (400 ml). This resulted in a gluey material. The liquid portion was filtered, and the gluey material redissolved in EtOAc, then precipitated again in hexane. Finally, diethylether was added to solidify the gluey material, and the residue was washed with ether and dried giving 96.3 g of product 17. $^1$H-NMR (CD$_2$Cl$_2$) δ (only select hydrogen chemical shifts are reported): 8.08-7.02 (phthalimido and benzoate hydrogens), 5.98, 5.77, 5.70, 5.66, 5.66, and 5.58 (6×H-3), 5.59, 5.30, 5.25 (H-1s), 3.72 (H-4 of the terminal glucosamine unit), 4.57 (H-6 of the reducing end glucosamine unit), 3.32 (OCH$_3$), 0.62 (t-butyl), −0.21, −0.36 (2×CH$_3$ of the silicon unit). MALDI data.: m/e calc. 3142.88 (100%); Obs. M+Na=3165.3. Thus the NMR and MALDI spectra verified the structure of product 17, as shown above.

Example 13

Removal of the Silicon Group from Hexasaccharide Product 17 for Further Chain Extension

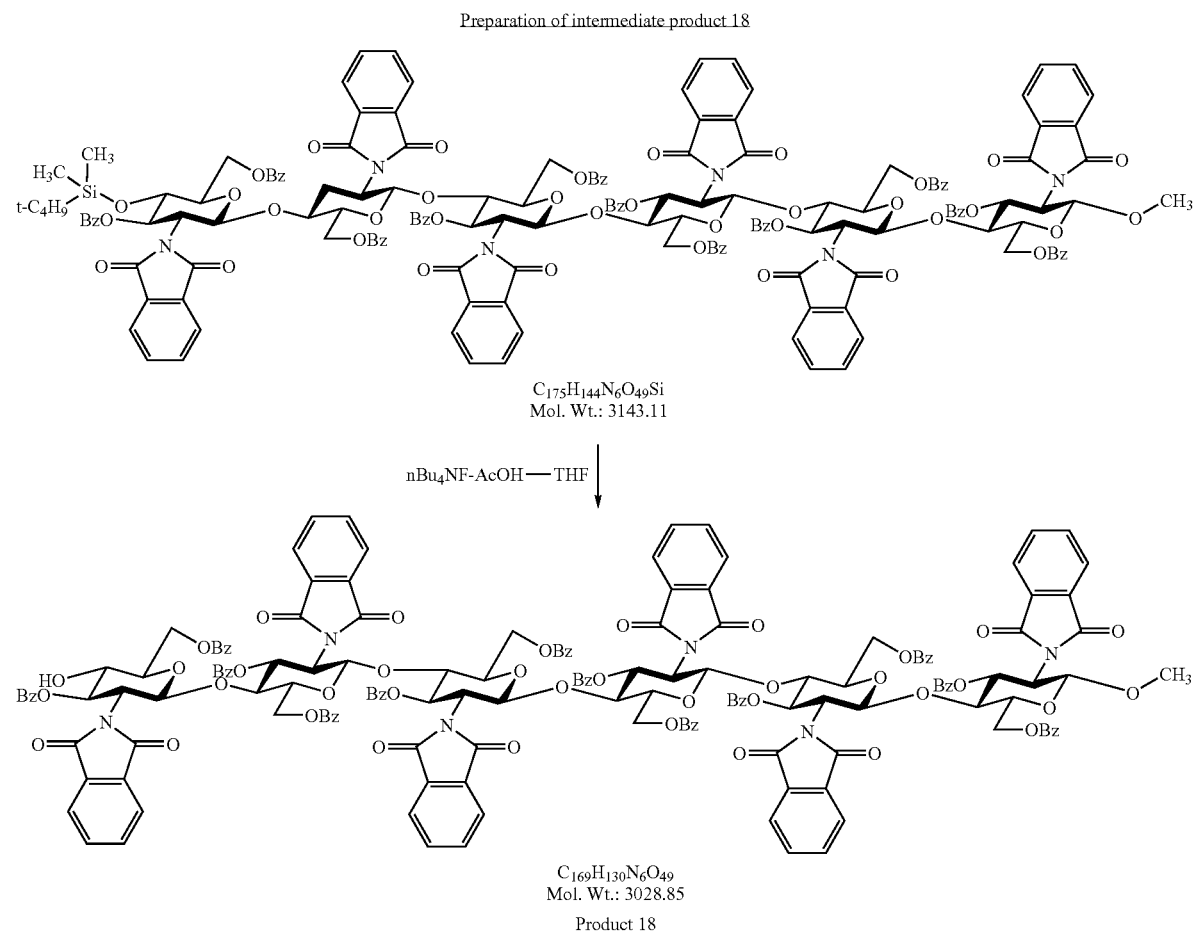

Purified hexasaccharide product 17 (91.0 g, 29 mmol) was dissolved in minimum THF followed by the addition (60 ml each) of 1 M solution of acetic acid in THF and 1 M solution of tetrabutylammoniumfluoride in THF and stirred at room temperature. Reaction progress was checked after 24 h by NMR, which indicated that the reaction was complete. The reaction mixture was evaporated to dryness, redissolved in methylenechloride, washed sequentially with saturated sodium thiosulfate solution, 1 M HCl, and saturated sodium bicarbonate solution, then concentrated to dryness.

To remove nonpolar silicon impurities, the solid was dissolved in ethyl acetate (350 ml). This resulted in a precipitate.

The solution was filtered and the collected precipitate was washed with EtOAc—Hexane (1:1, 2×200 ml); the solution was filtered and dried giving 83.4 g of product 18. $^1$H-NMR (CD$_2$Cl$_2$) δ (only select hydrogen chemical shifts are reported): 8.03-7.00 (phthalimido and benzoate hydrogens), 5.98, 5.78, 5.74, 5.67, 5.67, and 5.54 (6×H-3), 5.59, 5.34, 5.31, 5.25 (H-1s), 3.51 (H-4 of the terminal glucosamine unit), 4.58 (H-6 of the reducing end glucosamine unit), 3.32 (OCH$_3$). MALDI data.: m/e calc. 3027.79 (100%); Obs. M+Na=3051.1. Thus the NMR and MALDI spectra verified the structure of product 18, as shown above.

Example 14

Synthesis of Derivatized Glucosamine Heptasaccharide

Synthesis of Heptamer Product 19

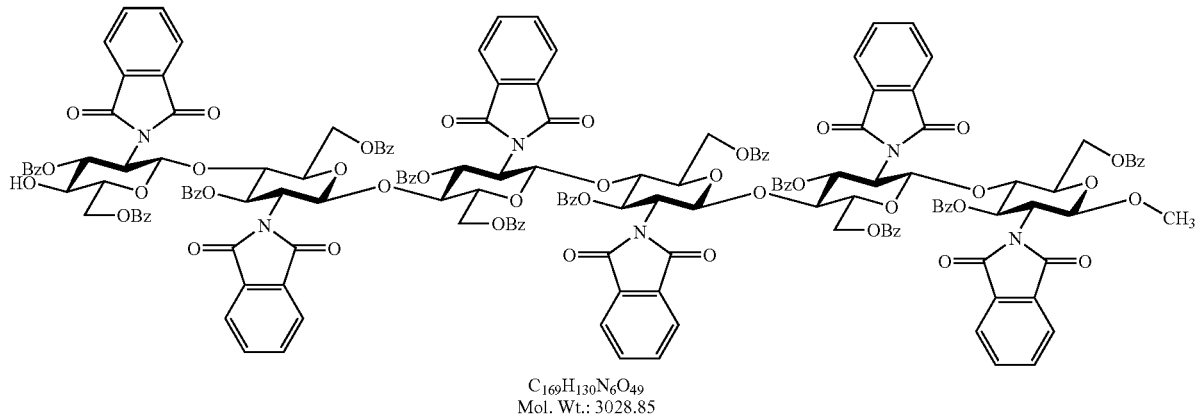

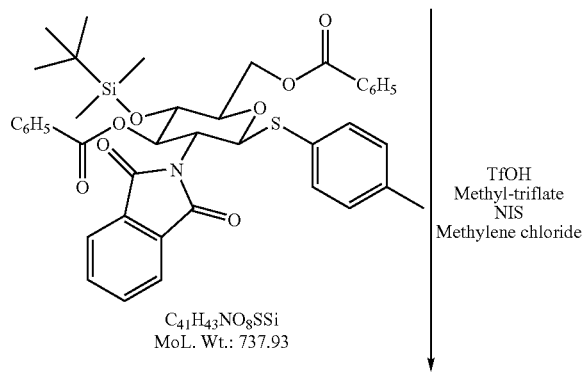

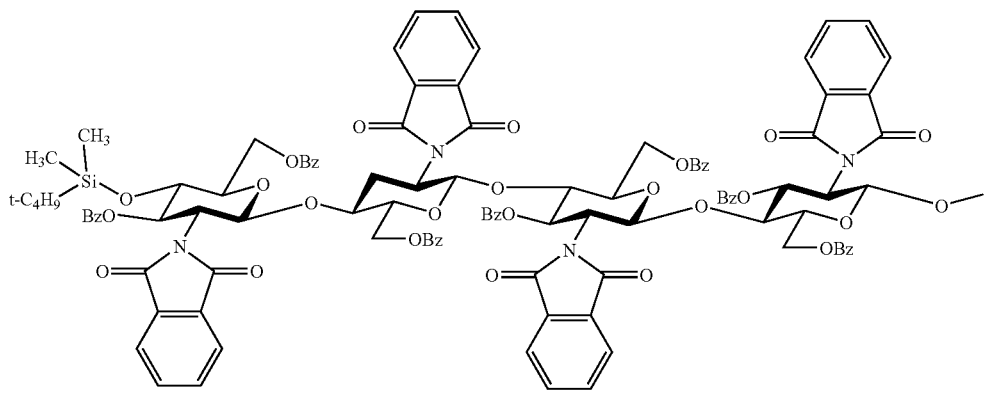

-continued

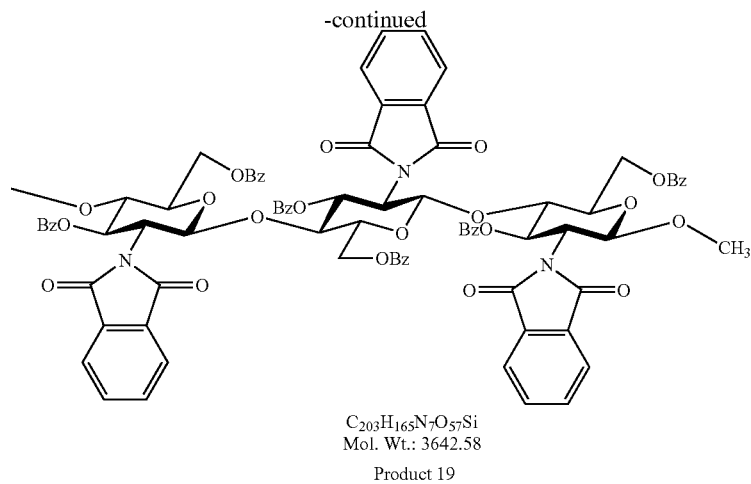

$C_{203}H_{165}N_7O_{57}Si$
Mol. Wt.: 3642.58
Product 19

Thioglycoside monomer (I) (35.8 g; 48.5 mmol) and hexasaccharide product 18 (74.3 g; 24.2 mmol) were dissolved in CH$_2$Cl$_2$ (150 ml) in a 3-necked, 500 ml RBF. 4A Molecular sieves were added (5 g). The solution was cooled to −60° and stirred well. After ten minutes at −60° C., NIS (19.6 g, 87.2 mmol) was added quickly. After five minutes, a solution of triflic acid (3.6 g, 24.2 mmol) and methyl triflate (4.0 g, 24.2 mmol), dissolved together in CH$_2$Cl$_2$ (20 ml), was added in drops (over 40 minutes). The reaction mixture was left at −60° C. for additional 5 hr. An additional 100 ml of the triflic acid/methyl triflate solution was added to the reaction mixture dropwise to reduce of the viscosity and then worked up as follows.

The reaction mixture was poured over saturated sodium bicarbonate and saturated sodium thiosulfate aqueous solution (1:1, 500 ml) contained in an Erlenmeyer flask and thoroughly stirred. Additional methylenechloride (400 ml) was added and the contents were thoroughly mixed for 10 min, the aqueous solution separated, and the organic layer washed sequentially with 1% aqueous bleach solution, 10% aqueous sodium thiosulfate solution, and aqueous saturated sodium bicarbonate solution. The solution was then dried with MgSO$_4$, filtered and concentrated giving 106.4 g of material.

This crude product was dissolved in ethylacetate (400 ml). Hexane (400 ml) was added slowly. A gluey to partially gluey precipitate deposited in the flask. This was filtered and washed with EtOAc—Hexane (3×) and dried under vacuum. The weight of the product was 84.5 g. NMR showed most of the impurities had been removed and the product contained EtOAc and hexane solvent. $^1$H-NMR (CD$_2$Cl$_2$) δ (only select hydrogen chemical shifts are reported): 8.05-6.99 (phthalimido and benzoate hydrogens), 5.98 (H-3 of the reducing end glucosamine unit), 3.72 (H-4 of the terminal glucosamine unit), 4.57 (H-6 of the reducing end glucosamine unit), 3.32 (OCH$_3$), 0.62 (t-butyl), −0.20, −0.36 (2×CH$_3$ of the silicon unit). MALDI data.: m/e calc. 3642.01 (100%). Thus the NMR and MALDI spectra verified the structure of product 19, as shown above.

Example 15

Removal of the Silicon Group from Heptasaccharide Product 19 for Further Chain Extension Preparation of intermediate product 20

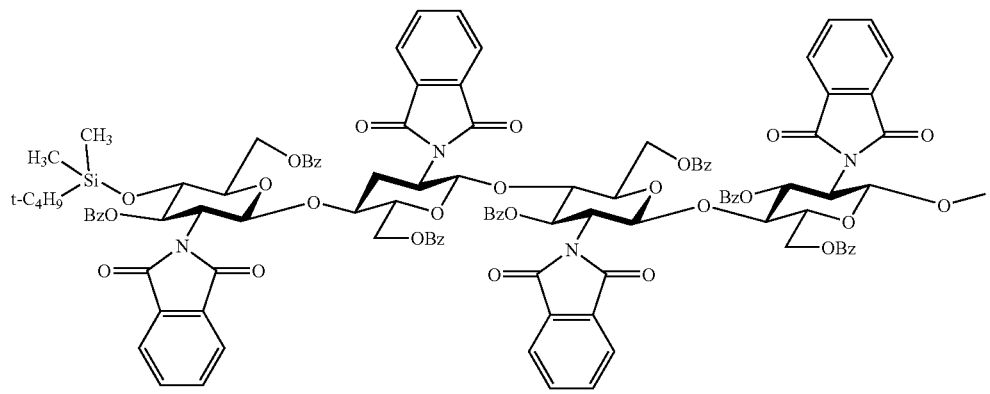

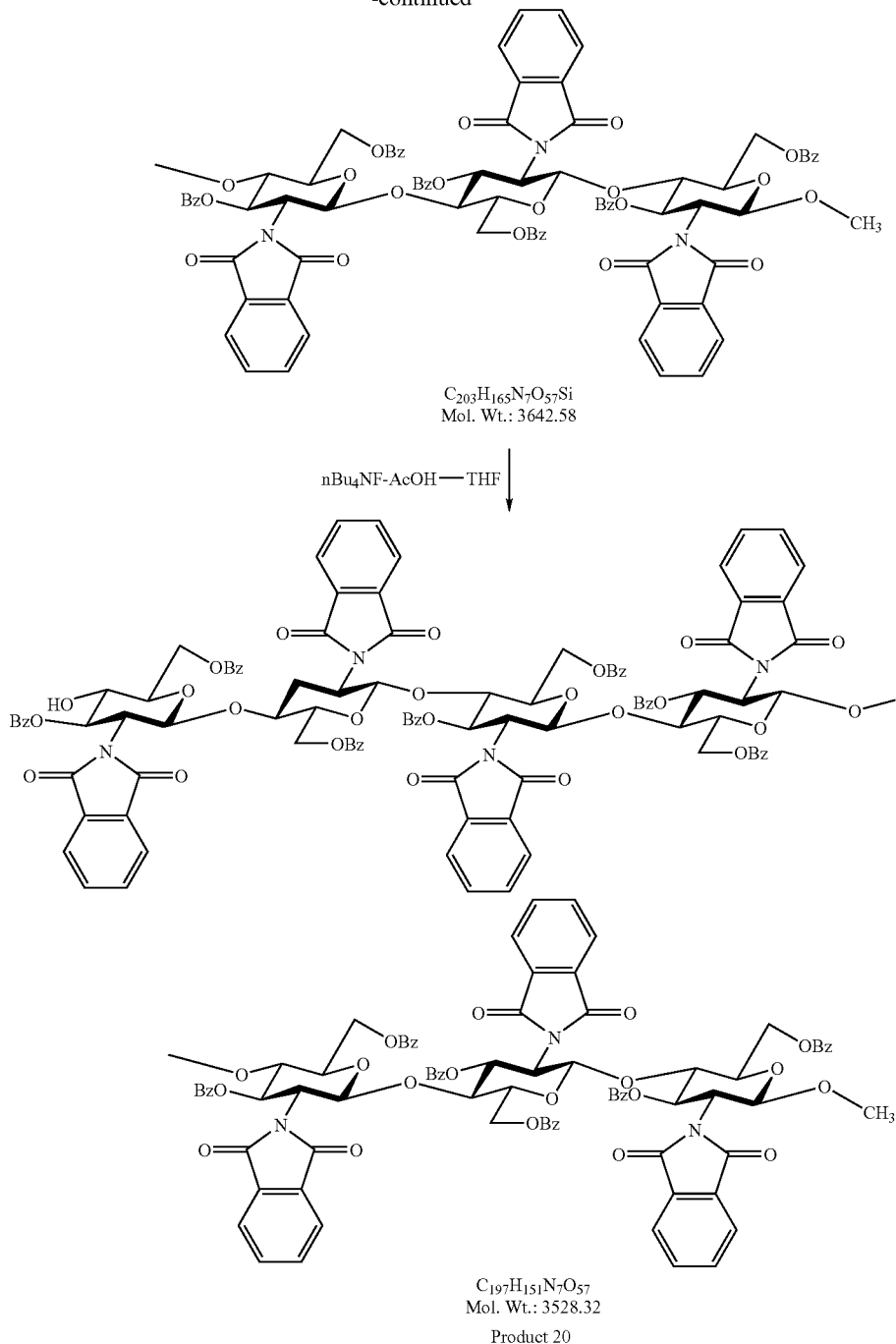

Product 20

Purified heptasaccharide product 19 (35.6 g) was dissolved in minimum THF followed by the addition (45 ml each) of 1 M solution of acetic acid in THF and 1 M solution of tetrabutylammoniumfluoride in THF and stirred at room temperature. After 3 days, the reaction mixture was evaporated to dryness, redissolved in methylenechloride, washed sequentially with saturated sodium thiosulfate solution, 1 M HCl, and saturated sodium bicarbonate solution, then concentrated to dryness.

To remove nonpolar silicon impurities, the solid was dissolved in ethyl acetate (210 ml) and hexane was added slowly in drops (200 ml). The precipitate was filtered and was washed with 1:1 EtOAc—Hexane (100 ml). Finally, diethylether was added to the solid, stirred for 30 min and filtered. The solid was redissolved in methylenechloride and concentrated to dryness giving 28.2 g of product 20. $^1$H-NMR ($CD_2Cl_2$) δ (only select hydrogen chemical shifts are reported): 8.03-6.98 (phthalimido and benzoate hydrogens), 5.97, 5.77, 5.74, 5.65, 5.53 (H-3s), 5.33, 5.29, 5.25 (H-1 s), 3.51 (H-4 of the terminal glucosamine unit), 4.57 (H-6 of the reducing end glucosamine unit), 3.32 ($OCH_3$). MALDI data.: m/e calc. 3527.92 (100%); Obs. M+Na=3550.4. Thus the NMR and MALDI spectra verified the structure of product 20, as shown above.

Example 16
Synthesis of Derivatized Glucosamine Octasaccharide
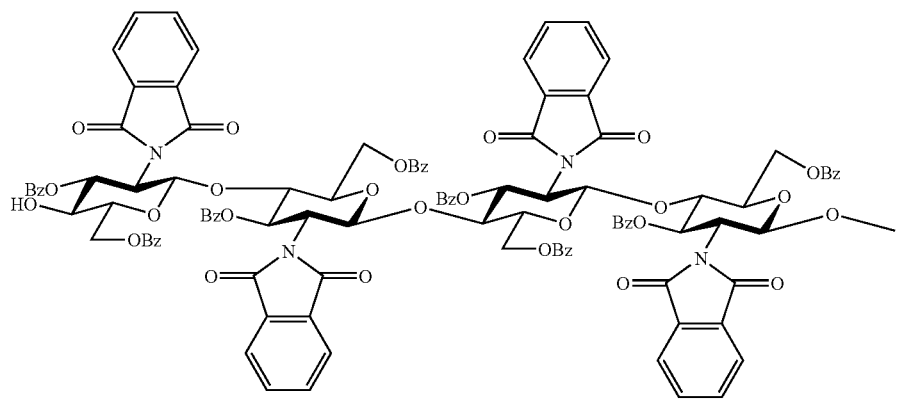
Synthesis of Octamer Product 21
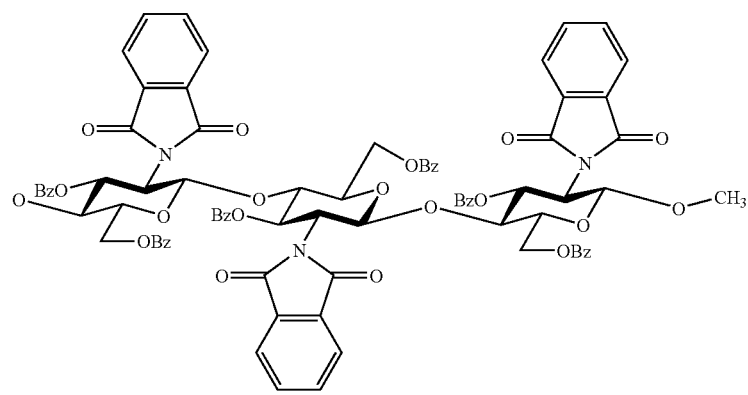
$C_{197}H_{151}N_7O_{57}$
Mol. Wt.: 3528.32
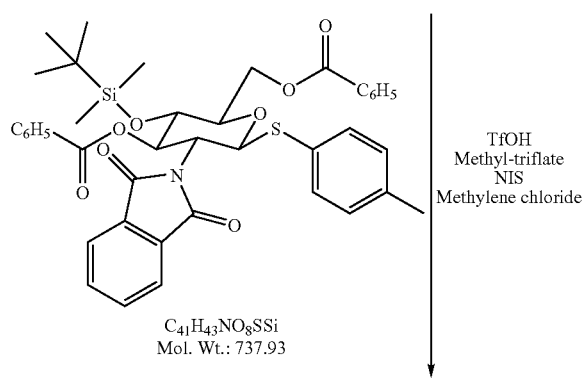
$C_{41}H_{43}NO_8SSi$
Mol. Wt.: 737.93
TfOH
Methyl-triflate
NIS
Methylene chloride -continued

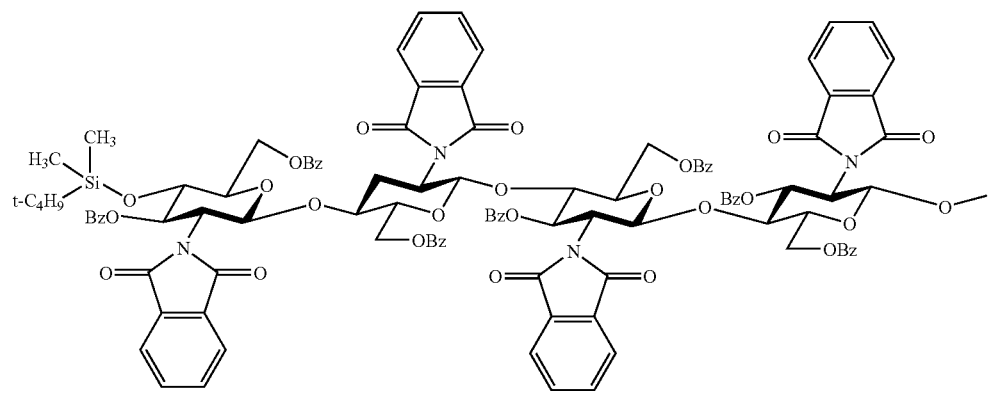

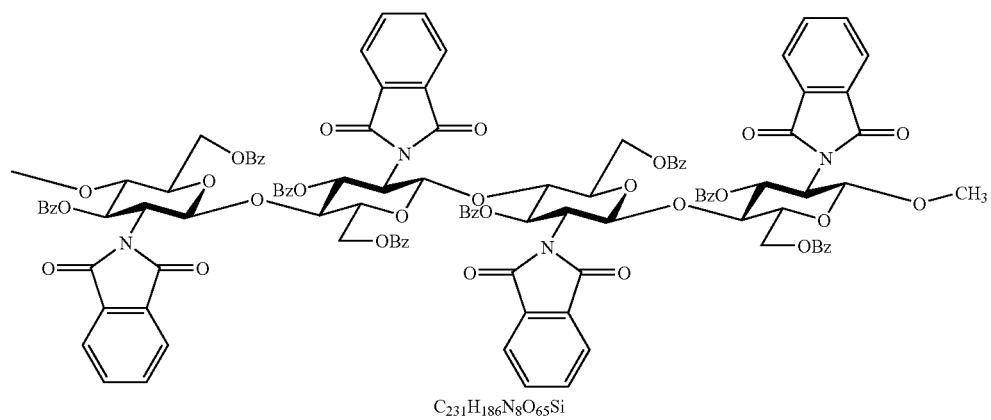

$C_{231}H_{186}N_8O_{65}Si$
Mol. Wt.: 4142.05
Product 21

Thioglycoside monomer (I) (11.2 g, 15.3 mmol) and heptasaccharide product 20 (26.7 g, 7.6 mmol) were dissolved in $CH_2Cl_2$ (100 mL) in a 3-necked, 250 mL RBF. 4A Molecular sieves (5 g) were added. The solution was cooled to −60° C. and stirred well. After ten minutes at −60° C., NIS (6.2 g, 27.2 mmol) was added quickly. After five minutes, a solution of triflic acid (1.2 g, 7.6 mmol) and methyl triflate (1.3 g, 7.6 mmol), dissolved together in $CH_2Cl_2$ (20 ml), was added in drops (over 40 minutes). The reaction mixture was left at −60° C. for an additional 5 hr. An additional 100 ml of the triflic acid/methyl triflate solution was added to the reaction mixture dropwise to reduce of the viscosity and then worked up as follows.

The reaction mixture was poured over saturated sodium bicarbonate and saturated sodium thiosulfate aqueous solution (1:1, 200 ml) contained in an Erlenmeyer flask and thoroughly stirred. Additional methylenechloride (100 ml) was added and the contents were thoroughly mixed for 10 min, the aqueous solution separated, and the organic layer washed sequentially with 10% aqueous sodium thiosulfate solution, 1% aqueous bleach solution, and aqueous saturated sodium bicarbonate solution. The solution was then dried with $MgSO_4$, filtered and concentrated. The solid was dissolved in ethylacetate (200 ml) forming was a colloidal suspension, and hexane (200 ml) was slowly added. The precipitate was filtered and washed with EtOAc—Hexane (1:1) and dried under high vacuum over the weekend. Weight of the residue, product 21, was 30.0 g. $^1$H-NMR ($CD_2Cl_2$) δ (only select hydrogen chemical shifts are reported): 8.07-6.97 (phthalimido and benzoate hydrogens), 5.97, 5.76, 5.61 (H-3s), 3.71 (H-4 of the terminal glucosamine unit), 4.57 (H-6 of the reducing end glucosamine unit), 3.32 ($OCH_3$), 0.61 (t-butyl), −0.22, −0.37 (2×$CH_3$ of the silicon unit). MALDI data.: m/e calc. 4141.13 (100%); Obs. M+Na=4163.2. Thus the NMR and MALDI spectra verified the structure of product 21, as shown above.

Example 17
Removal of the Silicon Group from Octasaccharide Product 21 for Further Chain Extension
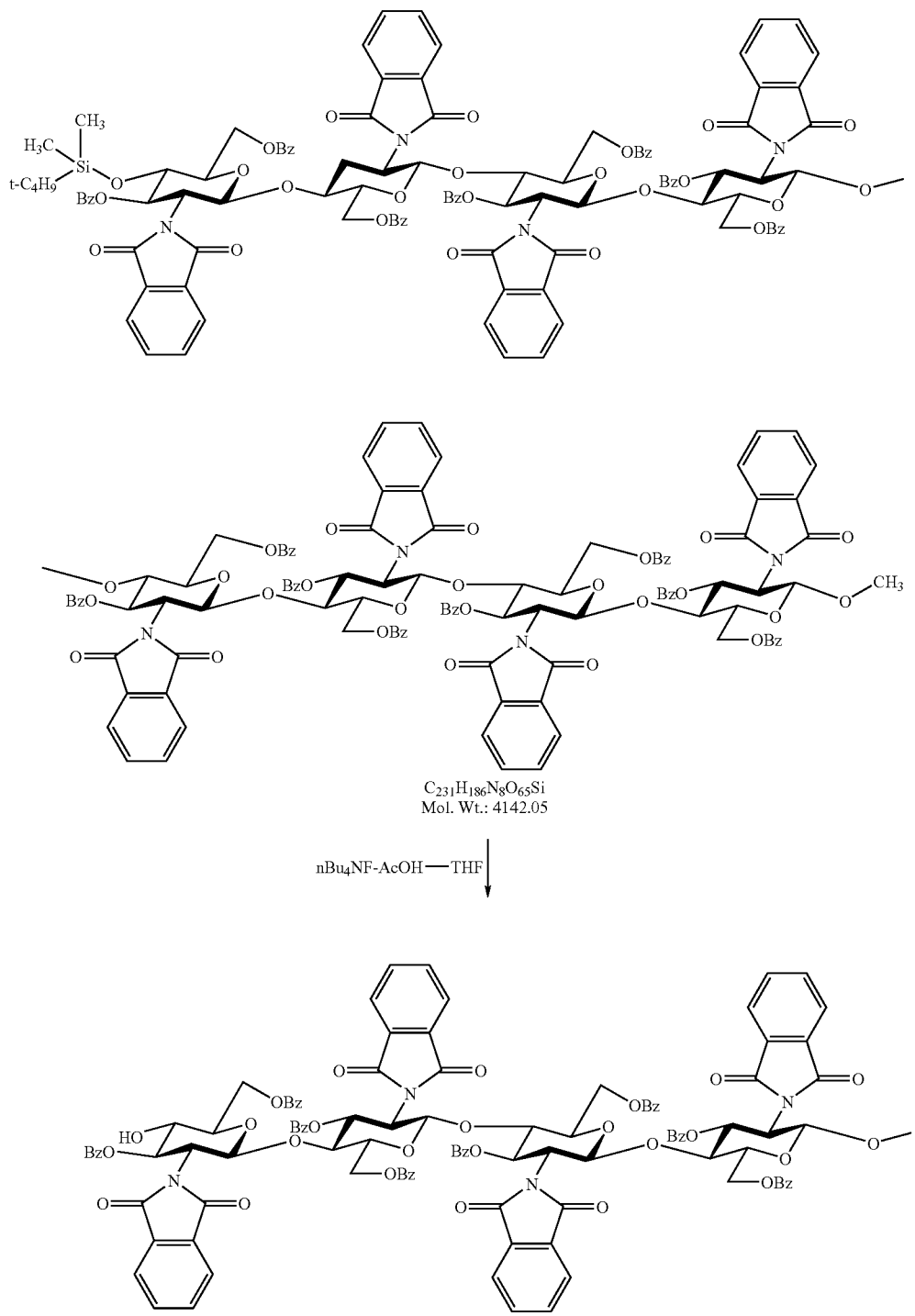
Preparation of intermediate product 22
$C_{231}H_{186}N_8O_{65}Si$
Mol. Wt.: 4142.05
nBu₄NF-AcOH—THF

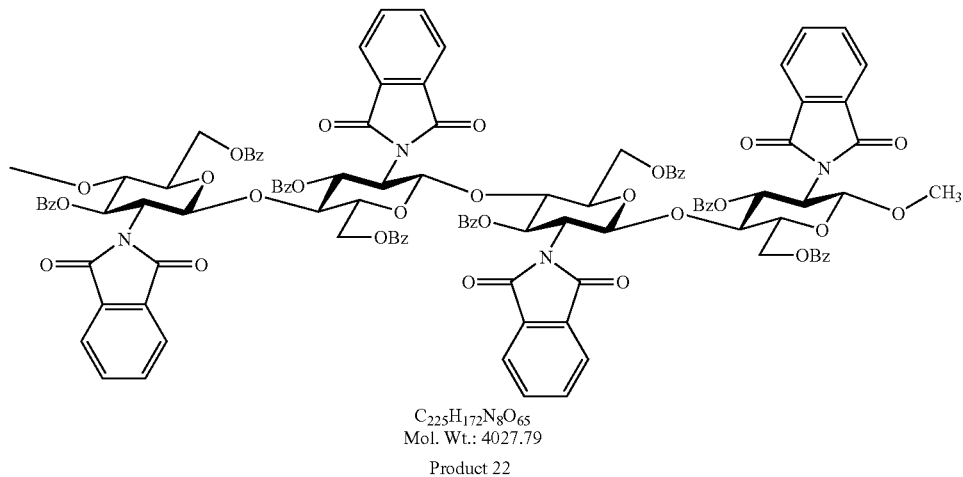

$C_{225}H_{172}N_8O_{65}$
Mol. Wt.: 4027.79
Product 22

Purified octasaccharide product 21 (29.0 g) was dissolved in minimum THF followed by the addition (25 ml each) of 1 M solution of acetic acid in THF and 1 M solution of tetrabutylammoniumfluoride in THF and stirred at room temperature. After 3 days, the reaction mixture was evaporated to dryness, redissolved in methylenechloride, washed sequentially with saturated sodium thiosulfate solution, 1 M HCl, and saturated sodium bicarbonate solution, then dried and concentrated to dryness.

To remove nonpolar silicon impurities, the solid was dissolved in ethyl acetate (250 ml which resulted in a milky solution, and hexane was added slowly in drops (200 ml). This resulted in a snow white precipitate. The residue was filtered and it was washed with 1:1 EtOAc—Hexane (2×200 ml) and dried giving 26.2 g of product 22. $^1$H-NMR (CD$_2$Cl$_2$) δ (only select hydrogen chemical shifts are reported): 8.02-6.98 (phthalimido and benzoate hydrogens), 5.97, 5.76, 5.73 (H-3s of the glucosamine unit), 3.50 (H-4 of the terminal glucosamine unit), 4.57 (H-6 of the reducing end glucosamine unit), 3.32 (OCH$_3$), 2.93 (OH). MALDI data.: m/e calc. 4027.05 (100%); Obs. M+Na=4049.4. Thus the NMR and MALDI spectra verified the structure of product 22, as shown above.

Example 18

Synthesis of Derivatized Glucosamine Nanosaccharide

Synthesis of Nonamer Product 23

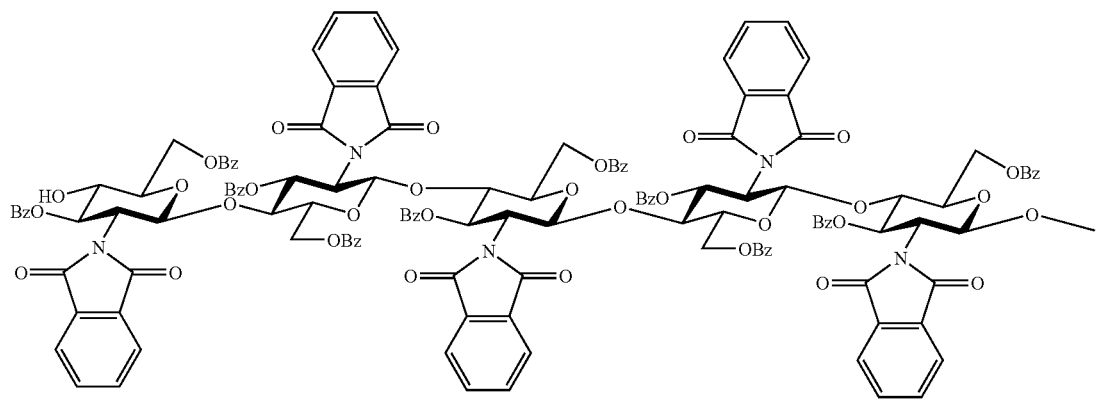

-continued
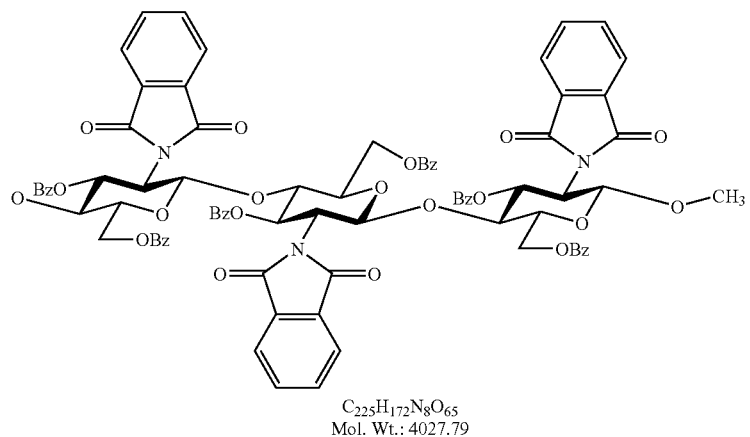
C$_{225}$H$_{172}$N$_8$O$_{65}$
Mol. Wt.: 4027.79
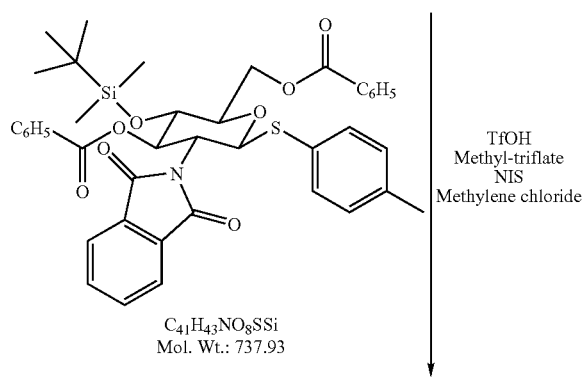
C$_{41}$H$_{43}$NO$_8$SSi
Mol. Wt.: 737.93
TfOH
Methyl-triflate
NIS
Methylene chloride
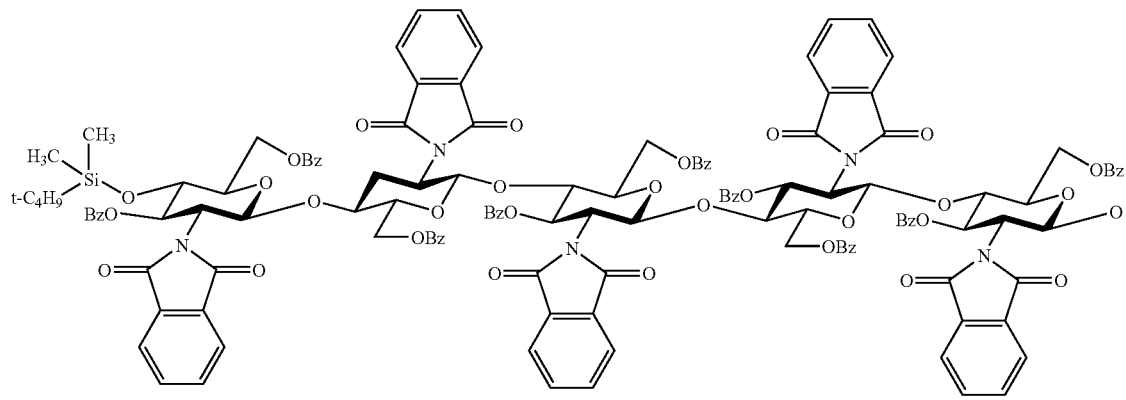

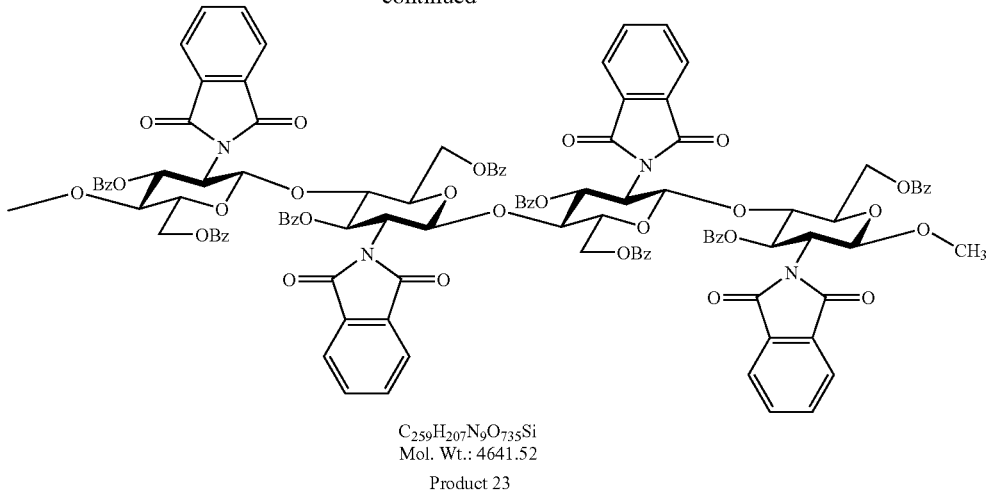

C$_{259}$H$_{207}$N$_9$O$_{735}$Si
Mol. Wt.: 4641.52
Product 23

Thioglycoside monomer (I) (7.4 g, 10 mmol) and Octasaccharide product 22 (20 g, 5.0 mmol) were dissolved in CH$_2$Cl$_2$ (30 ml) in a 3-necked, 250 ml RBF. 4A Molecular sieves (5 g) were added. The reaction flask was placed in an acetone/dry ice bath; dry ice was added slowly to achieve and maintain a temperature of −60° C. to −55° C. Sugars were allowed to stir ten minutes at −60° C. Then NIS (4.1 g, 18 mmol) was added quickly. The reaction mixture was allowed to stir five minutes, before addition of a solution of triflic acid (0.8 g, 5 mmol) and methyl triflate (0.82 g, 5 mmol), dissolved together in CH$_2$Cl$_2$ (20 ml), was added in drops (over 40 minutes). The reaction mixture was left at −60° C. for an additional 5 hr. After 4 h, an additional 50 ml of the triflic acid/methyl triflate solution was added to the reaction mixture dropwise to reduce of the viscosity.

The reaction mixture was poured over saturated sodium bicarbonate and saturated sodium thiosulfate aqueous solution (1:1,150 ml) contained in an Erlenmeyer flask and thoroughly stirred. Additional methylenechloride (100 ml) was added and the contents were thoroughly mixed for 10 min, the aqueous solution separated, and the organic layer washed sequentially with 10% aqueous sodium thiosulfate solution, 1% aqueous bleach solution, and aqueous saturated sodium bicarbonate solution. The solution was dried and concentrated. The resultant solid was dissolved in ethylacetate (200 ml) forming a colloidal suspension and hexane (200 ml) was slowly added. The precipitate was filtered and the process was repeated once more and finally, the precipitate was filtered and washed with EtOAc—Hexane (1:1) and dried under high vacuum over the weekend. Weight of the residue, product 23, was 21.4 g. $^1$H-NMR (CD$_2$Cl$_2$) δ (only select hydrogen chemical shifts are reported): 8.06-6.97 (phthalimido and benzoate hydrogens), 5.97, 5.76, 5.70 (H-3s of glucosamine unit), 3.72 (H-4 of the terminal glucosamine unit), 4.57 (H-6 of the reducing end glucosamine unit), 3.32 (OCH$_3$), 0.62 (t-butyl), −0.21, −0.37 (2×CH$_3$ of the silicon unit). MALDI data.: m/e calc. 4641.26 (100%); Obs. M+Na=4662.7. Thus the NMR and MALDI spectra verified the structure of product 23, as shown above.

Example 19

Removal of the Silicon Group from Nanosaccharide Product 23 for Further Chain Extension Preparation of the intermediate product 24

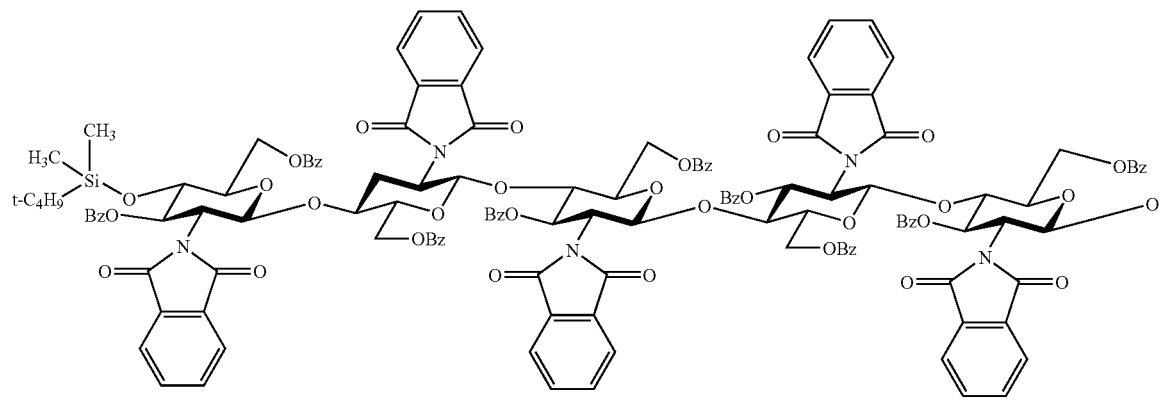

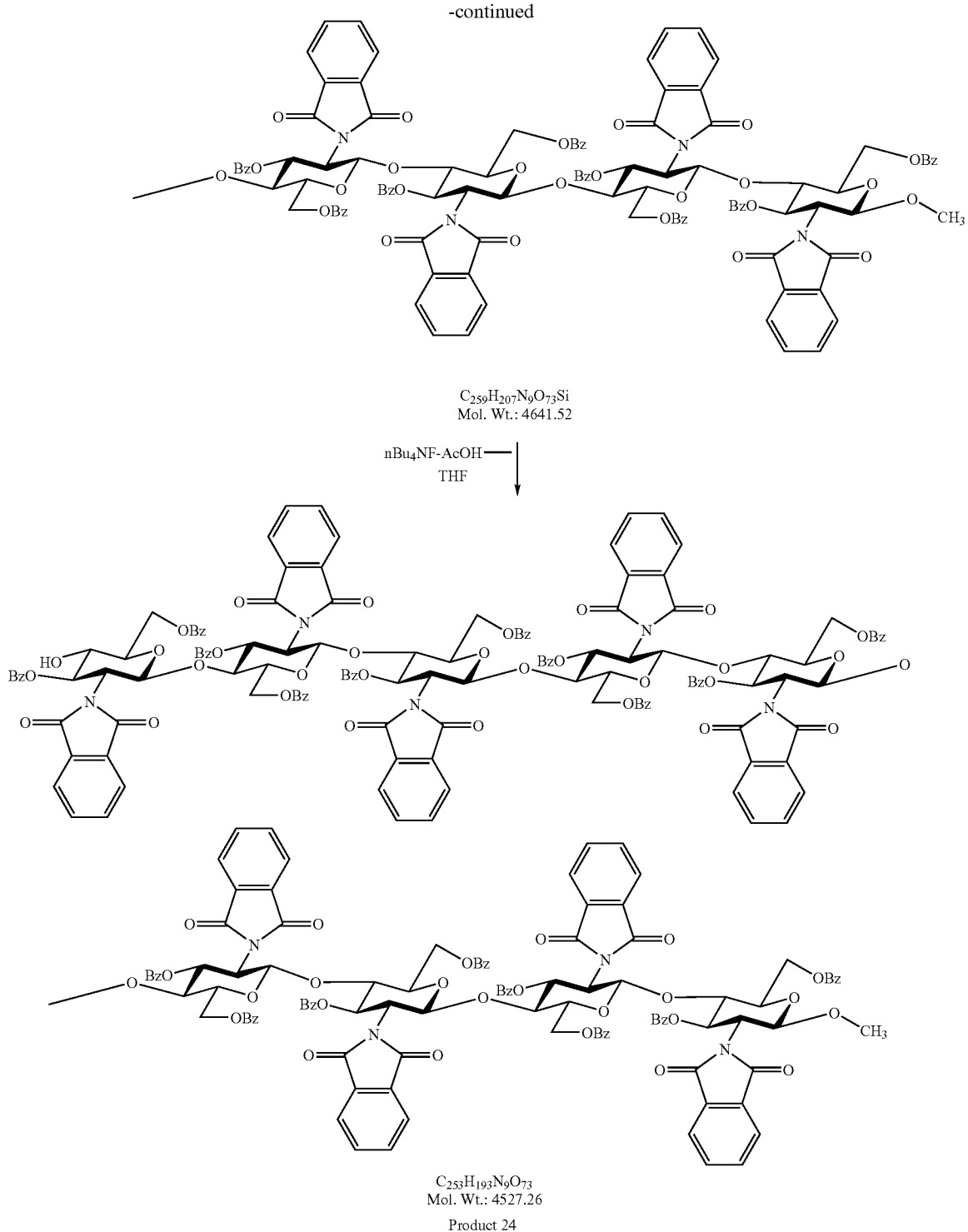

Nonasaccharide (19.9 g, 4.3 mmol) was dissolved in minimum THF containing AcOH (15 mmol) and NBu$_4$F (15 mmol) and stirred at room temperature. After 24 h, the reaction mixture was evaporated to dryness, the residue redissolved in methylenechloride and washed sequentially with deionized water, 1 M HCl, 1% aqueous bleach solution (to remove the light brown color), and saturated sodium bicarbonate solution, then dried and concentrated to dryness.

To remove nonpolar silicon impurities, the solid was suspended in ethyl acetate (150 ml) producing a milky solution, and hexane was added slowly in drops (150 ml). This resulted in a snow white precipitate. The residue was filtered and it was washed with 1:1 EtOAc—Hexane and dried (19.5 g).).
$^1$H-NMR (CD$_2$Cl$_2$) δ (only select hydrogen chemical shifts are reported): 8.02-6.98 (phthalimido and benzoate hydrogens), 5.97, 5.76, 5.73, 5.53 (H-3s of glucosamine unit), 3.51

(H-4 of the terminal glucosamine unit), 4.57 (H-6 of the reducing end glucosamine unit), 3.32 (OCH$_3$), 2.94 (OH). MALDI data.: m/e calc. 4526.17 (100%). Thus the NMR and MALDI spectra verified the structure of product 24, as shown above.

Example 20

Synthesis of Derivatized Glucosamine Decasaccharide

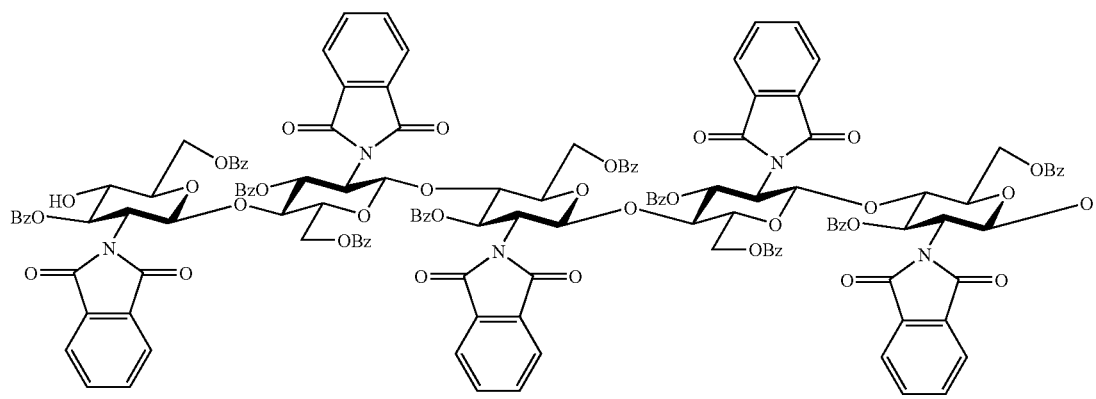

Synthesis of Decamer Product 25

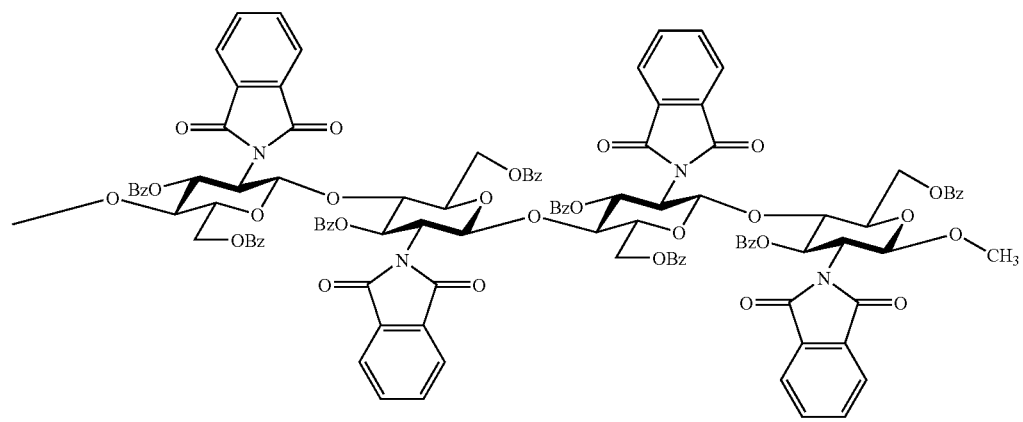

C$_{253}$H$_{193}$N$_9$O$_{73}$
Mol. Wt.: 4527.26

Product 24

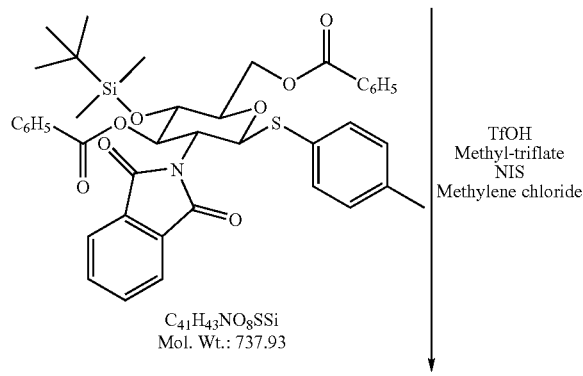

C$_{41}$H$_{43}$NO$_8$SSi
Mol. Wt.: 737.93

TfOH
Methyl-triflate
NIS
Methylene chloride

-continued

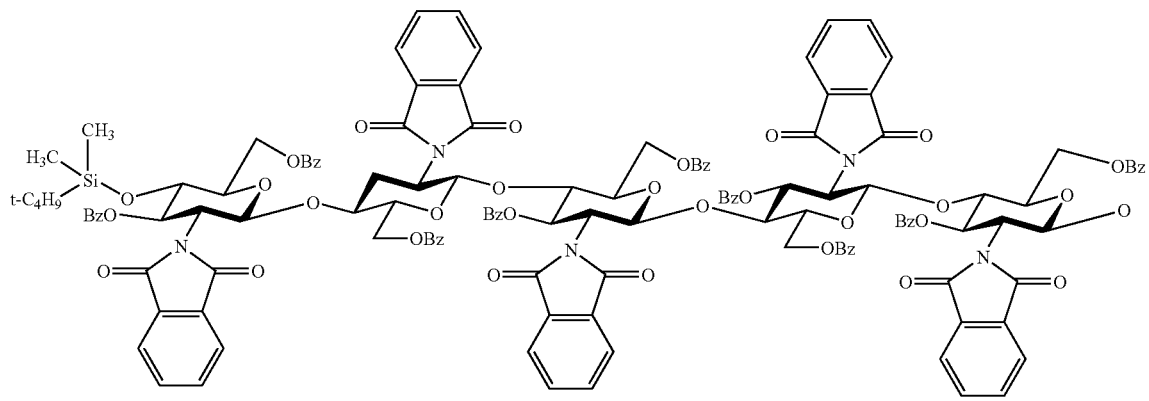

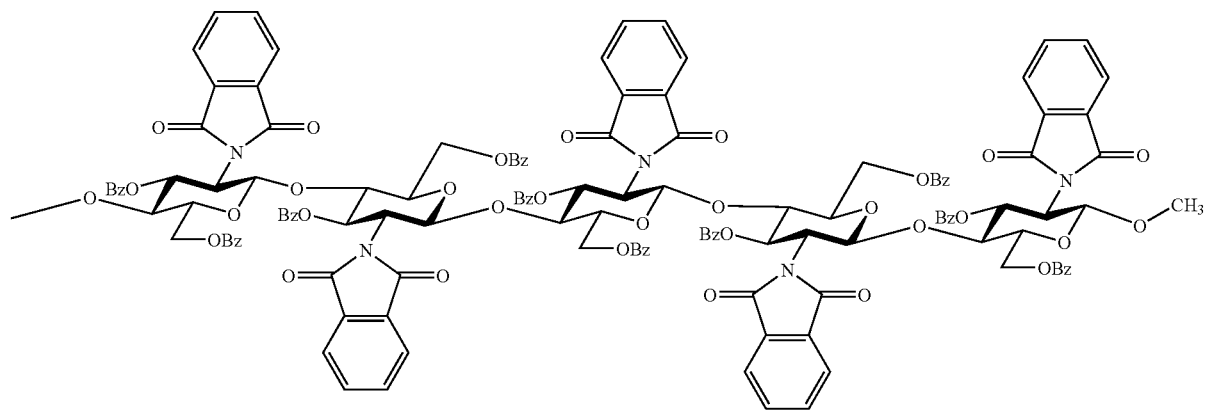

C$_{287}$H$_{228}$N$_{10}$O$_{81}$Si
Mol. Wt.: 5140.99
Product 25

Thioglycoside monomer (I) (6.1 g, 8.2 mmol) and nanosaccharide product 24 (18.5 g, 4.1 mmol) were dissolved in CH$_2$Cl$_2$ (30 ml) in a 3-necked, 250 ml RBF. 4A Molecular sieves were added (5 g). The reaction flask was placed in an acetone/dry ice bath; dry ice was added slowly to achieve and maintain a temperature of −60° C. to −55° C. Sugars were allowed to stir ten minutes at −60° C. Then NIS (3.3 g, 14.8 mmol) was added quickly. Reaction mixture was allowed to stir five minutes, before addition of TfOH (0.62 g, 4.1 mmol) and methyl triflate (0.70 g, 4.1 mmol), both dissolved together in CH$_2$Cl$_2$ (5 ml), was added to the cold solution in drops (over 40 minutes). The reaction mixture was left at −60° C. for an additional 5 h. After 4 h, an additional 50 ml of TfOH/methyl triflate solution was added to the reaction mixture dropwise to reduce of the viscosity. The reaction mixture was poured over saturated sodium bicarbonate and saturated sodium thiosulfate aqueous solution (1:1, 150 ml) contained in an Erlenmeyer flask and thoroughly stirred. Additional methylenechloride (100 ml) was added and the contents were thoroughly mixed for 10 min, the aqueous solution separated, and the organic layer washed sequentially with 10% aqueous sodium thiosulfate solution, 1% aqueous bleach solution, and aqueous saturated sodium bicarbonate solution. The solution was dried and concentrated. The resultant solid was dissolved in ethylacetate (200 ml) forming a colloidal suspension, and hexane (200 ml) was slowly added. The precipitate was filtered and the process was repeated once more and finally, the precipitate was filtered and washed with EtOAc—Hexane (1:1) and dried under high vacuum over the weekend. Weight of the resulting product 25 was 19.5 g. $^1$H-NMR (CD$_2$Cl$_2$) δ (only select hydrogen chemical shifts are reported): 8.06-6.96 (phthalimido and benzoate hydrogens), 5.97, 5.76, 5.70 (H-3s of glucosamine unit), 3.72 (H-4 of the terminal glucosamine unit), 4.57 (H-6 of the reducing end glucosamine unit), 3.31 (OCH$_3$), 0.61 (t-butyl), −0.21, −0.37 (2×CH$_3$ of the silicon unit). MALDI data.: m/e calc. 5140.39 (100%); Obs. M+Na=5163.1. Thus the NMR and MALDI spectra verified the structure of product 25, as shown above.

Example 21
Removal of the Silicon Group from Decasaccharide Product 25 for Further Chain Extension
Preparation of intermediate product 26
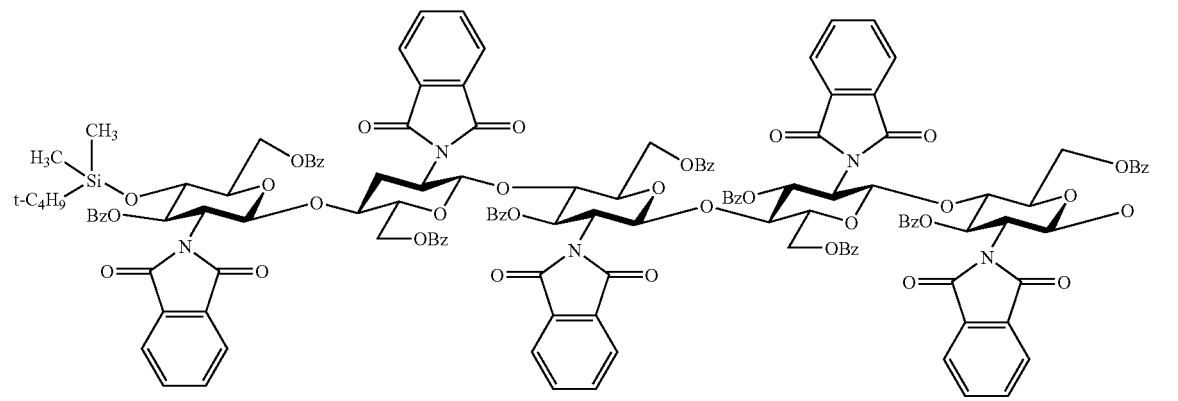
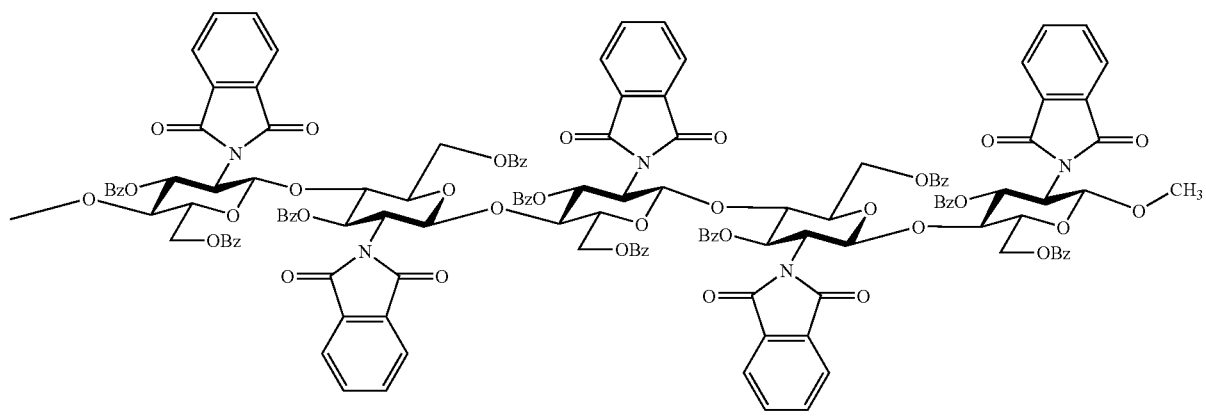
C_287H_228N_10O_81Si
Mol. Wt.: 5140.99
nBu_4NF-AcOH—THF
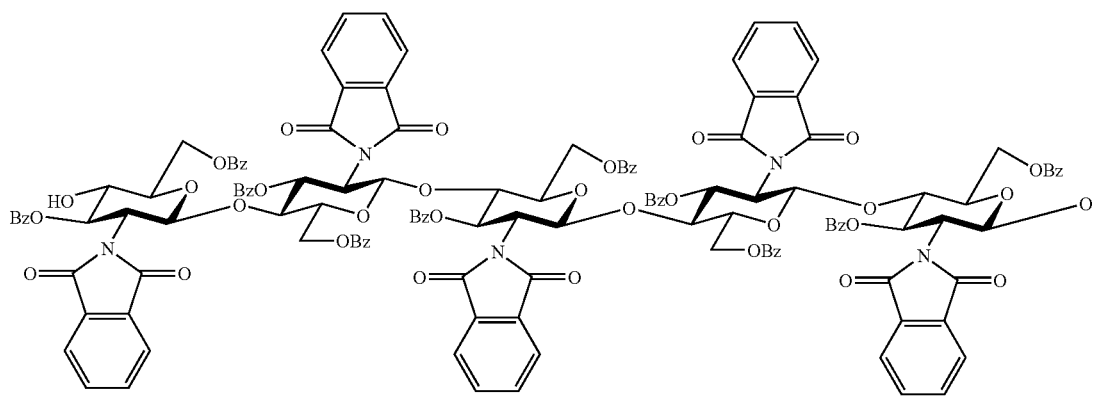

-continued

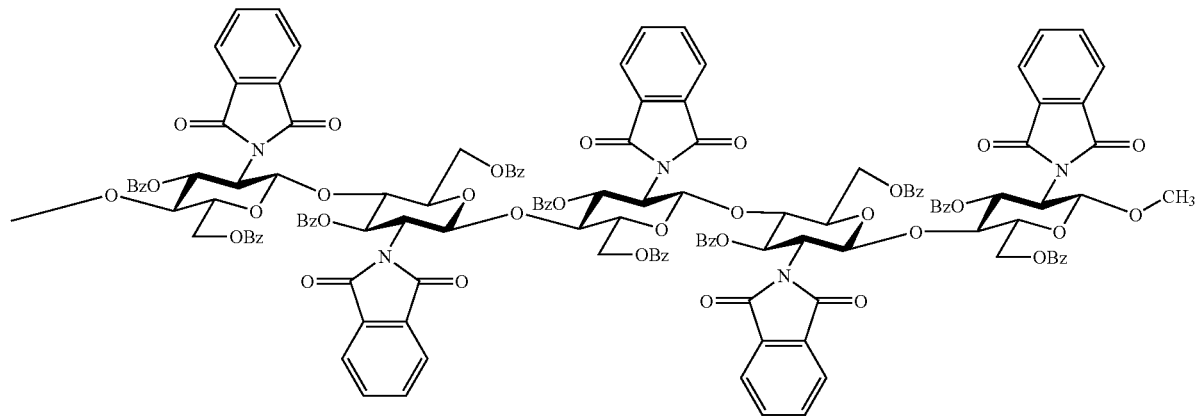

C$_{281}$H$_{214}$N$_{10}$O$_{81}$
Mol. Wt.: 5026.72
Product 26

Decasaccharide product 25 (18.5 g) was dissolved in minimum THF containing AcOH (15 mmol) and NBu$_4$F (15 mmol) and stirred at room temperature. After 24 h, the reaction mixture was evaporated to dryness, the residue redissolved in methylenechloride and washed sequentially with deionized water, 1 M HCl, 1% aqueous bleach solution (to remove the light brown color), and saturated sodium bicarbonate solution, then dried and concentrated to dryness.

To remove nonpolar silicon impurities, the solid was suspended in ethyl acetate (150 ml) producing a milky solution, and hexane was added slowly in drops (150 ml). This resulted in a snow white precipitate. The residue was filtered and it was washed with 1:1 EtOAc—Hexane and dried giving 16.5 g of product 26. $^1$H-NMR (CD$_2$Cl$_2$) δ (only select hydrogen chemical shifts are reported): 8.02-6.96 (phthalimido and benzoate hydrogens), 5.97, 5.76, 5.74, 5.53 (H-3s of glucosamine unit), 3.50 (H-4 of the terminal glucosamine unit), 4.57 (H-6 of the reducing end glucosamine unit), 3.32 (OCH$_3$). Thus the NMR and MALDI spectra verified the structure of product 26, as shown above.

Example 22

Synthesis of Derivatized Glucosamine Undecasaccharide

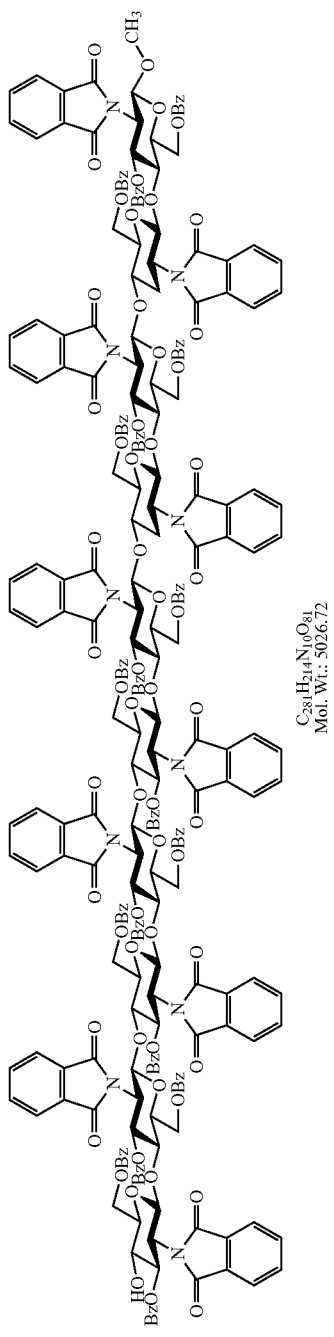
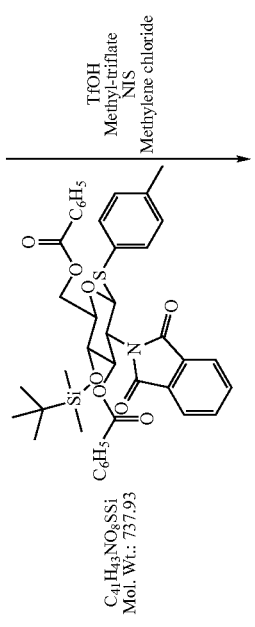
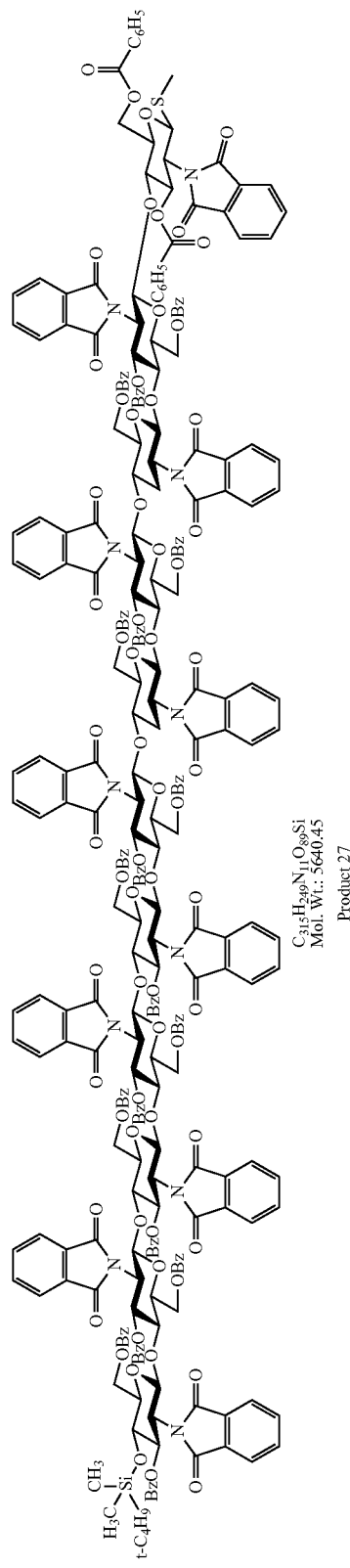
Synthesis of undecasaccharide product 27

Thioglycoside monomer (I) (4.4 g, 6 mmol) and decasaccharide product 26 (15.0 g, 3.0 mmol) were dissolved in CH$_2$Cl$_2$ (30 ml) in a 3-necked, 250 ml RBF. 4A Molecular sieves were added (5 g). The reaction flask was placed in an acetone/dry ice bath; dry ice was added slowly to achieve and maintain a temperature of –60° C. to –55° C. Sugars were allowed to stir ten minutes at –60° C. Then NIS (2.5 g, 10.8 mmol) was added quickly. The reaction mixture was allowed to stir five minutes, before addition of TfOH (0.45 g, 3 mmol) and methyl triflate (0.50 g, 3 mmol), both dissolved together in CH$_2$Cl$_2$ (5 ml), was added to the cold solution in drops (over 40 minutes). The reaction mixture was left at –60° C. for an additional 5 hr. After 4 h, additional 50 ml of TfOH/methyl triflate solution was added to the reaction mixture dropwise to reduce of the viscosity.

The reaction mixture was poured over saturated sodium bicarbonate and saturated sodium thiosulfate aqueous solution (1:1, 150 ml) contained in an Erlenmeyer flask and thoroughly stirred. Additional methylenechloride (100 ml) was added and the contents were thoroughly mixed for 10 min, the aqueous solution separated, and the organic layer washed sequentially with 10% aqueous sodium thiosulfate solution, 1% aqueous bleach solution, and aqueous saturated sodium bicarbonate solution. The solution was dried and concentrated. The resultant solid was dissolved in ethylacetate (200 ml) forming a colloidal suspension, and hexane (200 ml) was slowly added. The precipitate was filtered and the process was repeated once more and finally, the precipitate was filtered and washed with EtOAc—Hexane (1:1) and dried under high vacuum over the weekend. Weight of the resulting product 27 was 15.9 g. $^1$H-NMR (CD$_2$Cl$_2$) δ (FIG. 3; only select hydrogen chemical shifts are reported): 8.04-6.96 (phthalimido and benzoate hydrogens), 5.97, 5.76, 5.69, 5.56 (H-3s of glucosamine unit), 3.71 (H-4 of the terminal glucosamine unit), 4.56 (H-6 of the reducing end glucosamine unit), 3.31 (OCH$_3$), 0.61 (t-butyl), –0.22, –0.37 (2×CH$_3$ of the silicon unit). MALDI data (FIG. 4): m/e calc. 5640.52 (100%); Obs. M+Na=5662.2. The 100% intensity peak at 5662.2 corresponds to M+Na thereby confirming the structure. Thus the NMR and MALDI spectra verified the structure of product 27, as shown above.

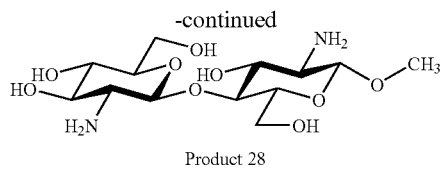

Product 28

MR = Merrifield Resin

Step 1: The derivatized disaccharide product 10 (14.1 g, 13.7 mmol) was dissolved in anhydrous methanol (600 ml). Sodium methoxide solution (0.5 M, 7.5 ml) was added and the solution was stirred at room temperature for 24 h. Examination by TLC (EtOAc—Hexane-Ethanol=20:20:1 & EtOAc—Hexane-Ethanol=5:5:1) showed the disappearance of the starting material. The reaction was neutralized with sulfonic acid resin, filtered and concentrated to dryness. NMR of the product indicated incomplete de-O-benzoylation. The product was redissolved in anhydrous methanol (600 ml), 0.5 M sodium methoxide solution (7 ml) was added and the solution was refluxed for 3 days. It was then neutralized with sulfonic acid resin, filtered and concentrated to dryness.

Step 2: The product from Step 1 was dissolved in 250 ml of n-butanol. Polystyrene-ethylenediamine resin (26.0 g) was added and the slurry was heated to 105° C. with stirring for 24 h. It was then filtered, concentrated to dryness, and the resulting material was redissolved in water and washed with methylenechloride. The aqueous layer was concentrated to dryness. Examination of the product by proton NMR (presence of signals between 7-8 ppm) showed incomplete phthalimide removal. The product was redissolved in n-butanol (100 ml) containing 10 g of freshly prepared MR-ethylenediamine resin and heated to 100° C. for 16 h, filtered over a celite pad and concentrated to dryness. Weight of the product, designated product 28, was 4.0 g. $^1$H-NMR (D$_2$O) δ: 4.48 and 4.33 (2×H-1), 3.98, 3.95, 3.83, 3.76 (4×H-6), 3.67, 3.54, 3.43, 3.40 (2×H-3, 2×H-4), 3.60 (OCH$_3$), 2.70 and 2.66 (2×H-2). Mass spectral data (electrospray): m/e calc. 354.16 (100%); Obs. M+1=355.1. Thus the NMR and MALDI spectra verified the structure of product 28, as shown above.

Example 23

Synthesis of Diglucosamine from Derivatized Glucosamine Disaccharide

Synthesis of Diglucosamine product 28

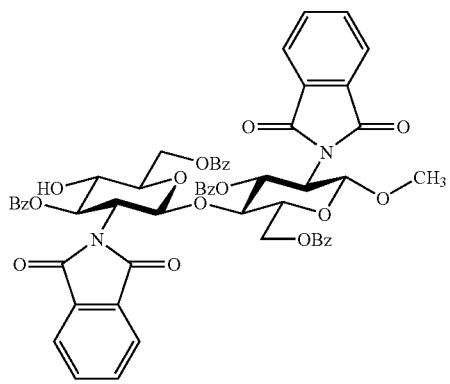

Product 10

Step 1 = NaOMe/MeOH

Step 2 = MR-CH$_2$—NH(CH$_2$)$_2$NH$_2$/ n-Butanol

Example 24

Synthesis of Triglucosamine from Derivatized Glucosamine Trisaccharide

Synthesis of triglucosamine product 29

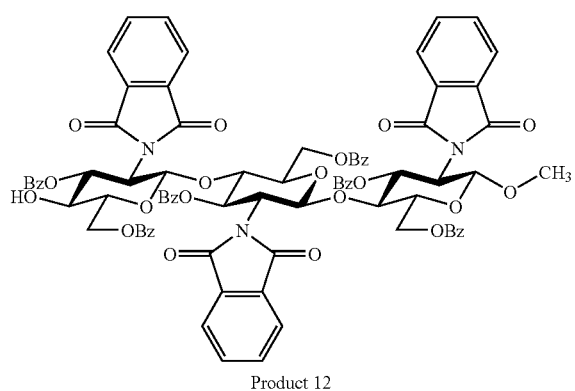

Product 12

Step 1 = NaOMe/MeOH

Step 2 = MR-CH$_2$—NH(CH$_2$)$_2$NH$_2$/ n-Butanol

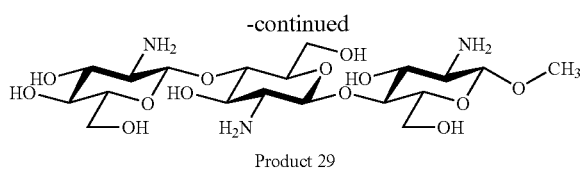

Product 29

MR = Merrifield Resin

The derivatized trisaccharide product 12 (6.1 g) was suspended in MeOH (300 ml), and then NaOMe (0.5 M, 7 ml) was added and stirred at room temperature for 2 days. The mixture was then heated to 65° C. for 24 h. Examination of the reaction mixture by proton NMR indicated that all benzoate groups had been removed. A white precipitate appeared in the reaction flask. The flask was cooled in an ice bath for 15 min and filtered. The filtrate was neutralized with acidic resin, and concentrated to dryness (Fraction B). The residue in the filter was washed with hot DMF and concentrated to dryness (Fraction A).

Fractions A and B were separately suspended in n-butanol (200 ml), treated with MR-ethylenediamine resin (20 g) and heated to 100° C. for 24 h. The hot solution from fraction A was filtered over a celite pad and washed with 1:1 methanol-water. The combined filtrate was concentrated to dryness (Fraction C, 853 mg). Proton NMR of the product indicated it to be the desired triglucosamine product 29. $^1$H-NMR (D$_2$O) δ: 4.54, 4.52, and 4.37 (3×H-1), 4.01, 3.98, 3.87, 3.80 (6×H-6), 3.63 (OCH$_3$), 2.78, 2.74, and 2.70 (3×H-2). Mass spectral data (ESI): m/e calc. 515.23 (100%); Obs. M+Na=516.2.

Similarly, the reaction mixture from Fraction B was filtered, washed and concentrated to dryness. The yellow solid was dissolved in water and the aqueous layer was extracted twice with methylenechloride to remove the by-product methyl benzoate. Finally, the aqueous layer was concentrated to dryness, the residue redissolved in water, and lyophilized (Fraction E). NMR analysis of the Fraction E product indicated incomplete phthalimide removal. The solid was suspended in n-butanol (100 ml) and heated to 104° C. MR-Ethylenediamine resin (9 g) was added and the reaction was continued for two days. The hot reaction mixture was filtered over a celite pad, washed with 1:1 methanol water (30 ml), and then with water (2×15 ml). The combined filtrate was concentrated to dryness. The residue was dissolved in water and lyophilized (Fraction F). The NMR spectrum of Fraction F showed that though the major product was the desired triglucosamine product 29, it was contaminated with some incompletely deprotected trisaccharide.

Example 25

Synthesis of Tetraglucosamine from Derivatized Glucosamine Tetrasaccharide

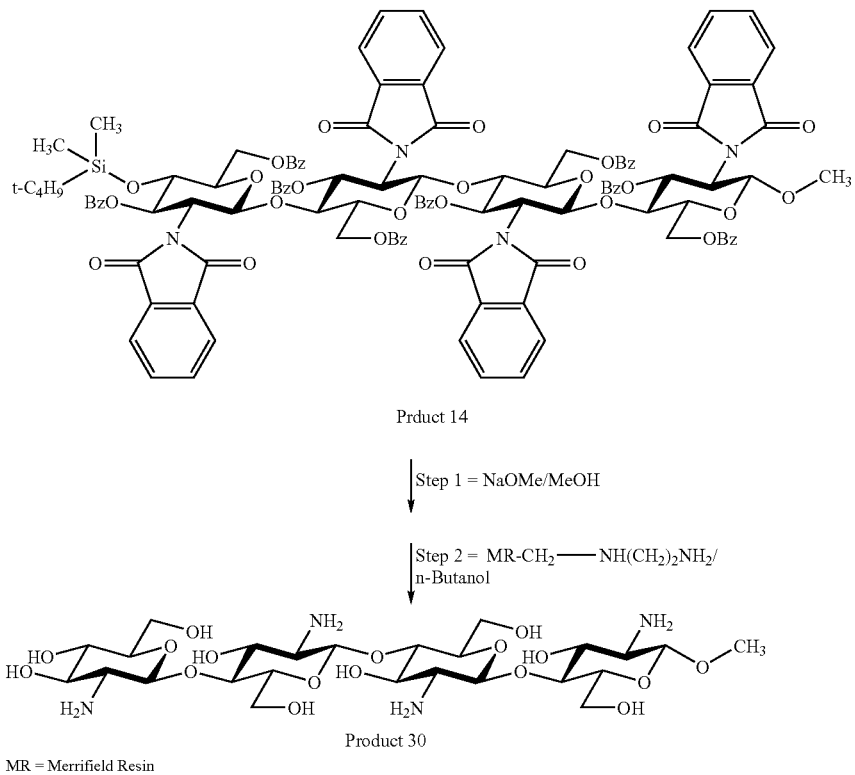

Step 1: The derivatized tetrasaccharide product 14 (7.7 g, 3.6 mmol) was dissolved in anhydrous methanol (450 ml). Sodium methoxide solution (0.5 M, 7.5 ml) was added and the solution was stirred at room temperature for 7 days. This was then refluxed for 2 days. The clear solution deposited lots of solid after two days of refluxing. The solution was cooled and the deposited solid was filtered over a 0.1μ filter. The residue was redissolved in dimethylformamide (100 ml) and concentrated to dryness (Fraction B, 3.53 g). The filtrate was neutralized with acidic resin and concentrated to dryness (Fraction C). The solid from this was repeatedly washed with acetonitrile to remove the methylbenzoate by-product, the residue redissolved in DMF and concentrated to dryness (1.14 g).

Step 2: Fraction B (3.53 g) was suspended in 100 ml of n-butanol and heated to 100° C. MR-Ethylenediamine resin (30 g) was added and the reaction was continued for 18 h. The hot solution was filtered over a celite pad and the residue further washed with water. The filtrate was concentrated to dryness (Fraction D). The proton NMR analysis of Fraction D confirmed the identity and purity of the product as the desired tetraglucosamine product 30. The product was re-dissolved in water and lyophilized (630 mg). $^1$H-NMR (D$_2$O) δ: 4.51, 4.51, 4.48, and 4.34 (4×H-1), 3.98, 3.98, 3.84, 3.77 (8×H-6), 3.60 (OCH$_3$), 2.75, 2.75, 2.70, and 2.66 (4×H-2). Mass spectral data (Electrospray): m/e calc. 676.67 (100%); Obs. M+H=677.3.

The Merrifield resin was washed with hot DMF (100 ml) and the filtrate was concentrated to dryness. A white solid was obtained. NMR examination of this solid in DMF-d7 showed that it was the starting material from Step 1. This was suspended in n-butanol (250 ml) containing MR-ethylenediamine resin (15 g) and heated to 104° C. for two days. It was then filtered over a celite pad and the residue washed with 1:1 methanol-water. The combined filtrate was concentrated to dryness and lyophilized to obtain more of the desired tetraglucosamine product 30 (381 mg).

Example 26

Synthesis of Hexaglucosamine from Derivatized Glucosamine Hexasaccharide

General Procedure for the Synthesis of Hexaglucosamine and Higher Oligomers

The procedure described above was not suitable for the efficient removal of protecting groups in hexasaccharide and higher oligomers, as the de-benzoylation was incomplete and the intermediate products formed were insoluble in methanol and n-butanol. We discovered that in fact these oligomers could be efficiently deprotected when treated with hydrazine in n-butanol at higher temperature. Typically, the hexamer (2.0 g) and higher derivatives were suspended in n-butanol (50 ml) and the suspension heated to 105° C. Hydrazine (4.5 g) was added and the heating was maintained for 24 h. A thick precipitate resulted in the reaction flask. The solution was filtered hot and washed a few times with hot methanol. This removed the by-products formed in the reaction (benzoyl hydrazide and phthalhydrazide). The residue on the filter was washed with deionized water and the aqueous filtrate concentrated to dryness. The residue was redissolved in deionized water, the insoluble material was filtered off and the clear filtrate was lyophilized. It has the completely deprotected oligoglucosamine and some amount of phthalhydrazide, as evidenced from the proton NMR spectrum.

Synthesis of hexaglucosamine product 32:

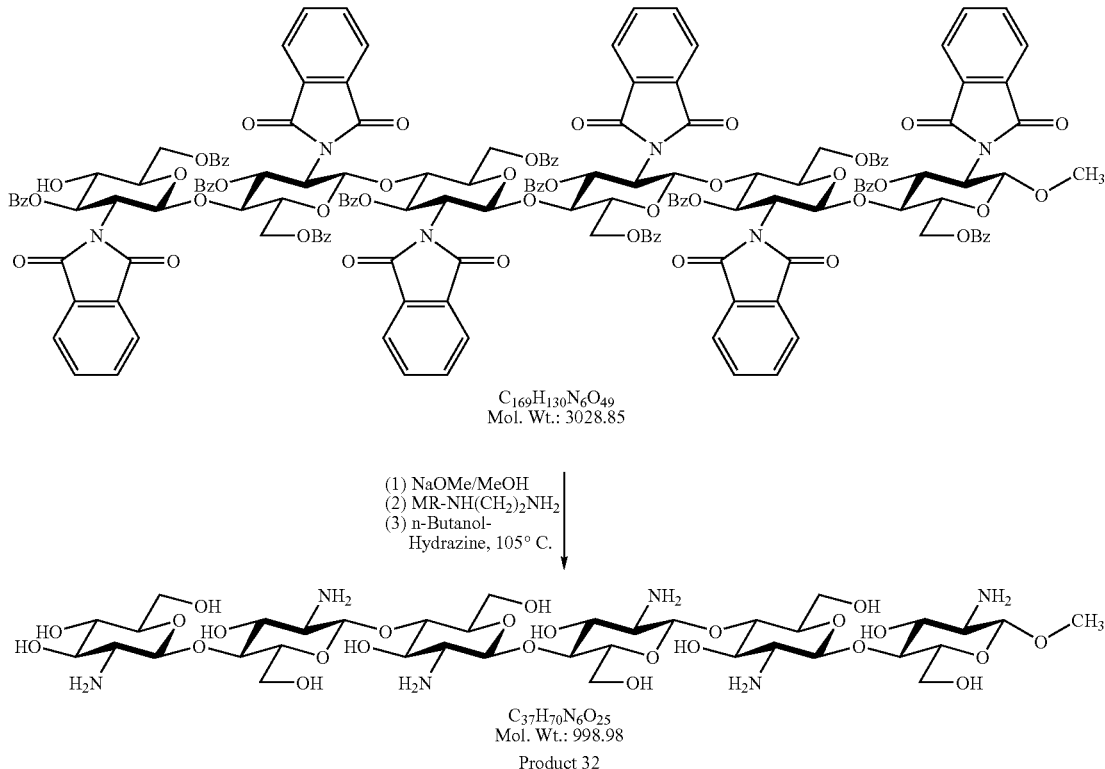

Product 32

The hexasaccharide product (9.0 g, 3.0 mmol) was dissolved in anhydrous methanol (500 ml). Sodium methoxide solution (0.5 M, 7.5 ml) was added. Anhydrous THF (40 ml) was added to dissolve any suspended material and the solution was stirred at room temperature for 1 day. This was then refluxed for 2 days. The reaction mixture was brought down to room temperature, the solid (Fraction A) in the flask filtered over a celite pad and the filtrate neutralized with sulfonic acid resin, refiltered and concentrated to dryness (Fraction B). The residue B was suspended in EtOAc—Hexane (1:1) and filtered, and the process repeated twice. The dark brown solid was dried under vacuum (5.29 g). The solid A on the celite pad was extracted with hot DMF and concentrated to dryness (0.8 g). Proton NMR of both A&B showed incomplete de-O-benzoylation (presence of benzoate signals between 7 to 8 ppm).

Fraction B (5.3 g) was suspended in methanol (300 ml). Sodium methoxide solution (0.5 M, 7 ml) was added and the solution was stirred at room temperature for 2 days and then refluxed for 2 days. The precipitated material was filtered and the product residue was re-extracted with DMF. NMR showed again incomplete de-benzoylation (recovered product weight 2.2 g)

Similarly, fraction A was suspended in methanol (100 ml). Sodium methoxide solution (0.5 M, 2 ml) was added and the solution was stirred at room temperature for 2 days and then refluxed for 2 days. NMR indicated most of the benzoates had been removed, but not quantitatively.

Both A and B were combined, suspended in n-butanol (100 ml) and heated to 105° C. Anhydrous hydrazine (4.8 g) was added and the heating continued for a day. The precipitate was filtered and the residue washed extensively with methanol. The remaining residue was dissolved in water and lyophilized. Proton NMR of the product indicated the completely deprotected hexasaccharide product 32 contaminated with phthalhydrazide. $^1$H-NMR (D$_2$O) δ: 8.17, 7.92 (Phthalhydrazide), 4.54, 4.45 (H-1s), 3.60 (OCH$_3$), 2.79 (H-2s). Mass spectral data (MALDI) for product 32: m/e calc. 998.44; Obs. M+H=999.0, M+Na=1021.0.

Synthesis of heptaglucosamine product 33:

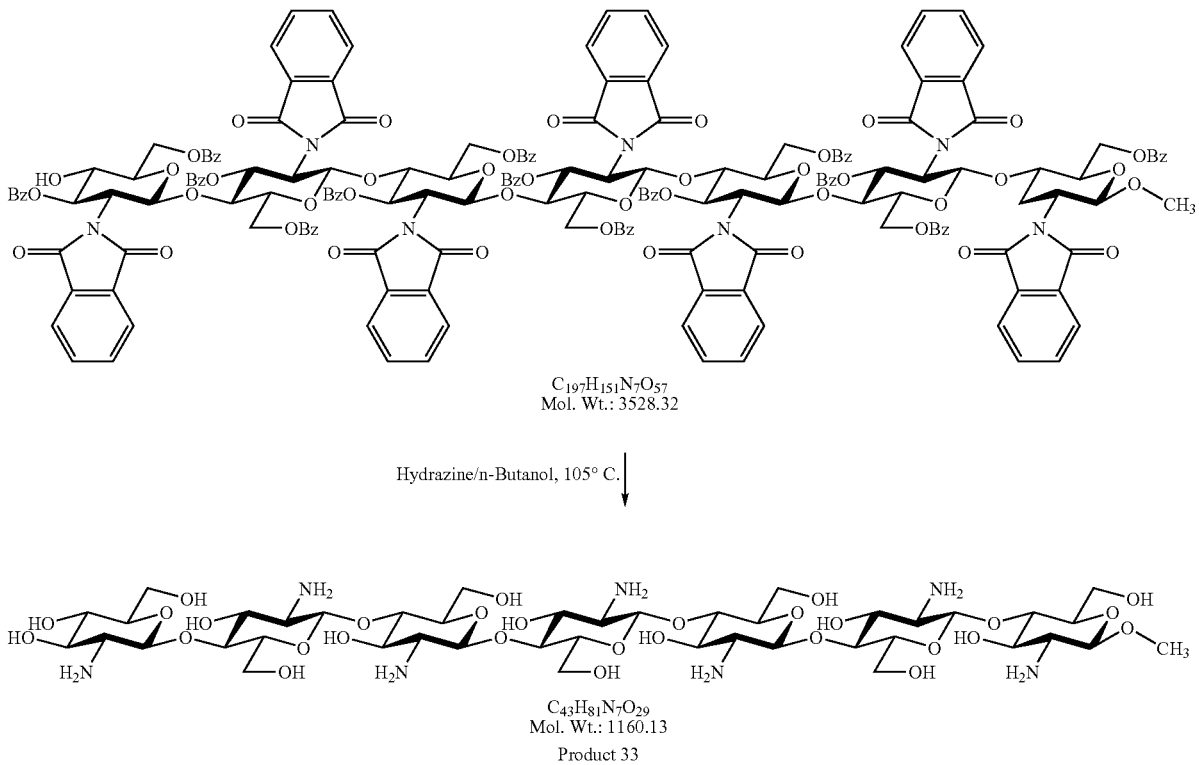

$C_{197}H_{151}N_7O_{57}$
Mol. Wt.: 3528.32

Hydrazine/n-Butanol, 105° C.

$C_{43}H_{81}N_7O_{29}$
Mol. Wt.: 1160.13
Product 33

Heptasaccharide (8.0 g) was dissolved in n-Butanol (200 ml) and heated to 105° C. Hydrazine (14 g) was added to the hot suspension and stirred. Initially, the heptasaccharide in n-butanol did not dissolve despite heating. After the addition of hydrazine, the solution became clear, then cloudy (10 min) and precipitate started to appear in the reaction flask. The reaction mixture was refluxed overnight and the hot suspension was filtered over a celite pad. The precipitate was washed with hot n-butanol and hot methanol (3×40 ml). The residue on the celite pad was extracted with water and concentrated to dryness to give product 33. $^1$H-NMR (D$_2$O) δ: 8.23, 7.98 (Phthalhydrazide), 4.59, 4.49 (H-1s), 3.65 (OCH$_3$), 2.84 (H-2s). Mass spectral data (MALDI) for product 32: m/e calc. 1159.51; Obs. M+Na=1182.3.

Synthesis of heptaglucosamine product 34:
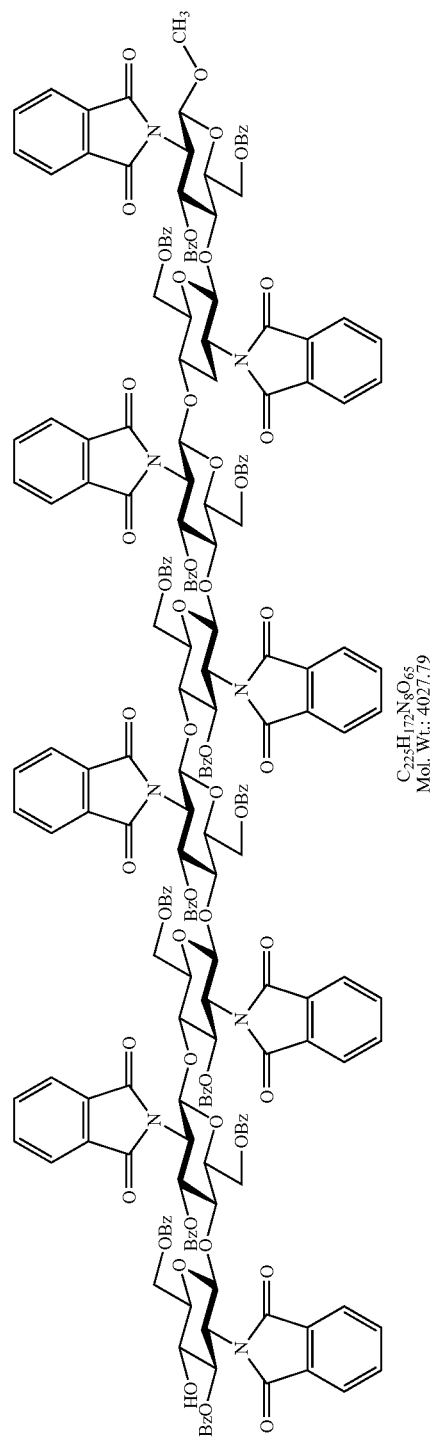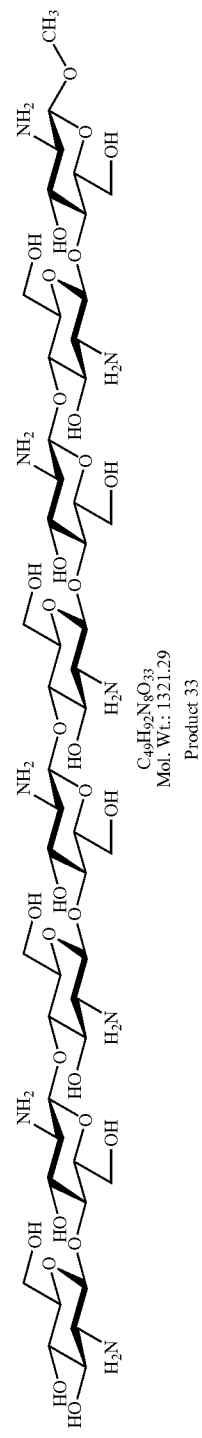

Octasaccharide (4.7 g) was dissolved in n-Butanol (100 ml) and heated to 105° C. Hydrazine (9.0 g) was added to the hot suspension and stirred. Initially, the heptasaccharide in n-butanol did not dissolve despite heating. After the addition of hydrazine, the solution became clear, then cloudy (10 min) and precipitate started to appear in the reaction flask. The reaction mixture was refluxed overnight and the hot suspension was filtered over a celite pad. The precipitate was washed with hot n-butanol and hot methanol (3×40 ml). The residue on the celite pad was extracted with water and concentrated to dryness to give product 33. $^1$H-NMR (D$_2$O) δ: 8.23, 7.98 (Phthalhydrazide), 4.59, 4.49 (H-1s), 3.65 (OCH$_3$), 2.84 (H-2s).

What is claimed is:

1. A process for forming a glycosidic linkage between two hexoses, comprising:
   i. providing a protected thioglycoside donor and a suitably protected glycosyl acceptor, both of which are hexoses;
   ii. activating the thioglycoside donor using as activating agents an N-haloimide and at least about a 0.5 molar equivalent amount, to the glycosyl acceptor, of a perfluoroalkyl sulfonic acid in the presence of said acceptor; and
   iii. reacting the thioglycoside donor and glycosyl acceptor at a temperature from about -20° C. to about -70° C.;
   wherein the thioglycoside and the glycosyl acceptor form a beta glycosidic linkage;
   wherein the protected thioglycoside donor has the formula:

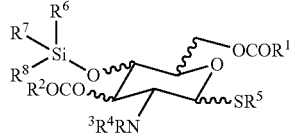

(I)

wherein R$^1$ and R$^2$ are each independently selected from H and C$_1$ to C$_{20}$ alkyl, aryl, and aralkyl groups; R$^3$ and R$^4$ are each independently selected from monofunctional acyl, bifunctional acyl, phthaloyl, trichloroacetyl, and tetrachlorophthaloyl groups; and R$^5$, R$^6$, R$^7$ and R$^8$ are each independently selected from C$_1$ to C$_{20}$ alkyl, aryl, and aralkyl groups.

2. The process of claim 1 wherein the perfluoroalkyl sulfonic acid is in at least about an equimolar equivalent amount.

3. The process of claim 1 wherein methyltriflate is included in the reaction.

4. The process of claim 1 wherein the N-haloimide is an N-halosuccinimide.

5. The process of claim 1 wherein the activating agents comprise N-iodosuccinimide and triflic acid.

6. The process of claim 1 wherein the hexoses are selected from glucose, galactose, glucosamine and galactosamine.

7. The process of claim 1 wherein the beta linkage is 1,4.

8. The process of claim 1 wherein the linkage position of the thioglycoside is protected by a trisubstituted silicon group.

9. The process of claim 8 wherein the trisubstituted silicon group has substituents selected from C$_1$ to C$_{20}$ alkyl, aryl, and aralkyl groups.

10. The process of claim 1 wherein the thioglycoside donor contains non-linkage positions that are each protected by a member of the group consisting of C$_1$ to C$_{20}$ alkoyl, aroyl, and aralkoyl ester groups.

11. The process of claim 1 wherein the reaction is carried out at a temperature from about -50° C. to about -60° C.

12. A process of extending a chain of a polyhexose having a protecting group at a linkage position comprising:
   a) removing the protecting group from the polyhexose linkage position to form a polyhexose acceptor;
   b) providing a protected thioglycoside donor;
   c) activating the polyhexose and the thioglycoside using as activating agents an N-haloimide and at least a 0.5 molar amount of a perfluoroalkyl sulfonic acid; and
   d) reacting the thioglycoside donor and polyhexose acceptor at a temperature from about -20° C. to about -70° C.;
   wherein the thioglycoside and the polyhexose form a beta linked polyhexose that has a length of x 1 monomer units wherein x is the length of the starting polyhexose and the thioglycoside donor has the formula:

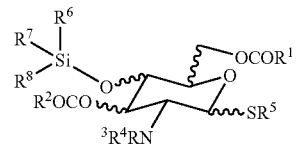

(I)

wherein R$^1$ and R$^2$ are each independently selected from H and C$_1$ to C$_{20}$ alkyl, aryl, and aralkyl groups; R$^3$ and R$^4$ are each independently selected from monofunctional acyl, bifunctional acyl, phthaloyl, trichloroacetyl, and tetrachlorophthaloyl groups; and R$^5$, R$^6$, R$^7$ and R$^8$ are each independently selected from C$_1$ to C$_{20}$ alkyl, aryl, and aralkyl groups.

13. The process of claim 12 wherein said perfluoroalkyl sulfonic acid comprises triflic acid.

14. The process of claim 12 wherein methyltriflate is included in the reaction.

15. The process of claim 12 wherein each of said removing of the protecting group, providing a thioglycoside, and activating the polyhexose and thioglycoside is repeated at least one additional time.

16. A process of claim 12 wherein R$_3$ and R$_4$ are acyl groups derived from a phthaloyl unit.

17. A process of claim 12 wherein R$_5$ is a p-toluyl group.

18. A process of claim 12 wherein R$_6$ and R$_7$ are methyl groups.

* * * * *

UNITED STATES PATENT AND TRADEMARK OFFICE
CERTIFICATE OF CORRECTION

PATENT NO. : 7,485,718 B2
APPLICATION NO. : 11/154457
DATED : February 3, 2009
INVENTOR(S) : Sabesan Subramaniam It is certified that error appears in the above-identified patent and that said Letters Patent is hereby corrected as shown below:

At column 21, line 57, the word "Monomer (II) (80.6 g," should read "Monomer (I) (80.6 g,"

At column 21, line 67 through column 22, line 3, the sentence "An additional 100 ml of the triflic acid/lmethyltriflate solution was added to the reaction mixture dropwise to reduce of the viscosity." is replaced by "An additional 100 ml of methylene chloride was added to the reaction mixture dropwise to reduce the viscosity."

At column 39, lines 10-13 the sentence "An additional 100 ml of the triflic acid/lmethyltriflate solution was added to the reaction mixture dropwise to reduce of the viscosity." is replaced by "An additional 100 ml of methylene chloride was added to the reaction mixture dropwise to reduce the viscosity."

At column 43, lines 31-34 the sentence "An additional 100 ml of the triflic acid/lmethyltriflate solution was added to the reaction mixture dropwise to reduce of the viscosity." is replaced by "An additional 100 ml of methylene chloride was added to the reaction mixture dropwise to reduce the viscosity."

At column 49, lines 58-61 the sentence "An additional 100 ml of triflic acid/lmethyltriflate solution was added to the reaction mixture dropwise to reduce of the viscosity." is replaced by "An additional 100 ml of methylene chloride was added to the reaction mixture dropwise to reduce the viscosity."

At column 57, lines 35-57 the sentence "After 4 h, an additional 50 ml of triflic acid/lmethyltriflate solution was added to the reaction mixture dropwise to reduce of the viscosity." is replaced by "After 4 hours, an additional 50ml of methylene chloride was added to the reaction mixture dropwise to reduce the viscosity."

At column 63, lines 61-63 the sentence "After 4 h, an additional 50 ml of TfOH/lmethyltriflate solution was added to the reaction mixture dropwise to reduce of the viscosity." is replaced by "After 4 hours, an additional 50ml of methylene chloride was added to the reaction mixture dropwise to reduce the viscosity."

CERTIFICATE OF CORRECTION (continued)
U.S. Pat. No. 7,485,718 B2

At column 71, lines 12-14 the sentence "After 4 h, an additional 50 ml of TfOH/lmethyltriflate solution was added to the reaction mixture dropwise to reduce of the viscosity." is replaced by "After 4 hours, an additional 50ml of methylene chloride was added to the reaction mixture dropwise to reduce the viscosity."

Signed and Sealed this

Second Day of February, 2010

David J. Kappos
*Director of the United States Patent and Trademark Office*